United States Patent [19]
Schallner et al.

[11] Patent Number: 5,756,805
[45] Date of Patent: May 26, 1998

[54] 4-CYANOPHENYLIMINO HETEROCYCLES

[75] Inventors: Otto Schallner, Monheim; Roland Andree; Mark Wilhelm Drewes, both of Langenfeld; Markus Dollinger; Hans-Joachim Santel, both of Leverkusen, all of Germany

[73] Assignee: Bayer Aktiengesellschaft, Leverkusen, Germany

[21] Appl. No.: 738,991

[22] Filed: Oct. 24, 1996

Related U.S. Application Data

[62] Division of Ser. No. 321,295, Oct. 11, 1994, abandoned.

[30] Foreign Application Priority Data

Oct. 18, 1993 [DE] Germany .................. 43 35 438.6

[51] Int. Cl.$^6$ .................................................. C07C 255/07
[52] U.S. Cl. .................................... 558/413; 558/414
[58] Field of Search ........................... 558/413, 414

[56] References Cited

FOREIGN PATENT DOCUMENTS 9221684  12/1992  WIPO .

*Primary Examiner*—Johann Richter
*Assistant Examiner*—Ebenezer Sackey

*Attorney, Agent, or Firm*—Sprung Kramer Schaefer & Briscoe

[57] ABSTRACT

Herbicidal 4-cyanophenylimino heterocycles of the formula

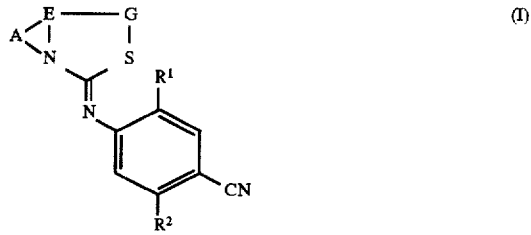

in which

R$^1$ represents hydrogen or halogen,

R$^2$ represents halogen, cyano, hydroxyl, amini, X—R$^3$, —N(R$^4$)—CO—R$^5$ or —N(R$^4$)—SO$_2$R$^5$, X represents oxygen, sulphur or a single bond, A represents alkanediyl or alkenediyl each of which is optionally substituted, E represents nitrogen or carbon, and G represents nitrogen or represents carbon which is bonded to hydrogen or alkyl via an exo single bond or to oxygen or sulphur via an exo double bond, with some exceptions.

1 Claim, No Drawings

4-CYANOPHENYLIMINO HETEROCYCLES

This application is a division of U.S. Pat. No. 08/321,295 filed on Oct. 11, 1994, now abandoned.

The invention relates to novel 4-cyanophenylimino heterocycles, to processes for their preparation, and to their use as herbicides, as well as to novel intermediates for their synthesis.

It is already known that certain halogenoarylimino heterocycles exhibit herbicidal properties (cf. EP-A 238711, EP-A 273417, EP-A 312064, EP-A 410265, EP-A 457714, WO-A 92/21684). However, the herbicidal activity of these known compounds, and their ability to be tolerated by cultivated plants, is not always entirely satisfactory.

Novel 4-cyanophenylimino heterocycles of the general formula (I)

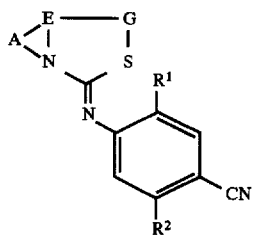

have now been found, in which $R^1$ represents hydrogen or halogen, $R^2$ represents halogen, cyano, hydroxyl, amino, or one of the following groupings —X—$R^3$, —N($R^4$)—CO—$R^5$ or —N($R^4$)—SO$_2$$R^5$, where X represents oxygen, sulphur or a single bond, $R^3$ represents alkyl, alkenyl, alkinyl, cycloalkyl, cycloalkylalkyl, aryl, arylalkyl, heterocyclyl or heterocyclylalkyl each of which is optionally substituted, $R^4$ represents hydrogen or alkyl, and $R^5$ represents alkyl, alkenyl, alkinyl, cycloalkyl, cycloalkylalkyl, aryl or arylalkyl each of which is optionally substituted, A represents alkanediyl or alkenediyl each of which is optionally substituted, E represents nitrogen or carbon, and G represents nitrogen or represents carbon which is bonded to hydrogen or alkyl via an exo single bond or to oxygen or sulphur via an exo double bond, where, for the case where E represents nitrogen, A does not represent optionally substituted trimethylene.

The novel 4-cyanophenylimino heterocycles of the general formula (I) are obtained when a) substituted thiocarbonylamino compounds of the general formula (II)

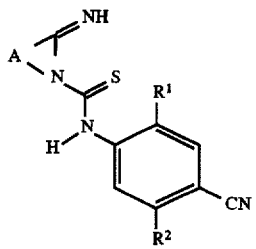

in which

A, $R^1$ and $R^2$ have the abovementioned meanings, are reacted with oxidizing agents or dehydrogenating agents, optionally in the presence of a reaction auxiliary and optionally in the presence of a diluent, or when b) substituted thiocarbonylamino compounds of the general formula (III)

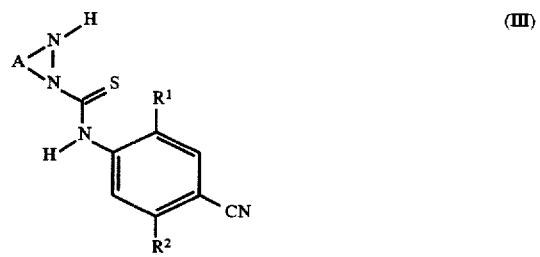

in which

A, $R^1$ and $R^2$ have the abovementioned meanings, are reacted with phosgene, optionally in the presence of a diluent, or when c) 4-cyanophenylimino heterocycles of the general formula (Ia)

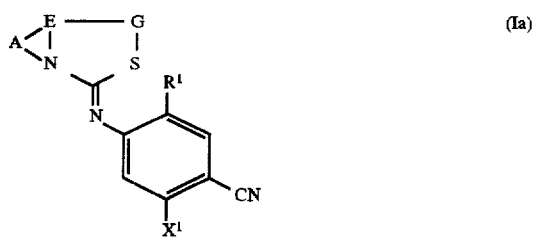

in which $R^1$, A, E and G have the abovementioned meanings, and $X^1$ represents halogen, are reacted with nucleophilic compounds of the general formulae (IV) or (V)

H—X—$R^3$ (IV)   H—N($R^4$)—SO$_2$$R^5$ (V)

in which

X, $R^3$, $R^4$ and $R^5$ have the abovementioned meanings, or with alkali metal salts of these compounds optionally in the presence of an acid acceptor and optionally in the presence of a diluent.

The novel compounds of the formula (I) may also be obtained by reacting imino heterocycles of the general formula (VI) with 4-halogenobenzonitriles of the general formula (VII) in accordance with the following formula scheme ($R^1$, $R^2$, A, E and G defined as above, $X^2$: halogen):

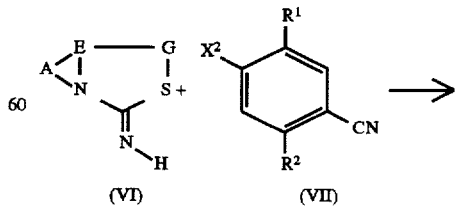

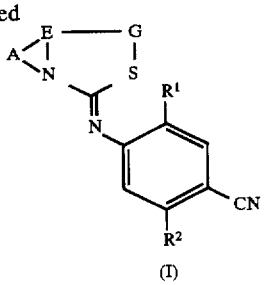

The novel 4-cyanophenylimino heterocycles of the general formula (I) are notable for their strong and selective herbicidal activity.

In the definitions, the saturated or unsaturated hydrocarbon chains, such as alkyl, alkanediyl, alkenyl, alkenediyl or alkinyl, are in each case straight-chain or branched.

Halogen generally represents fluorine, chlorine, bromine or iodine, preferably represents fluorine, chlorine or bromine, and in particular represents fluorine or chlorine.

The invention preferably relates to compounds of the formula (I) in which $R^1$ represents hydrogen, fluorine, chlorine or bromine, $R^2$ represents fluorine, chlorine, bromine, cyano, hydroxyl, amino, or one of the following groupings —X—$R^3$—, —N($R^4$)—CO—$R^5$ or —N ($R^4$)—$SO_2R^5$, where X represents oxygen, sulphur or a single bond, $R^3$ represents alkyl having 1 to 8 carbon atoms and which is optionally substituted by fluorine, chlorine, bromine, cyano, carboxyl, $C_1$–$C_4$-alkoxy, $C_1$–$C_4$-alkoxy-$C_1$–$C_4$-alkoxy, $C_1$–$C_4$-alkylthio, $C_1$–$C_4$-alkylcarbonyl, $C_1$–$C_4$-alkoxy-carbonyl or $C_5$–$C_6$-cycloalkyloxycarbonyl, $R^3$ furthermore represents alkenyl or alkinyl having in each case 2 to 8 carbon atoms and which are in each case optionally substituted by fluorine, chlorine or bromine, $R^3$ furthermore represents cycloalkyl or cycloalkylalkyl having in each case 3 to 8 carbon atoms in the cycloalkyl moiety and optionally 1 to 4 carbon atoms in the alkyl moiety and which are in each case optionally substituted by fluorine, chlorine, bromine, cyano, carboxyl, $C_1$–$C_4$-alkyl or $C_1$–$C_4$-alkoxy-carbonyl, or represents phenyl, benzyl, phenylethyl, phenylpropyl or phenylbutyl each of which is optionally substituted, or represents in each case optionally substituted heterocyclyl, heterocyclylmethyl, heterocyclylethyl, heterocyclylpropyl or heterocyclylbutyl having in each case 3 to 8 ring members, of which at least one is an oxygen, sulphur or nitrogen atom and optionally 1 to 3 are additional nitrogen atoms, where the heterocyclyl group can be saturated or unsaturated and the above-mentioned cyclic groups optionally contain substituents from the following list:

halogen, cyano, nitro, carboxyl, carbamoyl, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkylsulphinyl, $C_1$–$C_4$-halogenoalkylsulphinyl, $C_1$–$C_4$-alkylsulphonyl, $C_1$–$C_4$-halogenoalkylsulphonyl and $C_1$–$C_4$-alkoxycarbonyl, $R^4$ represents hydrogen or represents alkyl having 1 to 8 carbon atoms, and $R^5$ represents alkyl having 1 to 8 carbon atoms and which is optionally substituted by fluorine, chlorine, bromine, cyano, carboxyl, $C_1$–$C_4$-alkoxy, $C_1$–$C_4$-alkoxy-$C_1$–$C_4$-alkoxy, $C_1$–$C_4$-alkylthio, $C_1$–$C_4$-alkyl-carbonyl or $C_1$–$C_4$-alkoxy-carbonyl, $R^5$ furthermore represents alkenyl or alkinyl having in each case 2 to 8 carbon atoms and which are in each case optionally substituted by fluorine, chlorine or bromine, $R^5$ furthermore represents cycloalkyl or cycloalkylalkyl having in each case 3 to 8 carbon atoms in the cycloalkyl moiety and optionally 1 to 4 carbon atoms in the alkyl moiety and which are in each case optionally substituted by fluorine, chlorine, bromine, cyano, carboxyl, $C_1$–$C_4$-alkyl or $C_1$–$C_4$-alkoxy-carbonyl, or represents aryl or arylalkyl having 6 or 10 carbon atoms in the aryl moiety and optionally 1 to 4 carbon atoms in the alkyl moiety and which are in each case optionally substituted by fluorine, chlorine, bromine, cyano, nitro, carboxyl, carbamoyl, by $C_1$–$C_4$-alkyl, $C_1$–$C_4$-alkoxy, $C_1$–$C_4$-alkylthio, $C_1$–$C_4$-alkyl-sulphinyl or $C_1$–$C_4$-alkylsulphonyl (which are in each case optionally substituted by fluorine and/or chlorine), by dimethylaminosulphonyl or diethylaminosulphonyl, by $C_1$–$C_4$-alkoxy-carbonyl (which is optionally substituted by fluorine, chlorine, bromine, methoxy or ethoxy), by phenyl, phenylmethyl, phenoxy, phenylthio, phenylsulphinyl or phenylsulphonyl (which are in each case optionally substituted by fluorine, chlorine, bromine, cyano, methyl, methoxy, trifluoromethyl, difluoromethoxy and/or trifluoromethoxy).

A represents alkanediyl or alkenediyl having in each case 2 to 6 carbon atoms and which are in each case optionally substituted by fluorine, chlorine, bromine or $C_1$–$C_4$-alkyl (which is optionally substituted by fluorine and/or chlorine), E represents nitrogen or carbon, and G represents nitrogen or carbon which is bonded to hydrogen or $C_1$–$C_6$-alkyl via an exo single bond, or to oxygen or sulphur via an exo double bond, where, for the case where E represents nitrogen, A does not represent optionally substituted trimethylene.

The invention relates, in particular, to compounds of the formula (I) in which $R^1$ represents hydrogen, fluorine or chlorine, $R^2$ represents fluorine, chlorine, bromine, cyano, hydroxyl, amino, or one of the following groupings —X—$R^3$ —N($R^4$)—CO—$R^5$ or —N($R^4$)—$SO_2R^5$, where X represents oxygen, sulphur or a single bond, $R^3$ represents methyl, ethyl, n- or i-propyl or n-, i-, s- or t-butyl which are in each case optionally substituted by fluorine, chlorine, bromine, cyano, carboxyl, methoxy, ethoxy, methoxyethoxy, ethoxyethoxy, methylthio, ethylthio, acetyl, propionyl, methoxycarbonyl or ethoxycarbonyl, $R^3$ furthermore represents allyl, crotonyl, 1-methylallyl, propargyl or 1-methyl-propargyl which are in each case optionally substituted by fluorine or chlorine, $R^3$ furthermore represents cyclopropyl, cyclobutyl, cyclopentyl, cyclohexyl, cyclopropylmethyl, cyclobutylmethyl, cyclopentylmethyl or cyclohexylmethyl which are in each case optionally substituted by fluorine, chlorine, methyl, ethyl, n- or i-propyl, methoxycarbonyl or ethoxy-carbonyl, $R^4$ represents hydrogen, methyl, ethyl, n- or i-propyl or n-, i- or s-butyl, $R^5$ represents methyl, ethyl, n- or i-propyl or n-, i-, s- or t-butyl which are in each case optionally substituted by fluorine, chlorine, bromine, cyano, carboxyl, methoxy, ethoxy, methoxyethoxy, ethoxyethoxy, methylthio, ethylthio, acetyl, propionyl, methoxycarbonyl or ethoxycarbonyl, $R^5$ furthermore represents allyl, crotonyl, 1-methyl-allyl, propargyl or 1-methyl-propargyl which are in each case optionally substituted by fluorine or chlorine, $R^5$ furthermore represents cyclopropyl, cyclobutyl, cyclopentyl, cyclohexyl, cyclopropylmethyl, cyclobutylmethyl, cyclopentylmethyl or cyclohexylmethyl which are in each case optionally substituted by fluorine, chlorine, methyl, ethyl or n- or i-propyl, $R^5$ furthermore represents phenyl, naphthyl, benzyl or phenylethyl which are in each case optionally substituted by fluorine, chlorine, bromine, cyano, methyl, ethyl, n- or i-propyl, n-, i-, s- or t-butyl, methoxy, ethoxy, methylthio, ethylthio, methylsulphinyl, ethylsulphinyl, methylsulphonyl, ethylsulphonyl, trifluoromethyl, difluoromethoxy, trifluoromethoxy, trifluoromethylthio, trifluoromethylsulphinyl, trifluoromethylsulphonyl, dimethylaminosulphonyl, methoxycarbonyl, ethoxycarbonyl, phenyl, phenoxy or phenylsulphonyl, A represents propane-1,3-diyl (trimethylene), butane-1,4-diyl (tetramethylene), 1-propene-1,3-diyl, 1-butene-1, 4-diyl or 2-butene-1,4-diyl which are in each case optionally substituted by fluorine, chlorine, bromine, methyl, ethyl or n- or i-propyl, E represents nitrogen or carbon, and G represents nitrogen or carbon which is bonded to hydrogen, methyl, ethyl, n- or i-propyl or n-, i-, s- or t-butyl via an exo single bond, or to oxygen via an exo double bond, where, for the case where E represents nitrogen, A does not represent optionally substituted trimethylene.

A particularly preferred group of compounds of the formula (I) are the compounds of the general formula (IA)

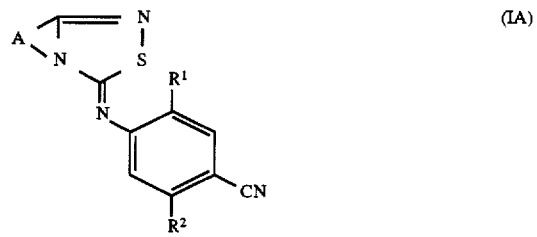

in which $R^1$, $R^2$ and A have the meaning given above as being particularly preferred.

A further particularly preferred group of compounds of the formula (I) are the compounds of the general formula (IB)

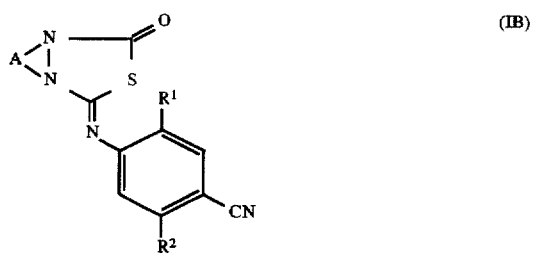

in which $R^1$, $R^2$ and A have the meaning given above as being particularly preferred.

Examples of the compounds of the formula (I) according to the invention are listed in Table 1 below.

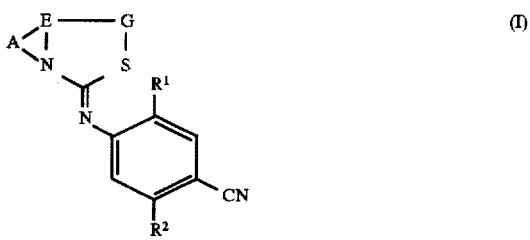

TABLE 1

| | Examples of the compounds of the formula (I) | | | | |
|---|---|---|---|---|---|
| $R^1$ | $R^2$ | A | | E | G |
| F | O—CH(CH$_2$F)$_2$ | —(CH$_2$)$_4$— | | N | CO |
| F | O—CH$_2$—C(CH$_3$)=CH$_2$ | —(CH$_2$)$_4$— | | N | CO |
| F | S—CH$_2$—⟨tetrahydrofuran-2-yl⟩ | —(CH$_2$)$_4$— | | N | CO |
| F | O—CH$_2$—⟨tetrahydropyran-2-yl⟩ | —(CH$_2$)$_4$— | | N | CO |
| F | O—⟨cyclopropyl-COOC$_2$H$_5$⟩ | —(CH$_2$)$_4$— | | N | CO |

TABLE 1-continued

Examples of the compounds of the formula (I)

| R¹ | R² | A | E | G |
|---|---|---|---|---|
| F | 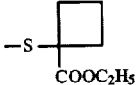 -S-◻-COOC₂H₅ | $-(CH_2)_4-$ | N | CO |
| F | 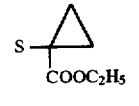 S-△-COOC₂H₅ | $-(CH_2)_4-$ | N | CO |
| F | 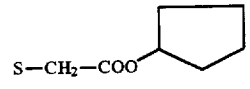 S—CH₂—COO-⬠ | $-(CH_2)_4-$ | N | CO |
| F | $S-CH_2-COOC_5H_{11}\text{-}n$ | $-(CH_2)_4-$ | N | CO |
| F | 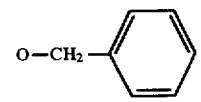 O—CH₂—⬡ | $-(CH_2)_4-$ | N | CO |
| F | 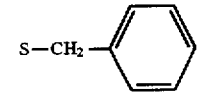 S—CH₂—⬡ | $-(CH_2)_4-$ | N | CO |
| F | $O-CH_2CH_2-OCH(CH_2F)_2$ | $-(CH_2)_4-$ | N | CO |
| F | $S-CH(CH_3)_2$ | $-(CH_2)_4-$ | N | CO |
| F | $O-CH_2-CCl=CH_2$ | $-(CH_2)_4-$ | N | CO |
| F | 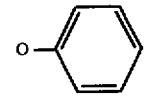 O—⬡ | $-(CH_2)_4-$ | N | CO |
| F | $O-CH_2CN$ | $-(CH_2)_4-$ | N | CO |
| F | $O-CH_2COOC_2H_4-OCH_3$ | $-(CH_2)_4-$ | N | CO |
| F | $O-CH_2-COO-CH(CH_3)COOC_2H_5$ | $-(CH_2)_4-$ | N | CO |
| F | $OCH_2-COOCH_2-COOC_2H_5$ | $-(CH_2)_4-$ | N | CO |
| F | $O-CHF_2$ | $-(CH_2)_4-$ | N | CO |
| F | $O-CH_2CH_2-OCH_2CF_3$ | $-(CH_2)_4-$ | N | CO |
| F | $OCH_2CF_3$ | $-(CH_2)_4-$ | N | CO |
| F | $OCF_3$ | $-(CH_2)_4-$ | N | CO |
| F | $OCH_2CH(CH_3)-OC_2H_5$ | $-(CH_2)_4-$ | N | CO |
| F | 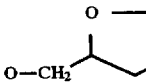 O—CH₂-(tetrahydrofuran-2-yl-O-) | $-(CH_2)_4-$ | N | CO |
| F | $OCH_2-CH=CH_2$ | $-(CH_2)_4-$ | N | CO |
| F | $OH$ | $-(CH_2)_4-$ | N | CO |
| F | $OCH_2-C\equiv CH$ | $-(CH_2)_4-$ | N | CO |
| F | $SCH_2C\equiv CH$ | $-(CH_2)_4-$ | N | CO |
| F | $OCH_2COOC_2H_5$ | $-(CH_2)_4-$ | N | CO |
| F | $S-C(CH_3)_3$ | $-(CH_2)_4-$ | N | CO |
| F | $OCH_2-COOC_5H_{11}\text{-}n$ | $-(CH_2)_4-$ | N | CO |
| F | $OCH(CH_3)-COOC_2H_5$ | $-(CH_2)_4-$ | N | CO |
| F | $OCH_2CH_2-OCH_3$ | $-(CH_2)_4-$ | N | CO |
| F | $OCH_2CH_2-OC_2H_5$ | $-(CH_2)_4-$ | N | CO |
| F | $O(CH_2CH_2O)_2-C_2H_5$ | $-(CH_2)_4-$ | N | CO |
| F | $S-C_3H_7\text{-}n$ | $-(CH_2)_4-$ | N | CO |
| F | $S-C_2H_5$ | $-(CH_2)_4-$ | N | CO |
| F | $S-CH_3$ | $-(CH_2)_4-$ | N | CO |
| F | $S-CH_2COOC_2H_5$ | $-(CH_2)_4-$ | N | CO |
| F | $SCH_2CH_2-COOC_2H_5$ | $-(CH_2)_4-$ | N | CO |
| F | $O-CH_2-C\equiv C-CH_3$ | $-(CH_2)_4-$ | N | CO |
| F | $OCH_2-CH=CH-Cl$ | $-(CH_2)_4-$ | N | CO |
| F | $O-CH(CH_3)C\equiv CH$ | $-(CH_2)_4-$ | N | CO |
| F | $OCH(CH_3)C\equiv C-CH_3$ | $-(CH_2)_4-$ | N | CO |

TABLE 1-continued

Examples of the compounds of the formula (I)

| R¹ | R² | A | E | G |
|---|---|---|---|---|
| F | O—CH(CH₃)CH=CH₂ | —(CH₂)₄— | N | CO |
| F | OCH₂CH=CH—CH₃ | —(CH₂)₄— | N | CO |
| F | O—CH₃ | —(CH₂)₄— | N | CO |
| F | O—C₂H₅ | —(CH₂)₄— | N | CO |
| F | O—C₃H₇-n | —(CH₂)₄— | N | CO |
| F | O—C₃H₇-iso | —(CH₂)₄— | N | CO |
| F | O–⌷–COOC₂H₅ (oxetane with COOC₂H₅) | —(CH₂)₄— | N | CO |
| F | tetrahydrofuran-O- | —(CH₂)₄— | N | CO |
| F | NHCH₃ | —(CH₂)₄— | N | CO |
| F | NHC₂H₅ | —(CH₂)₄— | N | CO |
| F | N(CH₃)₂ | —(CH₂)₄— | N | CO |
| F | NH—CH₂—COOC₂H₅ | —(CH₂)₄— | N | CO |
| F | piperidin-1-yl | —(CH₂)₄— | N | CO |
| F | morpholin-4-yl | —(CH₂)₄— | N | CO |
| F | NH—SO₂CH₃ | —(CH₂)₄— | N | CO |
| F | NH—SO₂C₂H₅ | —(CH₂)₄— | N | CO |
| F | NH—SO₂C₃H₇-n | —(CH₂)₄— | N | CO |
| F | NH—SO₂C₃H₇-i | —(CH₂)₄— | N | CO |
| F | NH—SO₂C₄H₉-n | —(CH₂)₄— | N | CO |
| F | NH—SO₂C₈H₁₇-n | —(CH₂)₄— | N | CO |
| F | NH—COCH₃ | —(CH₂)₄— | N | CO |
| F | NH—COC₂H₅ | —(CH₂)₄— | N | CO |
| F | NH—COCF₃ | —(CH₂)₄— | N | CO |
| F | N(CH₃)—SO₂CH₃ | —(CH₂)₄— | N | CO |
| F | N(CH₃)—SO₂C₂H₅ | —(CH₂)₄— | N | CO |
| F | N(CH₃)—SO₂C₃H₇-n | —(CH₂)₄— | N | CO |
| F | NH—SO₂CF₃ | —(CH₂)₄— | N | CO |
| F | NH—SO₂—cyclopropyl | —(CH₂)₄— | N | CO |
| F | NH—SO₂—C₄F₉-n | —(CH₂)₄— | N | CO |
| F | N(CH₃)SO₂CF₃ | —(CH₂)₄— | N | CO |
| F | NH—SO₂—C₆H₅ | —(CH₂)₄— | N | CO |
| F | NH—SO₂CH₂—C₆H₅ | —(CH₂)₄— | N | CO |
| F | N(CH₃)—SO₂—C₆H₄—CH₃ | —(CH₂)₄— | N | CO |
| H | OCH₂CF₃ | —(CH₂)₄— | N | CO |
| H | OCF₃ | —(CH₂)₄— | N | CO |
| H | OCH₂CH(CH₃)—OC₂H₅ | —(CH₂)₄— | N | CO |

TABLE 1-continued

Examples of the compounds of the formula (I)

| R¹ | R² | A | E | G |
|---|---|---|---|---|
| H | (tetrahydrofuran-2-yl-methyl: O—CH₂—[tetrahydrofuran ring with O]) | —(CH₂)₄— | N | CO |
| H | OCH₂—CH=CH₂ | —(CH₂)₄— | N | CO |
| H | OH | —(CH₂)₄— | N | CO |
| H | OCH₂—C≡CH | —(CH₂)₄— | N | CO |
| H | SCH₂C≡CH | —(CH₂)₄— | N | CO |
| H | OCH₂COOC₂H₅ | —(CH₂)₄— | N | CO |
| H | S—C(CH₃)₃ | —(CH₂)₄— | N | CO |
| H | OCH₂—COOC₅H₁₁-n | —(CH₂)₄— | N | CO |
| H | OCH(CH₃)—COOC₂H₅ | —(CH₂)₄— | N | CO |
| H | OCH₂CH₂—OCH₃ | —(CH₂)₄— | N | CO |
| H | OCH₂CH₂—OC₂H₅ | —(CH₂)₄— | N | CO |
| H | O(CH₂CH₂O)₂—OC₂H₅ | —(CH₂)₄— | N | CO |
| H | S—C₃H₇-n | —(CH₂)₄— | N | CO |
| H | S—C₂H₅ | —(CH₂)₄— | N | CO |
| H | S—CH₃ | —(CH₂)₄— | N | CO |
| H | S—CH₂COOC₂H₅ | —(CH₂)₄— | N | CO |
| H | SCH₂CH₂—COOC₂H₅ | —(CH₂)₄— | N | CO |
| H | O—CH₃C≡C—CH₃ | —(CH₂)₄— | N | CO |
| H | OCH₂—CH=CH—Cl | —(CH₂)₄— | N | CO |
| H | O—CH(CH₃)C≡CH | —(CH₂)₄— | N | CO |
| H | OCH(CH₃)C≡C—CH₃ | —(CH₂)₄— | N | CO |
| H | O—CH(CH₃)CH=CH₂ | —(CH₂)₄— | N | CO |
| H | OCH₂CH=CH—CH₃ | —(CH₂)₄— | N | CO |
| H | O—CH₃ | —(CH₂)₄— | N | CO |
| H | O—C₂H₅ | —(CH₂)₄— | N | CO |
| H | O—C₃H₇-n | —(CH₂)₄— | N | CO |
| H | O—C₃H₇-iso | —(CH₂)₄— | N | CO |
| H | O—[cyclobutane ring with COOC₂H₅] | —(CH₂)₄— | N | CO |
| H | —O—[tetrahydrofuran ring, O at 2-position]—O | —(CH₂)₄— | N | CO |
| H | O—CH(CH₂F)₂ | —(CH₂)₄— | N | CO |
| H | O—CH₂—C(CH₃)=CH₂ | —(CH₂)₄— | N | CO |
| H | S—CH₂—[tetrahydrofuran-2-yl ring with O] | —(CH₂)₄— | N | CO |
| H | O—CH₂—[tetrahydropyran-2-yl ring with O] | —(CH₂)₄— | N | CO |
| H | O—[cyclopropane ring with COOC₂H₅] | —(CH₂)₄— | N | CO |
| H | —S—[cyclobutane ring with COOC₂H₅] | —(CH₂)₄— | N | CO |
| H | S—[cyclopropane ring with COOC₂H₅] | —(CH₂)₄— | N | CO |

TABLE 1-continued

Examples of the compounds of the formula (I)

| $R^1$ | $R^2$ | A | E | G |
|---|---|---|---|---|
| H | S—CH₂—COO-cyclopentyl | $-(CH_2)_4-$ | N | CO |
| H | $S-CH_2-COOC_5H_{11}\text{-}n$ | $-(CH_2)_4-$ | N | CO |
| H | O—CH₂-phenyl | $-(CH_2)_4-$ | N | CO |
| H | S—CH₂-phenyl | $-(CH_2)_4-$ | N | CO |
| H | $O-CH_2CH_2-OCH(CH_2F)_2$ | $-(CH_2)_4-$ | N | CO |
| H | $S-CH(CH_3)_2$ | $-(CH_2)_4-$ | N | CO |
| H | $O-CH_2-CCl=CH_2$ | $-(CH_2)_4-$ | N | CO |
| H | O-phenyl | $-(CH_2)_4-$ | N | CO |
| H | $O-CH_2CN$ | $-(CH_2)_4-$ | N | CO |
| H | $O-CH_2COOC_2H_4-OCH_3$ | $-(CH_2)_4-$ | N | CO |
| H | $O-CH_2-COO-CH(CH_3)COOC_2H_5$ | $-(CH_2)_4-$ | N | CO |
| H | $OCH_2-COOCH_2-COOC_2H_5$ | $-(CH_2)_4-$ | N | CO |
| H | $O-CHF_2$ | $-(CH_2)_4-$ | N | CO |
| H | $O-CH_2CH_2-OCH_2CF_3$ | $-(CH_2)_4-$ | N | CO |
| H | $NHCH_3$ | $-(CH_2)_4-$ | N | CO |
| H | $NHC_2H_5$ | $-(CH_2)_4-$ | N | CO |
| H | $N(CH_3)_2$ | $-(CH_2)_4-$ | N | CO |
| H | $NH-CH_2-COOC_2H_5$ | $-(CH_2)_4-$ | N | CO |
| H | piperidin-1-yl | $-(CH_2)_4-$ | N | CO |
| H | morpholin-4-yl | $-(CH_2)_4-$ | N | CO |
| H | $NH-SO_2CH_3$ | $-(CH_2)_4-$ | N | CO |
| H | $NH-SO_2C_2H_5$ | $-(CH_2)_4-$ | N | CO |
| H | $NH-SO_2C_3H_7\text{-}n$ | $-(CH_2)_4-$ | N | CO |
| H | $NH-SO_2C_3H_7\text{-}i$ | $-(CH_2)_4-$ | N | CO |
| H | $NH-SO_2C_4H_9\text{-}n$ | $-(CH_2)_4-$ | N | CO |
| H | $NH-SO_2C_8H_{17}\text{-}n$ | $-(CH_2)_4-$ | N | CO |
| H | $NH-COCH_3$ | $-(CH_2)_4-$ | N | CO |
| H | $NH-COC_2H_5$ | $-(CH_2)_4-$ | N | CO |
| H | $NH-COCF_3$ | $-(CH_2)_4-$ | N | CO |
| H | $N(CH_3)-SO_2CH_3$ | $-(CH_2)_4-$ | N | CO |
| H | $N(CH_3)-SO_2C_2H_5$ | $-(CH_2)_4-$ | N | CO |
| H | $N(CH_3)-SO_2C_3H_7\text{-}n$ | $-(CH_2)_4-$ | N | CO |
| H | $NH-SO_2CF_3$ | $-(CH_2)_4-$ | N | CO |
| H | $NH-SO_2$-cyclopropyl | $-(CH_2)_4-$ | N | CO |
| H | $NH-SO_2-C_4F_9\text{-}n$ | $-(CH_2)_4-$ | N | CO |
| H | $N(CH_3)SO_2CF_3$ | $-(CH_2)_4-$ | N | CO |
| H | $NH-SO_2$-phenyl | $-(CH_2)_4-$ | N | CO |

TABLE 1-continued

Examples of the compounds of the formula (I)

| R¹ | R² | A | E | G |
|---|---|---|---|---|
| H | NH—SO₂CH₂—[phenyl] | —(CH₂)₄— | N | CO |
| H | N(CH₃)—SO₂—[phenyl]—CH₃ | —(CH₂)₄— | N | CO |
| Cl | OCH₂CF₃ | —(CH₂)₄— | N | CO |
| Cl | OCF₃ | —(CH₂)₄— | N | CO |
| Cl | OCH₂CH(CH₃)—OC₂H₅ | —(CH₂)₄— | N | CO |
| Cl | O—[tetrahydrofuran-2-yl with O—CH₂] | —(CH₂)₄— | N | CO |
| Cl | OCH₂—CH=CH₂ | —(CH₂)₄— | N | CO |
| Cl | OH | —(CH₂)₄— | N | CO |
| Cl | OCH₂—C≡CH | —(CH₂)₄— | N | CO |
| Cl | SCH₂C≡CH | —(CH₂)₄— | N | CO |
| Cl | OCH₂COOC₂H₅ | —(CH₂)₄— | N | CO |
| Cl | S—C(CH₃)₃ | —(CH₂)₄— | N | CO |
| Cl | OCH₂—COOC₅H₁₁-n | —(CH₂)₄— | N | CO |
| Cl | OCH(CH₃)—COOC₂H₅ | —(CH₂)₄— | N | CO |
| Cl | OCH₂CH₂—OCH₃ | —(CH₂)₄— | N | CO |
| Cl | OCH₂CH₂—OC₂H₅ | —(CH₂)₄— | N | CO |
| Cl | O(CH₂CH₂O)₂—OC₂H₅ | —(CH₂)₄— | N | CO |
| Cl | S—C₃H₇-n | —(CH₂)₄— | N | CO |
| Cl | S—C₂H₅ | —(CH₂)₄— | N | CO |
| Cl | S—CH₃ | —(CH₂)₄— | N | CO |
| Cl | S—CH₂COOC₂H₅ | —(CH₂)₄— | N | CO |
| Cl | SCH₂CH₂—COOC₂H₅ | —(CH₂)₄— | N | CO |
| Cl | O—CH₂—C≡C—CH₃ | —(CH₂)₄— | N | CO |
| Cl | OCH₂—CH=CH—Cl | —(CH₂)₄— | N | CO |
| Cl | O—CH(CH₃)C≡CH | —(CH₂)₄— | N | CO |
| Cl | OCH(CH₃)C≡C—CH₃ | —(CH₂)₄— | N | CO |
| Cl | O—CH(CH₃)CH=CH₂ | —(CH₂)₄— | N | CO |
| Cl | OCH₂CH=CH—CH₃ | —(CH₂)₄— | N | CO |
| Cl | O—CH₃ | —(CH₂)₄— | N | CO |
| Cl | O—C₂H₅ | —(CH₂)₄— | N | CO |
| Cl | O—C₃H₇-n | —(CH₂)₄— | N | CO |
| Cl | O—C₃H₇-iso | —(CH₂)₄— | N | CO |
| Cl | O—[cyclobutyl]—COOC₂H₅ | —(CH₂)₄— | N | CO |
| Cl | —O—[tetrahydrofuran-3-yl] | —(CH₂)₄— | N | CO |
| Cl | O—CH(CH₂F)₂ | —(CH₂)₄— | N | CO |
| Cl | O—CH₂—C(CH₃)=CH₂ | —(CH₂)₄— | N | CO |
| Cl | S—CH₂—[tetrahydrofuran-2-yl] | —(CH₂)₄— | N | CO |
| Cl | O—CH₂—[tetrahydropyran-2-yl] | —(CH₂)₄— | N | CO |

TABLE 1-continued

Examples of the compounds of the formula (I)

| R¹ | R² | A | E | G |
|---|---|---|---|---|
| Cl |  | $-(CH_2)_4-$ | N | CO |
| Cl | 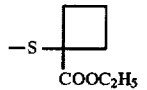 | $-(CH_2)_4-$ | N | CO |
| Cl |  | $-(CH_2)_4-$ | N | CO |
| Cl | 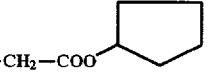 | $-(CH_2)_4-$ | N | CO |
| Cl | $S-CH_2-COOC_5H_{11}$-n | $-(CH_2)_4-$ | N | CO |
| Cl | 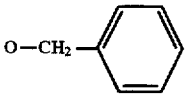 | $-(CH_2)_4-$ | N | CO |
| Cl | 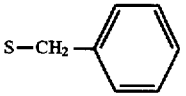 | $-(CH_2)_4-$ | N | CO |
| Cl | $O-CH_2CH_2-OCH(CH_2F)_2$ | $-(CH_2)_4-$ | N | CO |
| Cl | $S-CH(CH_3)_2$ | $-(CH_2)_4-$ | N | CO |
| Cl | $O-CH_2-CCl=CH_2$ | $-(CH_2)_4-$ | N | CO |
| Cl | 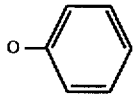 | $-(CH_2)_4-$ | N | CO |
| Cl | $O-CH_2CN$ | $-(CH_2)_4-$ | N | CO |
| Cl | $O-CH_2COOC_2H_4-OCH_3$ | $-(CH_2)_4-$ | N | CO |
| Cl | $O-CH_2-COO-CH(CH_3)COOC_2H_5$ | $-(CH_2)_4-$ | N | CO |
| Cl | $OCH_2COOCH_2-COOC_2H_5$ | $-(CH_2)_4-$ | N | CO |
| Cl | $O-CHF_2$ | $-(CH_2)_4-$ | N | CO |
| Cl | $O-CH_2CH_2-OCH_2CF_3$ | $-(CH_2)_4-$ | N | CO |
| Cl | $NHCH_3$ | $-(CH_2)_4-$ | N | CO |
| Cl | $NHC_2H_5$ | $-(CH_2)_4-$ | N | CO |
| Cl | $N(CH_3)_2$ | $-(CH_2)_4-$ | N | CO |
| Cl | $NH-CH_2-COOC_2H_5$ | $-(CH_2)_4-$ | N | CO |
| Cl |  | $-(CH_2)_4-$ | N | CO |
| Cl |  | $-(CH_2)_4-$ | N | CO |
| Cl | $NH-SO_2CH_3$ | $-(CH_2)_4-$ | N | CO |
| Cl | $NH-SO_2C_2H_5$ | $-(CH_2)_4-$ | N | CO |
| Cl | $NH-SO_2C_3H_7$-n | $-(CH_2)_4-$ | N | CO |
| Cl | $NH-SO_2C_3H_7$-i | $-(CH_2)_4-$ | N | CO |
| Cl | $NH-SO_2C_4H_9$-n | $-(CH_2)_4-$ | N | CO |
| Cl | $NH-SO_2C_8H_{17}$-n | $-(CH_2)_4-$ | N | CO |
| Cl | $NH-COCH_3$ | $-(CH_2)_4-$ | N | CO |
| Cl | $NH-COC_2H_5$ | $-(CH_2)_4-$ | N | CO |
| Cl | $NH-COCF_3$ | $-(CH_2)_4-$ | N | CO |
| Cl | $N(CH_3)-SO_2CH_3$ | $-(CH_2)_4-$ | N | CO |
| Cl | $N(CH_3)-SO_2C_2H_5$ | $-(CH_2)_4-$ | N | CO |
| Cl | $N(CH_3)-SO_2C_3H_7$-n | $-(CH_2)_4-$ | N | CO |

TABLE 1-continued

Examples of the compounds of the formula (I)

| R¹ | R² | A | E | G |
|---|---|---|---|---|
| Cl | NH—SO$_2$CF$_3$ | —(CH$_2$)$_4$— | N | CO |
| Cl | NH—SO$_2$—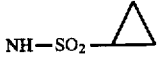 | —(CH$_2$)$_4$— | N | CO |
| Cl | NH—SO$_2$—C$_4$F$_9$-n | —(CH$_2$)$_4$— | N | CO |
| Cl | N(CH$_3$)SO$_2$CF$_3$ | —(CH$_2$)$_4$— | N | CO |
| Cl | NH—SO$_2$—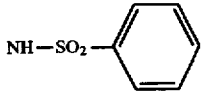 | —(CH$_2$)$_4$— | N | CO |
| Cl | NH—SO$_2$CH$_2$— | —(CH$_2$)$_4$— | N | CO |
| Cl | N(CH$_3$)—SO$_2$——CH$_3$ | —(CH$_2$)$_4$— | N | CO |
| F | O—CH(CH$_2$F)$_2$ | —(CH$_2$)$_4$— | N | CO |
| F | O—CH$_2$—C(CH$_3$)=CH$_2$ | —(CH$_2$)$_4$— | N | CO |
| F | S—CH$_2$—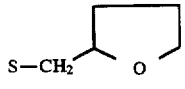 | —(CH$_2$)$_4$— | N | CO |
| F | O—CH$_2$—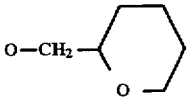 | —(CH$_2$)$_4$— | N | CO |
| F | O——COOC$_2$H$_5$ | —(CH$_2$)$_4$— | N | CO |
| F | —S—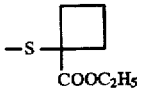—COOC$_2$H$_5$ | —(CH$_2$)$_4$— | N | CO |
| F | S——COOC$_2$H$_5$ | —(CH$_2$)$_4$— | N | CO |
| F | S—CH$_2$—COO—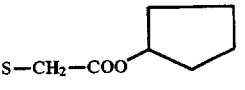 | —(CH$_2$)$_4$— | N | CO |
| F | S—CH$_2$—COOC$_5$H$_{11}$-n | —(CH$_2$)$_4$— | N | CO |
| F | O—CH$_2$—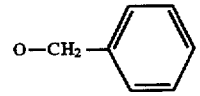 | —(CH$_2$)$_4$— | N | CO |
| F | S—CH$_2$—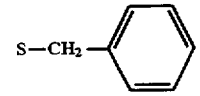 | —(CH$_2$)$_4$— | N | CO |
| F | O—CH$_2$CH$_2$—OCH(CH$_2$F)$_2$ | —(CH$_2$)$_4$— | N | CO |
| F | S—CH(CH$_3$)$_2$ | —(CH$_2$)$_4$— | N | CO |
| F | O—CH$_2$—CCl=CH$_2$ | —(CH$_2$)$_4$— | N | CO |

TABLE 1-continued

Examples of the compounds of the formula (I)

| R¹ | R² | A | E | G |
|---|---|---|---|---|
| F | 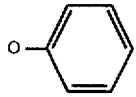 O—⟨phenyl⟩ | —(CH$_2$)$_4$— | N | CO |
| F | O—CH$_2$CN | —(CH$_2$)$_4$— | N | CO |
| F | O—CH$_2$COOC$_2$H$_4$—OCH$_3$ | —(CH$_2$)$_4$— | N | CO |
| F | O—CH$_2$—COO—CH(CH$_3$)COOC$_2$H$_5$ | —(CH$_2$)$_4$— | N | CO |
| F | OCH$_2$—COOCH$_2$—COOC$_2$H$_5$ | —(CH$_2$)$_4$— | N | CO |
| F | O—CHF$_2$ | —(CH$_2$)$_4$— | N | CO |
| F | O—CH$_2$CH$_2$—OCH$_2$CF$_3$ | —(CH$_2$)$_4$— | N | CO |
| F | O—CH(CH$_2$F)$_2$ | —CH$_2$—CH=CH—CH$_2$— | N | CO |
| F | O—CH$_2$—C(CH$_3$)=CH$_2$ | —CH$_2$—CH=CH—CH$_2$— | N | CO |
| F | 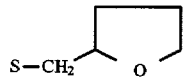 S—CH$_2$—(tetrahydrofuryl) | —CH$_2$—CH=CH—CH$_2$— | N | CO |
| F | 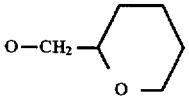 O—CH$_2$—(tetrahydropyranyl) | —CH$_2$—CH=CH—CH$_2$— | N | CO |
| F |  O—(cyclopropyl)COOC$_2$H$_5$ | —CH$_2$—CH=CH—CH$_2$— | N | CO |
| F | 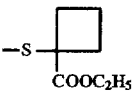 —S—(cyclobutyl)COOC$_2$H$_5$ | —CH$_2$—CH=CH—CH$_2$— | N | CO |
| F | 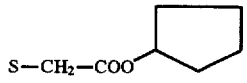 S—(cyclopropyl)COOC$_2$H$_5$ | —CH$_2$—CH=CH—CH$_2$— | N | CO |
| F | 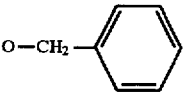 S—CH$_2$—COO—(cyclopentyl) | —CH$_2$—CH=CH—CH$_2$— | N | CO |
| F | S—CH$_2$—COOC$_5$H$_{11}$-n | —CH$_2$—CH=CH—CH$_2$— | N | CO |
| F | 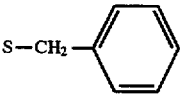 O—CH$_2$—⟨phenyl⟩ | —CH$_2$—CH=CH—CH$_2$— | N | CO |
| F | 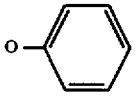 S—CH$_2$—⟨phenyl⟩ | —CH$_2$—CH=CH—CH$_2$— | N | CO |
| F | O—CH$_2$CH$_2$—OCH(CH$_2$F)$_2$ | —CH$_2$—CH=CH—CH$_2$— | N | CO |
| F | S—CH(CH$_3$)$_2$ | —CH$_2$—CH=CH—CH$_2$— | N | CO |
| F | O—CH$_2$—CCl=CH$_2$ | —CH$_2$—CH=CH—CH$_2$— | N | CO |
| F | O—⟨phenyl⟩ | —CH$_2$—CH=CH—CH$_2$— | N | CO |
| F | O—CH$_2$CN | —CH$_2$—CH=CH—CH$_2$— | N | CO |
| F | O—CH$_2$COOC$_2$H$_4$—OCH$_3$ | —CH$_2$—CH=CH—CH$_2$— | N | CO |
| F | O—CH$_2$—COO—CH(CH$_3$)COOC$_2$H$_5$ | —CH$_2$—CH=CH—CH$_2$— | N | CO |
| F | OCH$_2$—COOCH$_2$—COOC$_2$H$_5$ | —CH$_2$—CH=CH—CH$_2$— | N | CO |
| F | O—CHF$_2$ | —CH$_2$—CH=CH—CH$_2$— | N | CO |
| F | O—CH$_2$CH$_2$—OCH$_2$CF$_3$ | —CH$_2$—CH=CH—CH$_2$— | N | CO |
| F | OCH$_2$CF$_3$ | —CH$_2$—CH=CH—CH$_2$— | N | CO |
| F | OCF$_3$ | —CH$_2$—CH=CH—CH$_2$— | N | CO |
| F | OCH$_2$CH(CH$_3$)—OC$_2$H$_5$ | —CH$_2$—CH=CH—CH$_2$— | N | CO |

TABLE 1-continued

Examples of the compounds of the formula (I)

| $R^1$ | $R^2$ | A | E | G |
|---|---|---|---|---|
| F | (tetrahydrofuran-2-yl with O—CH₂) | $-CH_2-CH=CH-CH_2-$ | N | CO |
| F | $OCH_2-CH=CH_2$ | $-CH_2-CH=CH-CH_2-$ | N | CO |
| F | OH | $-CH_2-CH=CH-CH_2-$ | N | CO |
| F | $OCH_2-C\equiv CH$ | $-CH_2-CH=CH-CH_2-$ | N | CO |
| F | $SCH_2C\equiv CH$ | $-CH_2-CH=CH-CH_2-$ | N | CO |
| F | $OCH_2COOC_2H_5$ | $-CH_2-CH=CH-CH_2-$ | N | CO |
| F | $S-C(CH_3)_3$ | $-CH_2-CH=CH-CH_2-$ | N | CO |
| F | $OCH_2-COOC_5H_{11}$-n | $-CH_2-CH=CH-CH_2-$ | N | CO |
| F | $OCH(CH_3)-COOC_2H_5$ | $-CH_2-CH=CH-CH_2-$ | N | CO |
| F | $OCH_2CH_2-OCH_3$ | $-CH_2-CH=CH-CH_2-$ | N | CO |
| F | $OCH_2CH_2-OC_2H_5$ | $-CH_2-CH=CH-CH_2-$ | N | CO |
| F | $O(CH_2CH_2O)_2-OC_2H_5$ | $-CH_2-CH=CH-CH_2-$ | N | CO |
| F | $S-C_3H_7$-n | $-CH_2-CH=CH-CH_2-$ | N | CO |
| F | $S-C_2H_5$ | $-CH_2-CH=CH-CH_2-$ | N | CO |
| F | $S-CH_3$ | $-CH_2-CH=CH-CH_2-$ | N | CO |
| F | $S-CH_2COOC_2H_5$ | $-CH_2-CH=CH-CH_2-$ | N | CO |
| F | $SCH_2CH_2-COOC_2H_5$ | $-CH_2-CH=CH-CH_2-$ | N | CO |
| F | $O-CH_2-C\equiv C-CH_3$ | $-CH_2-CH=CH-CH_2-$ | N | CO |
| F | $OCH_2-CH=CH-Cl$ | $-CH_2-CH=CH-CH_2-$ | N | CO |
| F | $O-CH(CH_3)C\equiv CH$ | $-CH_2-CH=CH-CH_2-$ | N | CO |
| F | $OCH(CH_3)C\equiv C-CH_3$ | $-CH_2-CH=CH-CH_2-$ | N | CO |
| F | $O-CH(CH_3)CH=CH_2$ | $-CH_2-CH=CH-CH_2-$ | N | CO |
| F | $OCH_2CH=CH-CH_3$ | $-CH_2-CH=CH-CH_2-$ | N | CO |
| F | $O-CH_3$ | $-CH_2-CH=CH-CH_2-$ | N | CO |
| F | $O-C_2H_5$ | $-CH_2-CH=CH-CH_2-$ | N | CO |
| F | $O-C_3H_7$-n | $-CH_2-CH=CH-CH_2-$ | N | CO |
| F | $O-C_3H_7$-iso | $-CH_2-CH=CH-CH_2-$ | N | CO |
| F | (oxetane with O— and COOC₂H₅) | $-CH_2-CH=CH-CH_2-$ | N | CO |
| F | (tetrahydrofuran-3-yl with —O—) | $-CH_2-CH=CH-CH_2-$ | N | CO |
| F | $NHCH_3$ | $-CH_2-CH=CH-CH_2-$ | N | CO |
| F | $NHC_2H_5$ | $-CH_2-CH=CH-CH_2-$ | N | CO |
| F | $N(CH_3)_2$ | $-CH_2-CH=CH-CH_2-$ | N | CO |
| F | $NH-CH_2-COOC_2H_5$ | $-CH_2-CH=CH-CH_2-$ | N | CO |
| F | (piperidin-1-yl) | $-CH_2-CH=CH-CH_2-$ | N | CO |
| F | (morpholin-4-yl) | $-CH_2-CH=CH-CH_2-$ | N | CO |
| F | $NH-SO_2CH_3$ | $-CH_2-CH=CH-CH_2-$ | N | CO |
| F | $NH-SO_2C_2H_5$ | $-CH_2-CH=CH-CH_2-$ | N | CO |
| F | $NH-SO_2C_3H_7$-n | $-CH_2-CH=CH-CH_2-$ | N | CO |
| F | $NH-SO_2C_3H_7$-i | $-CH_2-CH=CH-CH_2-$ | N | CO |
| F | $NH-SO_2C_4H_9$-n | $-CH_2-CH=CH-CH_2-$ | N | CO |
| F | $NH-SO_2C_8H_{17}$-n | $-CH_2-CH=CH-CH_2-$ | N | CO |
| F | $NH-COCH_3$ | $-CH_2-CH=CH-CH_2-$ | N | CO |
| F | $NH-COC_2H_5$ | $-CH_2-CH=CH-CH_2-$ | N | CO |
| F | $NH-COCF_3$ | $-CH_2-CH=CH-CH_2-$ | N | CO |
| F | $N(CH_3)-SO_2CH_3$ | $-CH_2-CH=CH-CH_2-$ | N | CO |
| F | $N(CH_3)-SO_2C_2H_5$ | $-CH_2-CH=CH-CH_2-$ | N | CO |
| F | $N(CH_3)-SO_2C_3H_7$-n | $-CH_2-CH=CH-CH_2-$ | N | CO |
| F | $NH-SO_2CF_3$ | $-CH_2-CH=CH-CH_2-$ | N | CO |

TABLE 1-continued

Examples of the compounds of the formula (I)

| R¹ | R² | A | E | G |
|---|---|---|---|---|
| F | NH—SO₂—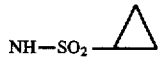 | —CH₂—CH=CH—CH₂— | N | CO |
| F | NH—SO₂—C₄F₉-n | —CH₂—CH=CH—CH₂— | N | CO |
| F | N(CH₃)SO₂CF₃ | —CH₂—CH=CH—CH₂— | N | CO |
| F | NH—SO₂—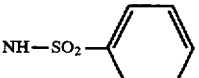 | —CH₂—CH=CH—CH₂— | N | CO |
| F | NH—SO₂CH₂—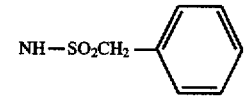 | —CH₂—CH=CH—CH₂— | N | CO |
| F | N(CH₃)—SO₂—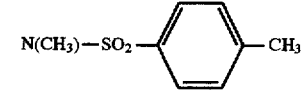—CH₃ | —CH₂—CH=CH—CH₂— | N | CO |
| H | OCH₂CF₃ | —CH₂—CH=CH—CH₂— | N | CO |
| H | OCF₃ | —CH₂—CH=CH—CH₂— | N | CO |
| H | OCH₂CH(CH₃)—OC₂H₅ | —CH₂—CH=CH—CH₂— | N | CO |
| H | 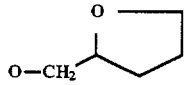 | —CH₂—CH=CH—CH₂— | N | CO |
| H | OCH₂—CH=CH₂ | —CH₂—CH=CH—CH₂— | N | CO |
| H | OH | —CH₂—CH=CH—CH₂— | N | CO |
| H | OCH₂—C≡CH | —CH₂—CH=CH—CH₂— | N | CO |
| H | SCH₂C≡CH | —CH₂—CH=CH—CH₂— | N | CO |
| H | OCH₂COOC₂H₅ | —CH₂—CH=CH—CH₂— | N | CO |
| H | S—C(CH₃)₃ | —CH₂—CH=CH—CH₂— | N | CO |
| H | OCH₂—COOC₅H₁₁-n | —CH₂—CH=CH—CH₂— | N | CO |
| H | OCH(CH₃)—COOC₂H₅ | —CH₂—CH=CH—CH₂— | N | CO |
| H | OCH₂CH₂—OCH₃ | —CH₂—CH=CH—CH₂— | N | CO |
| H | OCH₂CH₂—OC₂H₅ | —CH₂—CH=CH—CH₂— | N | CO |
| H | O(CH₂CH₂O)₂—OC₂H₅ | —CH₂—CH=CH—CH₂— | N | CO |
| H | S—C₃H₇-n | —CH₂—CH=CH—CH₂— | N | CO |
| H | S—C₂H₅ | —CH₂—CH=CH—CH₂— | N | CO |
| H | S—CH₃ | —CH₂—CH=CH—CH₂— | N | CO |
| H | S—CH₂COOC₂H₅ | —CH₂—CH=CH—CH₂— | N | CO |
| H | SCH₂CH₂—COOC₂H₅ | —CH₂—CH=CH—CH₂— | N | CO |
| H | O—CH₂—C≡C—CH₃ | —CH₂—CH=CH—CH₂— | N | CO |
| H | OCH₂—CH=CH—Cl | —CH₂—CH=CH—CH₂— | N | CO |
| H | O—CH(CH₃)C≡CH | —CH₂—CH=CH—CH₂— | N | CO |
| H | OCH(CH₃)C≡C—CH₃ | —CH₂—CH=CH—CH₂— | N | CO |
| H | O—CH(CH₃)CH=CH₂ | —CH₂—CH=CH—CH₂— | N | CO |
| H | OCH₂CH=CH—CH₃ | —CH₂—CH=CH—CH₂— | N | CO |
| H | O—CH₃ | —CH₂—CH=CH—CH₂— | N | CO |
| H | O—C₂H₅ | —CH₂—CH=CH—CH₂— | N | CO |
| H | O—C₃H₇-n | —CH₂—CH=CH—CH₂— | N | CO |
| H | O—C₃H₇-iso | —CH₂—CH=CH—CH₂— | N | CO |
| H | 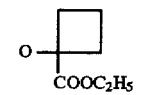 | —CH₂—CH=CH—CH₂— | N | CO |
| H | 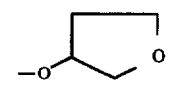 | —CH₂—CH=CH—CH₂— | N | CO |
| H | O—CH(CH₂F)₂ | —CH₂—CH=CH—CH₂— | N | CO |
| H | O—CH₂—C(CH₃)=CH₂ | —CH₂—CH=CH—CH₂— | N | CO |

TABLE 1-continued

Examples of the compounds of the formula (I)

| $R^1$ | $R^2$ | A | E | G |
|---|---|---|---|---|
| H | S—CH$_2$-(tetrahydrofuran-2-yl, O) | —CH$_2$—CH=CH—CH$_2$— | N | CO |
| H | O—CH$_2$-(tetrahydropyran-2-yl, O) | —CH$_2$—CH=CH—CH$_2$— | N | CO |
| H | O-(cyclopropyl-COOC$_2$H$_5$) | —CH$_2$—CH=CH—CH$_2$— | N | CO |
| H | —S-(cyclobutyl-COOC$_2$H$_5$) | —CH$_2$—CH=CH—CH$_2$— | N | CO |
| H | S-(cyclopropyl-COOC$_2$H$_5$) | —CH$_2$—CH=CH—CH$_2$— | N | CO |
| H | S—CH$_2$—COO-(cyclopentyl) | —CH$_2$—CH=CH—CH$_2$— | N | CO |
| H | S—CH$_2$—COOC$_5$H$_{11}$-n | —CH$_2$—CH=CH—CH$_2$— | N | CO |
| H | O—CH$_2$-phenyl | —CH$_2$—CH=CH—CH$_2$— | N | CO |
| H | S—CH$_2$-phenyl | —CH$_2$—CH=CH—CH$_2$— | N | CO |
| H | O—CH$_2$CH$_2$—OCH(CH$_2$F)$_2$ | —CH$_2$—CH=CH—CH$_2$— | N | CO |
| H | S—CH(CH$_3$)$_2$ | —CH$_2$—CH=CH—CH$_2$— | N | CO |
| H | O—CH$_2$—CCl=CH$_2$ | —CH$_2$—CH=CH—CH$_2$— | N | CO |
| H | O-phenyl | —CH$_2$—CH=CH—CH$_2$— | N | CO |
| H | O—CH$_2$CN | —CH$_2$—CH=CH—CH$_2$— | N | CO |
| H | O—CH$_2$COOC$_2$H$_4$—OCH$_3$ | —CH$_2$—CH=CH—CH$_2$— | N | CO |
| H | O—CH$_2$—COO—CH(CH$_3$)COOC$_2$H$_5$ | —CH$_2$—CH=CH—CH$_2$— | N | CO |
| H | OCH$_2$—COOCH$_2$—COOC$_2$H$_5$ | —CH$_2$—CH=CH—CH$_2$— | N | CO |
| H | O—CHF$_2$ | —CH$_2$—CH=CH—CH$_2$— | N | CO |
| H | O—CH$_2$CH$_2$—OCH$_2$CF$_3$ | —CH$_2$—CH=CH—CH$_2$— | N | CO |
| H | NHCH$_3$ | —CH$_2$—CH=CH—CH$_2$— | N | CO |
| H | NHC$_2$H$_5$ | —CH$_2$—CH=CH—CH$_2$— | N | CO |
| H | N(CH$_3$)$_2$ | —CH$_2$—CH=CH—CH$_2$— | N | CO |
| H | NH—CH$_2$—COOC$_2$H$_5$ | —CH$_2$—CH=CH—CH$_2$— | N | CO |
| H | piperidin-1-yl | —CH$_2$—CH=CH—CH$_2$— | N | CO |
| H | morpholin-4-yl | —CH$_2$—CH=CH—CH$_2$— | N | CO |
| H | NH—SO$_2$CH$_3$ | —CH$_2$—CH=CH—CH$_2$— | N | CO |

TABLE 1-continued

Examples of the compounds of the formula (I)

| R¹ | R² | A | E | G |
|---|---|---|---|---|
| H | NH—SO$_2$C$_2$H$_5$ | —CH$_2$—CH=CH—CH$_2$— | N | CO |
| H | NH—SO$_2$C$_3$H$_7$-n | —CH$_2$—CH=CH—CH$_2$— | N | CO |
| H | NH—SO$_2$C$_3$H$_7$-i | —CH$_2$—CH=CH—CH$_2$— | N | CO |
| H | NH—SO$_2$C$_4$H$_9$-n | —CH$_2$—CH=CH—CH$_2$— | N | CO |
| H | NH—SO$_2$C$_8$H$_{17}$-n | —CH$_2$—CH=CH—CH$_2$— | N | CO |
| H | NH—COCH$_3$ | —CH$_2$—CH=CH—CH$_2$— | N | CO |
| H | NH—COC$_2$H$_5$ | —CH$_2$—CH=CH—CH$_2$— | N | CO |
| H | NH—COCF$_3$ | —CH$_2$—CH=CH—CH$_2$— | N | CO |
| H | N(CH$_3$)—SO$_2$CH$_3$ | —CH$_2$—CH=CH—CH$_2$— | N | CO |
| H | N(CH$_3$)—SO$_2$C$_2$H$_5$ | —CH$_2$—CH=CH—CH$_2$— | N | CO |
| H | N(CH$_3$)—SO$_2$C$_3$H$_7$-n | —CH$_2$—CH=CH—CH$_2$— | N | CO |
| H | NH—SO$_2$CF$_3$ | —CH$_2$—CH=CH—CH$_2$— | N | CO |
| H | NH—SO$_2$—△ (cyclopropyl) | —CH$_2$—CH=CH—CH$_2$— | N | CO |
| H | NH—SO$_2$—C$_4$F$_9$-n | —CH$_2$—CH=CH—CH$_2$— | N | CO |
| H | N(CH$_3$)SO$_2$CF$_3$ | —CH$_2$—CH=CH—CH$_2$— | N | CO |
| H | NH—SO$_2$—(phenyl) | —CH$_2$—CH=CH—CH$_2$— | N | CO |
| H | NH—SO$_2$CH$_2$—(phenyl) | —CH$_2$—CH=CH—CH$_2$— | N | CO |
| H | N(CH$_3$)—SO$_2$—(phenyl)—CH$_3$ | —CH$_2$—CH=CH—CH$_2$— | N | CO |
| Cl | OCH$_2$CF$_3$ | —CH$_2$—CH=CH—CH$_2$— | N | CO |
| Cl | OCF$_3$ | —CH$_2$—CH=CH—CH$_2$— | N | CO |
| Cl | OCH$_2$CH(CH$_3$)—OC$_2$H$_5$ | —CH$_2$—CH=CH—CH$_2$— | N | CO |
| Cl | (1,3-dioxolan-2-yl-methyl) | —CH$_2$—CH=CH—CH$_2$— | N | CO |
| Cl | OCH$_2$—CH=CH$_2$ | —CH$_2$—CH=CH—CH$_2$— | N | CO |
| Cl | OH | —CH$_2$—CH=CH—CH$_2$— | N | CO |
| Cl | OCH$_2$—C≡CH | —CH$_2$—CH=CH—CH$_2$— | N | CO |
| Cl | SCH$_2$C≡CH | —CH$_2$—CH=CH—CH$_2$— | N | CO |
| Cl | OCH$_2$COOC$_2$H$_5$ | —CH$_2$—CH=CH—CH$_2$— | N | CO |
| Cl | S—C(CH$_3$)$_3$ | —CH$_2$—CH=CH—CH$_2$— | N | CO |
| Cl | OCH$_2$—COOC$_5$H$_{11}$-n | —CH$_2$—CH=CH—CH$_2$— | N | CO |
| Cl | OCH(CH$_3$)—COOC$_2$H$_5$ | —CH$_2$—CH=CH—CH$_2$— | N | CO |
| Cl | OCH$_2$CH$_2$—OCH$_3$ | —CH$_2$—CH=CH—CH$_2$— | N | CO |
| Cl | OCH$_2$CH$_2$—OC$_2$H$_5$ | —CH$_2$—CH=CH—CH$_2$— | N | CO |
| Cl | O(CH$_2$CH$_2$O)$_2$—OC$_2$H$_5$ | —CH$_2$—CH=CH—CH$_2$— | N | CO |
| Cl | S—C$_3$H$_7$-n | —CH$_2$—CH=CH—CH$_2$— | N | CO |
| Cl | S—C$_2$H$_5$ | —CH$_2$—CH=CH—CH$_2$— | N | CO |
| Cl | S—CH$_3$ | —CH$_2$—CH=CH—CH$_2$— | N | CO |
| Cl | S—CH$_2$COOC$_2$H$_5$ | —CH$_2$—CH=CH—CH$_2$— | N | CO |
| Cl | SCH$_2$CH$_2$—COOC$_2$H$_5$ | —CH$_2$—CH=CH—CH$_2$— | N | CO |
| Cl | O—CH$_2$—C≡C—CH$_3$ | —CH$_2$—CH=CH—CH$_2$— | N | CO |
| Cl | OCH$_2$—CH=CH—Cl | —CH$_2$—CH=CH—CH$_2$— | N | CO |
| Cl | O—CH(CH$_3$)C≡CH | —CH$_2$—CH=CH—CH$_2$— | N | CO |
| Cl | OCH(CH$_3$)C≡C—CH$_3$ | —CH$_2$—CH=CH—CH$_2$— | N | CO |
| Cl | O—CH(CH$_3$)CH=CH$_2$ | —CH$_2$—CH=CH—CH$_2$— | N | CO |
| Cl | OCH$_2$CH=CH—CH$_3$ | —CH$_2$—CH=CH—CH$_2$— | N | CO |
| Cl | O—CH$_3$ | —CH$_2$—CH=CH—CH$_2$— | N | CO |
| Cl | O—C$_2$H$_5$ | —CH$_2$—CH=CH—CH$_2$— | N | CO |
| Cl | O—C$_3$H$_7$-n | —CH$_2$—CH=CH—CH$_2$— | N | CO |
| Cl | O—C$_3$H$_7$-iso | —CH$_2$—CH=CH—CH$_2$— | N | CO |

TABLE 1-continued

Examples of the compounds of the formula (I)

| $R^1$ | $R^2$ | A | E | G |
|---|---|---|---|---|
| Cl | cyclobutane with O– and COOC$_2$H$_5$ substituents | –CH$_2$–CH=CH–CH$_2$– | N | CO |
| Cl | tetrahydrofuran with –O–CH$_2$– linkage | –CH$_2$–CH=CH–CH$_2$– | N | CO |
| Cl | O–CH(CH$_2$F)$_2$ | –CH$_2$–CH=CH–CH$_2$– | N | CO |
| Cl | O–CH$_2$–C(CH$_3$)=CH$_2$ | –CH$_2$–CH=CH–CH$_2$– | N | CO |
| Cl | tetrahydrofuran with S–CH$_2$– linkage | –CH$_2$–CH=CH–CH$_2$– | N | CO |
| Cl | tetrahydropyran with O–CH$_2$– linkage | –CH$_2$–CH=CH–CH$_2$– | N | CO |
| Cl | cyclopropane with O– and COOC$_2$H$_5$ substituents | –CH$_2$–CH=CH–CH$_2$– | N | CO |
| Cl | cyclobutane with –S– and COOC$_2$H$_5$ substituents | –CH$_2$–CH=CH–CH$_2$– | N | CO |
| Cl | cyclopropane with S– and COOC$_2$H$_5$ substituents | –CH$_2$–CH=CH–CH$_2$– | N | CO |
| Cl | S–CH$_2$–COO–cyclopentyl | –CH$_2$–CH=CH–CH$_2$– | N | CO |
| Cl | S–CH$_2$–COOC$_5$H$_{11}$-n | –CH$_2$–CH=CH–CH$_2$– | N | CO |
| Cl | O–CH$_2$–phenyl | –CH$_2$–CH=CH–CH$_2$– | N | CO |
| Cl | S–CH$_2$–phenyl | –CH$_2$–CH=CH–CH$_2$– | N | CO |
| Cl | O–CH$_2$CH$_2$–OCH(CH$_2$F)$_2$ | –CH$_2$–CH=CH–CH$_2$– | N | CO |
| Cl | S–CH(CH$_3$)$_2$ | –CH$_2$–CH=CH–CH$_2$– | N | CO |
| Cl | O–CH$_2$–CCl=CH$_2$ | –CH$_2$–CH=CH–CH$_2$– | N | CO |
| Cl | O–phenyl | –CH$_2$–CH=CH–CH$_2$– | N | CO |
| Cl | O–CH$_2$CN | –CH$_2$–CH=CH–CH$_2$– | N | CO |
| Cl | O–CH$_2$COOC$_2$H$_4$–OCH$_3$ | –CH$_2$–CH=CH–CH$_2$– | N | CO |
| Cl | O–CH$_2$–COO–CH(CH$_3$)COOC$_2$H$_5$ | –CH$_2$–CH=CH–CH$_2$– | N | CO |
| Cl | OCH$_2$–COOCH$_2$–COOC$_2$H$_5$ | –CH$_2$–CH=CH–CH$_2$– | N | CO |
| Cl | O–CHF$_2$ | –CH$_2$–CH=CH–CH$_2$– | N | CO |
| Cl | O–CH$_2$CH$_2$–OCH$_2$CF$_3$ | –CH$_2$–CH=CH–CH$_2$– | N | CO |
| Cl | NHCH$_3$ | –CH$_2$–CH=CH–CH$_2$– | N | CO |
| Cl | NHC$_2$H$_5$ | –CH$_2$–CH=CH–CH$_2$– | N | CO |
| Cl | N(CH$_3$)$_2$ | –CH$_2$–CH=CH–CH$_2$– | N | CO |
| Cl | NH–CH$_2$–COOC$_2$H$_5$ | –CH$_2$–CH=CH–CH$_2$– | N | CO |

TABLE 1-continued

Examples of the compounds of the formula (I)

| R¹ | R² | A | E | G |
|---|---|---|---|---|
| Cl | 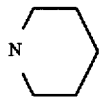 | —CH₂—CH=CH—CH₂— | N | CO |
| Cl | 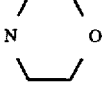 | —CH₂—CH=CH—CH₂— | N | CO |
| Cl | NH—SO₂CH₃ | —CH₂—CH=CH—CH₂— | N | CO |
| Cl | NH—SO₂C₂H₅ | —CH₂—CH=CH—CH₂— | N | CO |
| Cl | NH—SO₂C₃H₇-n | —CH₂—CH=CH—CH₂— | N | CO |
| Cl | NH—SO₂C₃H₇-i | —CH₂—CH=CH—CH₂— | N | CO |
| Cl | NH—SO₂C₄H₉-n | —CH₂—CH=CH—CH₂— | N | CO |
| Cl | NH—SO₂C₈H₁₇-n | —CH₂—CH=CH—CH₂— | N | CO |
| Cl | NH—COCH₃ | —CH₂—CH=CH—CH₂— | N | CO |
| Cl | NH—COC₂H₅ | —CH₂—CH=CH—CH₂— | N | CO |
| Cl | NH—COCF₃ | —CH₂—CH=CH—CH₂— | N | CO |
| Cl | N(CH₃)—SO₂CH₃ | —CH₂—CH=CH—CH₂— | N | CO |
| Cl | N(CH₃)—SO₂C₂H₅ | —CH₂—CH=CH—CH₂— | N | CO |
| Cl | N(CH₃)—SO₂C₃H₇-n | —CH₂—CH=CH—CH₂— | N | CO |
| Cl | NH—SO₂CF₃ | —CH₂—CH=CH—CH₂— | N | CO |
| Cl | 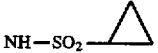 | —CH₂—CH=CH—CH₂— | N | CO |
| Cl | NH—SO₂—C₄F₉-n | —CH₂—CH=CH—CH₂— | N | CO |
| Cl | N(CH₃)SO₂CF₃ | —CH₂—CH=CH—CH₂— | N | CO |
| Cl | 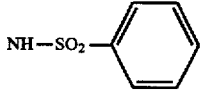 | —CH₂—CH=CH—CH₂— | N | CO |
| Cl | 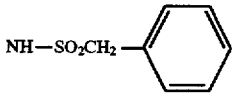 | —CH₂—CH=CH—CH₂— | N | CO |
| Cl | 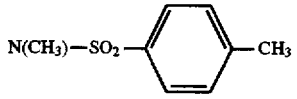 | —CH₂—CH=CH—CH₂— | N | CO |
| F | O—CH(CH₂F)₂ | —(CH₂)₂—CH=CH— | N | CO |
| F | O—CH₂—C(CH₃)=CH₂ | —(CH₂)₂—CH=CH— | N | CO |
| F | 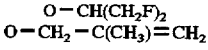 | —(CH₂)₂—CH=CH— | N | CO |
| F |  | —(CH₂)₂—CH=CH— | N | CO |
| F | 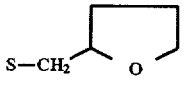 | —(CH₂)₂—CH=CH— | N | CO |
| F | 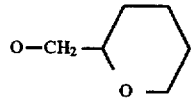 | —(CH₂)₂—CH=CH— | N | CO |
| F | 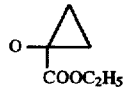 | —(CH₂)₂—CH=CH— | N | CO |

TABLE 1-continued

Examples of the compounds of the formula (I)

| $R^1$ | $R^2$ | A | E | G |
|---|---|---|---|---|
| F | S—CH$_2$—COO—(cyclopentyl) | —(CH$_2$)$_2$—CH=CH— | N | CO |
| F | S—CH$_2$—COOC$_5$H$_{11}$-n | —(CH$_2$)$_2$—CH=CH— | N | CO |
| F | O—CH$_2$—(phenyl) | —(CH$_2$)$_2$—CH=CH— | N | CO |
| F | S—CH$_2$—(phenyl) | —(CH$_2$)$_2$—CH=CH— | N | CO |
| F | O—CH$_2$CH$_2$—OCH(CH$_2$F)$_2$ | —(CH$_2$)$_2$—CH=CH— | N | CO |
| F | S—CH(CH$_3$)$_2$ | —(CH$_2$)$_2$—CH=CH— | N | CO |
| F | O—CH$_2$—CCl=CH$_2$ | —(CH$_2$)$_2$—CH=CH— | N | CO |
| F | O—(phenyl) | —(CH$_2$)$_2$—CH=CH— | N | CO |
| F | O—CH$_2$CN | —(CH$_2$)$_2$—CH=CH— | N | CO |
| F | O—CH$_2$COOC$_2$H$_4$—OCH$_3$ | —(CH$_2$)$_2$—CH=CH— | N | CO |
| F | O—CH$_2$—COO—CH(CH$_3$)COOC$_2$H$_5$ | —(CH$_2$)$_2$—CH=CH— | N | CO |
| F | OCH$_2$—COOCH$_2$—COOC$_2$H$_5$ | —(CH$_2$)$_2$—CH=CH— | N | CO |
| F | O—CHF$_2$ | —(CH$_2$)$_2$—CH=CH— | N | CO |
| F | O—CH$_2$CH$_2$—OCH$_2$CF$_3$ | —(CH$_2$)$_2$—CH=CH— | N | CO |
| F | OCH$_2$CF$_3$ | —(CH$_2$)$_2$—CH=CH— | N | CO |
| F | OCF$_3$ | —(CH$_2$)$_2$—CH=CH— | N | CO |
| F | OCH$_2$CH(CH$_3$)—OC$_2$H$_5$ | —(CH$_2$)$_2$—CH=CH— | N | CO |
| F | O—CH$_2$—(tetrahydrofuran-2-yl via O) | —(CH$_2$)$_2$—CH=CH— | N | CO |
| F | OCH$_2$—CH=CH$_2$ | —(CH$_2$)$_2$—CH=CH— | N | CO |
| F | OH | —(CH$_2$)$_2$—CH=CH— | N | CO |
| F | OCH$_2$—C≡CH | —(CH$_2$)$_2$—CH=CH— | N | CO |
| F | SCH$_2$C≡CH | —(CH$_2$)$_2$—CH=CH— | N | CO |
| F | OCH$_2$COOC$_2$H$_5$ | —(CH$_2$)$_2$—CH=CH— | N | CO |
| F | S—C(CH$_3$)$_3$ | —(CH$_2$)$_2$—CH=CH— | N | CO |
| F | OCH$_2$—COOC$_5$H$_{11}$-n | —(CH$_2$)$_2$—CH=CH— | N | CO |
| F | OCH(CH$_3$)—COOC$_2$H$_5$ | —(CH$_2$)$_2$—CH=CH— | N | CO |
| F | OCH$_2$CH$_2$—OCH$_3$ | —(CH$_2$)$_2$—CH=CH— | N | CO |
| F | OCH$_2$CH$_2$—OC$_2$H$_5$ | —(CH$_2$)$_2$—CH=CH— | N | CO |
| F | O(CH$_2$CH$_2$O)$_2$—OC$_2$H$_5$ | —(CH$_2$)$_2$—CH=CH— | N | CO |
| F | S—C$_3$H$_7$-n | —(CH$_2$)$_2$—CH=CH— | N | CO |
| F | S—C$_2$H$_5$ | —(CH$_2$)$_2$—CH=CH— | N | CO |
| F | S—CH$_3$ | —(CH$_2$)$_2$—CH=CH— | N | CO |
| F | S—CH$_2$COOC$_2$H$_5$ | —(CH$_2$)$_2$—CH=CH— | N | CO |
| F | SCH$_2$CH$_2$—COOC$_2$H$_5$ | —(CH$_2$)$_2$—CH=CH— | N | CO |
| F | O—CH$_2$—C≡C—CH$_3$ | —(CH$_2$)$_2$—CH=CH— | N | CO |
| F | OCH$_2$—CH=CH—Cl | —(CH$_2$)$_2$—CH=CH— | N | CO |
| F | O—CH(CH$_3$)C≡CH | —(CH$_2$)$_2$—CH=CH— | N | CO |
| F | OCH(CH$_3$)C≡C—CH$_3$ | —(CH$_2$)$_2$—CH=CH— | N | CO |
| F | O—CH(CH$_3$)CH=CH$_2$ | —(CH$_2$)$_2$—CH=CH— | N | CO |
| F | OCH$_2$CH=CH—CH$_3$ | —(CH$_2$)$_2$—CH=CH— | N | CO |
| F | O—CH$_3$ | —(CH$_2$)$_2$—CH=CH— | N | CO |
| F | O—C$_2$H$_5$ | —(CH$_2$)$_2$—CH=CH— | N | CO |
| F | O—C$_3$H$_7$-n | —(CH$_2$)$_2$—CH=CH— | N | CO |
| F | O—C$_3$H$_7$-iso | —(CH$_2$)$_2$—CH=CH— | N | CO |

TABLE 1-continued

Examples of the compounds of the formula (I)

| R¹ | R² | A | E | G |
|---|---|---|---|---|
| F | 1-(ethoxycarbonyl)cyclobutyl-O– | –$(CH_2)_2$–CH=CH– | N | CO |
| F | tetrahydrofuran-3-yl-O– | –$(CH_2)_2$–CH=CH– | N | CO |
| F | $NHCH_3$ | –$(CH_2)_2$–CH=CH– | N | CO |
| F | $NHC_2H_5$ | –$(CH_2)_2$–CH=CH– | N | CO |
| F | $N(CH_3)_2$ | –$(CH_2)_2$–CH=CH– | N | CO |
| F | $NH-CH_2-COOC_2H_5$ | –$(CH_2)_2$–CH=CH– | N | CO |
| F | piperidin-1-yl | –$(CH_2)_2$–CH=CH– | N | CO |
| F | morpholin-4-yl | –$(CH_2)_2$–CH=CH– | N | CO |
| F | $NH-SO_2CH_3$ | –$(CH_2)_2$–CH=CH– | N | CO |
| F | $NH-SO_2C_2H_5$ | –$(CH_2)_2$–CH=CH– | N | CO |
| F | $NH-SO_2C_3H_7$-n | –$(CH_2)_2$–CH=CH– | N | CO |
| F | $NH-SO_2C_3H_7$-i | –$(CH_2)_2$–CH=CH– | N | CO |
| F | $NH-SO_2C_4H_9$-n | –$(CH_2)_2$–CH=CH– | N | CO |
| F | $NH-SO_2C_8H_{17}$-n | –$(CH_2)_2$–CH=CH– | N | CO |
| F | $NH-COCH_3$ | –$(CH_2)_2$–CH=CH– | N | CO |
| F | $NH-COC_2H_5$ | –$(CH_2)_2$–CH=CH– | N | CO |
| F | $NH-COCF_3$ | –$(CH_2)_2$–CH=CH– | N | CO |
| F | $N(CH_3)-SO_2CH_3$ | –$(CH_2)_2$–CH=CH– | N | CO |
| F | $N(CH_3)-SO_2C_2H_5$ | –$(CH_2)_2$–CH=CH– | N | CO |
| F | $N(CH_3)-SO_2C_3H_7$-n | –$(CH_2)_2$–CH=CH– | N | CO |
| F | $NH-SO_2CF_3$ | –$(CH_2)_2$–CH=CH– | N | CO |
| F | $NH-SO_2$-cyclopropyl | –$(CH_2)_2$–CH=CH– | N | CO |
| F | $NH-SO_2-C_4F_9$-n | –$(CH_2)_2$–CH=CH– | N | CO |
| F | $N(CH_3)SO_2CF_3$ | –$(CH_2)_2$–CH=CH– | N | CO |
| F | $NH-SO_2$-phenyl | –$(CH_2)_2$–CH=CH– | N | CO |
| F | $NH-SO_2CH_2$-phenyl | –$(CH_2)_2$–CH=CH– | N | CO |
| F | $N(CH_3)-SO_2$-(4-methylphenyl) | –$(CH_2)_2$–CH=CH– | N | CO |
| H | $OCH_2CF_3$ | –$(CH_2)_2$–CH=CH– | N | CO |
| H | $OCF_3$ | –$(CH_2)_2$–CH=CH– | N | CO |
| H | $OCH_2CH(CH_3)-OC_2H_5$ | –$(CH_2)_2$–CH=CH– | N | CO |
| H | (1,3-dioxolan-2-yl)methyl-O– | –$(CH_2)_2$–CH=CH– | N | CO |
| H | $OCH_2-CH=CH_2$ | –$(CH_2)_2$–CH=CH– | N | CO |
| H | $OH$ | –$(CH_2)_2$–CH=CH– | N | CO |
| H | $OCH_2-C\equiv CH$ | –$(CH_2)_2$–CH=CH– | N | CO |

TABLE 1-continued

Examples of the compounds of the formula (I)

| R$^1$ | R$^2$ | A | E | G |
|---|---|---|---|---|
| H | SCH$_2$C≡CH | —(CH$_2$)$_2$—CH=CH— | N | CO |
| H | OCH$_2$COOC$_2$H$_5$ | —(CH$_2$)$_2$—CH=CH— | N | CO |
| H | S—C(CH$_3$)$_3$ | —(CH$_2$)$_2$—CH=CH— | N | CO |
| H | OCH$_2$—COOC$_5$H$_{11}$-n | —(CH$_2$)$_2$—CH=CH— | N | CO |
| H | OCH(CH$_3$)—COOC$_2$H$_5$ | —(CH$_2$)$_2$—CH=CH— | N | CO |
| H | OCH$_2$CH$_2$—OCH$_3$ | —(CH$_2$)$_2$—CH=CH— | N | CO |
| H | OCH$_2$CH$_2$—OC$_2$H$_5$ | —(CH$_2$)$_2$—CH=CH— | N | CO |
| H | O(CH$_2$CH$_2$O)$_2$—OC$_2$H$_5$ | —(CH$_2$)$_2$—CH=CH— | N | CO |
| H | S—C$_3$H$_7$-n | —(CH$_2$)$_2$—CH=CH— | N | CO |
| H | S—C$_2$H$_5$ | —(CH$_2$)$_2$—CH=CH— | N | CO |
| H | S—CH$_3$ | —(CH$_2$)$_2$—CH=CH— | N | CO |
| H | S—CH$_2$COOC$_2$H$_5$ | —(CH$_2$)$_2$—CH=CH— | N | CO |
| H | SCH$_2$CH$_2$—COOC$_2$H$_5$ | —(CH$_2$)$_2$—CH=CH— | N | CO |
| H | O—CH$_2$—C≡C—CH$_3$ | —(CH$_2$)$_2$—CH=CH— | N | CO |
| H | OCH$_2$—CH=CH—Cl | —(CH$_2$)$_2$—CH=CH— | N | CO |
| H | O—CH(CH$_3$)C≡CH | —(CH$_2$)$_2$—CH=CH— | N | CO |
| H | OCH(CH$_3$)C≡C—CH$_3$ | —(CH$_2$)$_2$—CH=CH— | N | CO |
| H | O—CH(CH$_3$)CH=CH$_2$ | —(CH$_2$)$_2$—CH=CH— | N | CO |
| H | OCH$_2$CH=CH—CH$_3$ | —(CH$_2$)$_2$—CH=CH— | N | CO |
| H | O—CH$_3$ | —(CH$_2$)$_2$—CH=CH— | N | CO |
| H | O—C$_2$H$_5$ | —(CH$_2$)$_2$—CH=CH— | N | CO |
| H | O—C$_3$H$_7$-n | —(CH$_2$)$_2$—CH=CH— | N | CO |
| H | O—C$_3$H$_7$-iso | —(CH$_2$)$_2$—CH=CH— | N | CO |
| H | 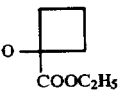 | —(CH$_2$)$_2$—CH=CH— | N | CO |
| H | 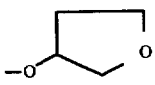 | —(CH$_2$)$_2$—CH=CH— | N | CO |
| H | O—CH(CH$_2$F)$_2$ | —(CH$_2$)$_2$—CH=CH— | N | CO |
| H | O—CH$_2$—C(CH$_3$)=CH$_2$ | —(CH$_2$)$_2$—CH=CH— | N | CO |
| H | 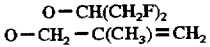 | —(CH$_2$)$_2$—CH=CH— | N | CO |
| H | 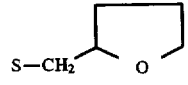 | —(CH$_2$)$_2$—CH=CH— | N | CO |
| H | 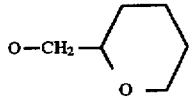 | —(CH$_2$)$_2$—CH=CH— | N | CO |
| H | 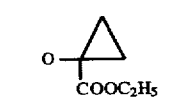 | —(CH$_2$)$_2$—CH=CH— | N | CO |
| H | 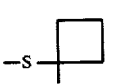 | —(CH$_2$)$_2$—CH=CH— | N | CO |
| H | 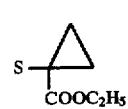 | —(CH$_2$)$_2$—CH=CH— | N | CO |
| H | S—CH$_2$—COOC$_5$H$_{11}$-n | —(CH$_2$)$_2$—CH=CH— | N | CO |

TABLE 1-continued

Examples of the compounds of the formula (I)

| R¹ | R² | A | E | G |
|---|---|---|---|---|
| H | O—CH₂—(phenyl) | —(CH₂)₂—CH=CH— | N | CO |
| H | S—CH₂—(phenyl) | —(CH₂)₂—CH=CH— | N | CO |
| H | O—CH₂CH₂—OCH(CH₂F)₂ | —(CH₂)₂—CH=CH— | N | CO |
| H | S—CH(CH₃)₂ | —(CH₂)₂—CH=CH— | N | CO |
| H | O—CH₂—CCl=CH₂ | —(CH₂)₂—CH=CH— | N | CO |
| H | O—(phenyl) | —(CH₂)₂—CH=CH— | N | CO |
| H | O—CH₂CN | —(CH₂)₂—CH=CH— | N | CO |
| H | O—CH₂COOC₂H₄—OCH₃ | —(CH₂)₂—CH=CH— | N | CO |
| H | O—CH₂—COO—CH(CH₃)COOC₂H₅ | —(CH₂)₂—CH=CH— | N | CO |
| H | OCH₂—COOCH₂—COOC₂H₅ | —(CH₂)₂—CH=CH— | N | CO |
| H | O—CHF₂ | —(CH₂)₂—CH=CH— | N | CO |
| H | O—CH₂CH₂—OCH₂CF₃ | —(CH₂)₂—CH=CH— | N | CO |
| H | NHCH₃ | —(CH₂)₂—CH=CH— | N | CO |
| H | NHC₂H₅ | —(CH₂)₂—CH=CH— | N | CO |
| H | N(CH₃)₂ | —(CH₂)₂—CH=CH— | N | CO |
| H | NH—CH₂—COOC₂H₅ | —(CH₂)₂—CH=CH— | N | CO |
| H | piperidin-1-yl | —(CH₂)₂—CH=CH— | N | CO |
| H | morpholin-4-yl | —(CH₂)₂—CH=CH— | N | CO |
| H | NH—SO₂CH₃ | —(CH₂)₂—CH=CH— | N | CO |
| H | NH—SO₂C₂H₅ | —(CH₂)₂—CH=CH— | N | CO |
| H | NH—SO₂C₃H₇-n | —(CH₂)₂—CH=CH— | N | CO |
| H | NH—SO₂C₃H₇-i | —(CH₂)₂—CH=CH— | N | CO |
| H | NH—SO₂C₄H₉-n | —(CH₂)₂—CH=CH— | N | CO |
| H | NH—SO₂C₈H₁₇-n | —(CH₂)₂—CH=CH— | N | CO |
| H | NH—COOCH₃ | —(CH₂)₂—CH=CH— | N | CO |
| H | NH—COC₂H₅ | —(CH₂)₂—CH=CH— | N | CO |
| H | NH—COCF₃ | —(CH₂)₂—CH=CH— | N | CO |
| H | N(CH₃)—SO₂CH₃ | —(CH₂)₂—CH=CH— | N | CO |
| H | N(CH₃)—SO₂C₂H₅ | —(CH₂)₂—CH=CH— | N | CO |
| H | N(CH₃)—SO₂C₃H₇-n | —(CH₂)₂—CH=CH— | N | CO |
| H | NH—SO₂CF₃ | —(CH₂)₂—CH=CH— | N | CO |
| H | NH—SO₂—(cyclopropyl) | —(CH₂)₂—CH=CH— | N | CO |
| H | NH—SO₂—C₄F₉-n | —(CH₂)₂—CH=CH— | N | CO |
| H | N(CH₃)SO₂CF₃ | —(CH₂)₂—CH=CH— | N | CO |
| H | NH—SO₂—(phenyl) | —(CH₂)₂—CH=CH— | N | CO |
| H | NH—SO₂CH₂—(phenyl) | —(CH₂)₂—CH=CH— | N | CO |

TABLE 1-continued

Examples of the compounds of the formula (I)

| R¹ | R² | A | E | G |
|---|---|---|---|---|
| H | 4-CH₃-C₆H₄-SO₂-N(CH₃)- | -(CH₂)₂-CH=CH- | N | CO |
| Cl | OCH₂CF₃ | -(CH₂)₂-CH=CH- | N | CO |
| Cl | OCF₃ | -(CH₂)₂-CH=CH- | N | CO |
| Cl | OCH₃CH(CH₃)-OC₂H₅ | -(CH₂)₂-CH=CH- | N | CO |
| Cl | tetrahydrofuran-2-yl-CH₂-O- | -(CH₂)₂-CH=CH- | N | CO |
| Cl | OCH₂-CH=CH₂ | -(CH₂)₂-CH=CH- | N | CO |
| Cl | OH | -(CH₂)₂-CH=CH- | N | CO |
| Cl | OCH₂-C≡CH | -(CH₂)₂-CH=CH- | N | CO |
| Cl | SCH₂C≡CH | -(CH₂)₂-CH=CH- | N | CO |
| Cl | OCH₂COOC₂H₅ | -(CH₂)₂-CH=CH- | N | CO |
| Cl | S-C(CH₃)₃ | -(CH₂)₂-CH=CH- | N | CO |
| Cl | OCH₂-COOC₅H₁₁-n | -(CH₂)₂-CH=CH- | N | CO |
| Cl | OCH(CH₃)-COOC₂H₅ | -(CH₂)₂-CH=CH- | N | CO |
| Cl | OCH₂CH₂-OCH₃ | -(CH₂)₂-CH=CH- | N | CO |
| Cl | OCH₂CH₂-OC₂H₅ | -(CH₂)₂-CH=CH- | N | CO |
| Cl | O(CH₂CH₂O)₂-OC₂H₅ | -(CH₂)₂-CH=CH- | N | CO |
| Cl | S-C₃H₇-n | -(CH₂)₂-CH=CH- | N | CO |
| Cl | S-C₂H₅ | -(CH₂)₂-CH=CH- | N | CO |
| Cl | S-CH₃ | -(CH₂)₂-CH=CH- | N | CO |
| Cl | S-CH₂COOC₂H₅ | -(CH₂)₂-CH=CH- | N | CO |
| Cl | SCH₂CH₂-COOC₂H₅ | -(CH₂)₂-CH=CH- | N | CO |
| Cl | O-CH₂-C≡C-CH₃ | -(CH₂)₂-CH=CH- | N | CO |
| Cl | OCH₂-CH=CH-Cl | -(CH₂)₂-CH=CH- | N | CO |
| Cl | O-CH(CH₃)C≡CH | -(CH₂)₂-CH=CH- | N | CO |
| Cl | OCH(CH₃)C≡C-CH₃ | -(CH₂)₂-CH=CH- | N | CO |
| Cl | O-CH(CH₃)CH=CH₂ | -(CH₂)₂-CH=CH- | N | CO |
| Cl | OCH₂CH=CH-CH₃ | -(CH₂)₂-CH=CH- | N | CO |
| Cl | O-CH₃ | -(CH₂)₂-CH=CH- | N | CO |
| Cl | O-C₂H₅ | -(CH₂)₂-CH=CH- | N | CO |
| Cl | O-C₃H₇-n | -(CH₂)₂-CH=CH- | N | CO |
| Cl | O-C₃H₇-iso | -(CH₂)₂-CH=CH- | N | CO |
| Cl | 1-(ethoxycarbonyl)cyclobutyl-1-oxy | -(CH₂)₂-CH=CH- | N | CO |
| Cl | 1,3-dioxolan-2-yl (cyclic O-CH-CH₂-O-) | -(CH₂)₂-CH=CH- | N | CO |
| Cl | O-CH(CH₂F)₂ | -(CH₂)-CH=CH- | N | CO |
| Cl | O-CH₂-C(CH₃)=CH₂ | -(CH₂)-CH=CH- | N | CO |
| Cl | tetrahydrofuran (S-CH₂, O ring) | -(CH₂)-CH=CH- | N | CO |
| Cl | tetrahydropyran-2-yl-CH₂-O- | -(CH₂)-CH=CH- | N | CO |
| Cl | 1-(ethoxycarbonyl)cyclopropyl-1-oxy | -(CH₂)-CH=CH- | N | CO |

TABLE 1-continued

Examples of the compounds of the formula (I)

| R¹ | R² | A | E | G |
|---|---|---|---|---|
| Cl | 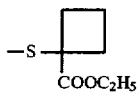 | $-(CH_2)-CH=CH-$ | N | CO |
| Cl | 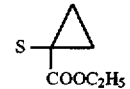 | $-(CH_2)-CH=CH-$ | N | CO |
| Cl | 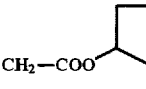 | $-(CH_2)-CH=CH-$ | N | CO |
| Cl | $S-CH_2-COOC_5H_{11}$-n | $-(CH_2)-CH=CH-$ | N | CO |
| Cl | 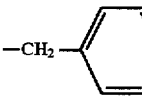 | $-(CH_2)-CH=CH-$ | N | CO |
| Cl | 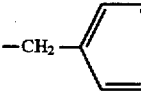 | $-(CH_2)-CH=CH-$ | N | CO |
| Cl | $O-CH_2CH_2-OCH(CH_2F)_2$ | $-(CH_2)-CH=CH-$ | N | CO |
| Cl | $S-CH(CH_3)_2$ | $-(CH_2)-CH=CH-$ | N | CO |
| Cl | $O-CH_2-CCl=CH_2$ | $-(CH_2)-CH=CH-$ | N | CO |
| Cl | 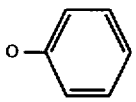 | $-(CH_2)-CH=CH-$ | N | CO |
| Cl | $O-CH_2CN$ | $-(CH_2)-CH=CH-$ | N | CO |
| Cl | $O-CH_2COOC_2H_4-OCH_3$ | $-(CH_2)-CH=CH-$ | N | CO |
| Cl | $O-CH_2-COO-CH(CH_3)COOC_2H_5$ | $-(CH_2)-CH=CH-$ | N | CO |
| Cl | $OCH_2-COOCH_2-COOC_2H_5$ | $-(CH_2)-CH=CH-$ | N | CO |
| Cl | $O-CHF_2$ | $-(CH_2)-CH=CH-$ | N | CO |
| Cl | $O-CH_2CH_2-OCH_2CF_3$ | $-(CH_2)-CH=CH-$ | N | CO |
| Cl | $NHCH_3$ | $-(CH_2)-CH=CH-$ | N | CO |
| Cl | $NHC_2H_5$ | $-(CH_2)-CH=CH-$ | N | CO |
| Cl | $N(CH_3)_2$ | $-(CH_2)-CH=CH-$ | N | CO |
| Cl | $NH-CH_2-COOC_2H_5$ | $-(CH_2)-CH=CH-$ | N | CO |
| Cl | 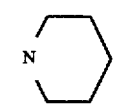 | $-(CH_2)-CH=CH-$ | N | CO |
| Cl | 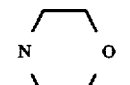 | $-(CH_2)-CH=CH-$ | N | CO |
| Cl | $NH-SO_2CH_3$ | $-(CH_2)-CH=CH-$ | N | CO |
| Cl | $NH-SO_2C_2H_5$ | $-(CH_2)-CH=CH-$ | N | CO |
| Cl | $NH-SO_2C_3H_7$-n | $-(CH_2)-CH=CH-$ | N | CO |
| Cl | $NH-SO_2C_3H_7$-i | $-(CH_2)-CH=CH-$ | N | CO |
| Cl | $NH-SO_2C_4H_9$-n | $-(CH_2)-CH=CH-$ | N | CO |
| Cl | $NH-SO_2C_8H_{17}$-n | $-(CH_2)-CH=CH-$ | N | CO |
| Cl | $NH-COCH_3$ | $-(CH_2)-CH=CH-$ | N | CO |
| Cl | $NH-COC_2H_5$ | $-(CH_2)-CH=CH-$ | N | CO |
| Cl | $NH-COCF_3$ | $-(CH_2)-CH=CH-$ | N | CO |
| Cl | $N(CH_3)-SO_2CH_3$ | $-(CH_2)-CH=CH-$ | N | CO |
| Cl | $N(CH_3)-SO_2C_2H_5$ | $-(CH_2)-CH=CH-$ | N | CO |
| Cl | $N(CH_3)-SO_2C_3H_7$-n | $-(CH_2)-CH=CH-$ | N | CO |
| Cl | $NH-SO_2CF_3$ | $-(CH_2)-CH=CH-$ | N | CO |
| Cl | 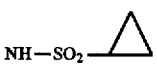 | $-(CH_2)-CH=CH-$ | N | CO |

TABLE 1-continued

Examples of the compounds of the formula (I)

| R¹ | R² | A | E | G |
|---|---|---|---|---|
| Cl | NH—SO₂—C₄F₉-n | —(CH₂)—CH=CH— | N | CO |
| Cl | N(CH₃)SO₂CF₃ | —(CH₂)—CH=CH— | N | CO |
| Cl | NH—SO₂—C₆H₅ | —(CH₂)—CH=CH— | N | CO |
| Cl | NH—SO₂CH₂—C₆H₅ | —(CH₂)—CH=CH— | N | CO |
| Cl | N(CH₃)—SO₂—C₆H₄—CH₃ | —(CH₂)—CH=CH— | N | CO |
| F | O—(CH₂F)₂ | —(CH₂)₄— | \C=/ | =N— |
| F | O—CH₂—C(CH₃)=CH₂ | —(CH₂)₄— | \C=/ | =N— |
| F | S—CH₂-(tetrahydrofuran-2-yl) | —(CH₂)₄— | \C=/ | =N— |
| F | O—CH₂-(tetrahydropyran-2-yl) | —(CH₂)₄— | \C=/ | =N— |
| F | O-(1-COOC₂H₅-cyclopropyl) | —(CH₂)₄— | \C=/ | =N— |
| F | —S-(1-COOC₂H₅-cyclobutyl) | —(CH₂)₄— | \C=/ | =N— |
| F | S-(1-COOC₂H₅-cyclopropyl) | —(CH₂)₄— | \C=/ | =N— |
| F | S—CH₂—COO-cyclopentyl | —(CH₂)₄— | \C=/ | =N— |
| F | S—CH₂—COOC₅H₁₁-n | —(CH₂)₄— | \C=/ | =N— |
| F | O—CH₂—C₆H₅ | —(CH₂)₄— | \C=/ | =N— |
| F | S—CH₂—C₆H₅ | —(CH₂)₄— | \C=/ | =N— |

TABLE 1-continued

Examples of the compounds of the formula (I)

| R$^1$ | R$^2$ | A | E | G |
|---|---|---|---|---|
| F | O—CH$_2$CH$_2$—OCH(CH$_2$F)$_2$ | —(CH$_2$)$_4$— | \C= / | =N— |
| F | S—CH(CH$_3$)$_2$ | —(CH$_2$)$_4$— | \C= / | =N— |
| F | O—CH$_2$—CCl=CH$_2$ | —(CH$_2$)$_4$— | \C= / | =N— |
| F | O—C$_6$H$_5$ | —(CH$_2$)$_4$— | \C= / | =N— |
| F | O—CH$_2$CN | —(CH$_2$)$_4$— | \C= / | =N— |
| F | O—CH$_2$COOC$_2$H$_4$—OCH$_3$ | —(CH$_2$)$_4$— | \C= / | =N— |
| F | O—CH$_2$—COO—CH(CH$_3$)COOC$_2$H$_5$ | —(CH$_2$)$_4$— | \C= / | =N— |
| F | OCH$_2$—COOCH$_2$—COOC$_2$H$_5$ | —(CH$_2$)$_4$— | \C= / | =N— |
| F | O—CHF$_2$ | —(CH$_2$)$_4$— | \C= / | =N— |
| F | O—CH$_2$CH$_2$—OCH$_2$CF$_3$ | —(CH$_2$)$_4$— | \C= / | =N— |
| F | OCH$_2$CF$_3$ | —(CH$_2$)$_4$— | \C= / | =N— |
| F | OCF$_3$ | —(CH$_2$)$_4$— | \C= / | =N— |
| F | OCH$_2$CH(CH$_3$)—OC$_2$H$_5$ | —(CH$_2$)$_4$— | \C= / | =N— |
| F | O—CH$_2$—(tetrahydrofuran-2-yl) | —(CH$_2$)$_4$— | \C= / | =N— |

TABLE 1-continued

Examples of the compounds of the formula (I)

| R¹ | R² | A | E | G |
|---|---|---|---|---|
| F | OCH₂—CH=CH₂ | —(CH₂)₄— | \C=/ | =N— |
| F | OH | —(CH₂)₄— | \C=/ | =N— |
| F | OCH₂—C≡CH | —(CH₂)₄— | \C=/ | =N— |
| F | SCH₂C≡CH | —(CH₂)₄— | \C=/ | =N— |
| F | OCH₂COOC₂H₅ | —(CH₂)₄— | \C=/ | =N— |
| F | S—C(CH₃)₃ | —(CH₂)₄— | \C=/ | =N— |
| F | OCH₂—COOC₅H₁₁-n | —(CH₂)₄— | \C=/ | =N— |
| F | OCH(CH₃)—COOC₂H₅ | —(CH₂)₄— | \C=/ | =N— |
| F | OCH₂CH₂—OCH₃ | —(CH₂)₄— | \C=/ | =N— |
| F | OCH₂CH₂—OC₂H₅ | —(CH₂)₄— | \C=/ | =N— |
| F | O(CH₂CH₂O)₂—OC₂H₅ | —(CH₂)₄— | \C=/ | =N— |
| F | S—C₃H₇-n | —(CH₂)₄— | \C=/ | =N— |
| F | S—C₂H₅ | —(CH₂)₄— | \C=/ | =N— |
| F | S—CH₃ | —(CH₂)₄— | \C=/ | =N— |
| F | S—CH₂COOC₂H₅ | —(CH₂)₄— | \C=/ | =N— |

TABLE 1-continued

Examples of the compounds of the formula (I)

| R¹ | R² | A | E | G |
|---|---|---|---|---|
| F | SCH₂CH₂—COOC₂H₅ | —(CH₂)₄— | \C=/ | =N— |
| F | O—CH₂—C≡C—CH₃ | —(CH₂)₄— | \C=/ | =N— |
| F | OCH₂—CH=CH—Cl | —(CH₂)₄— | \C=/ | =N— |
| F | O—CH(CH₃)C≡CH | —(CH₂)₄— | \C=/ | =N— |
| F | OCH(CH₃)C≡C—CH₃ | —(CH₂)₄— | \C=/ | =N— |
| F | O—CH(CH₃)CH=CH₂ | —(CH₂)₄— | \C=/ | =N— |
| F | OCH₂CH=CH—CH₃ | —(CH₂)₄— | \C=/ | =N— |
| F | O—CH₃ | —(CH₂)₄— | \C=/ | =N— |
| F | O—C₂H₅ | —(CH₂)₄— | \C=/ | =N— |
| F | O—C₃H₇-n | —(CH₂)₄— | \C=/ | =N— |
| F | O—C₃H₇-iso | —(CH₂)₄— | \C=/ | =N— |
| F | O—[cyclobutyl]—COOC₂H₅ | —(CH₂)₄— | \C=/ | =N— |
| F | [tetrahydrofuran-2-yl-O—] | —(CH₂)₄— | \C=/ | =N— |
| F | NHCH₃ | —(CH₂)₄— | \C=/ | =N— |

TABLE 1-continued

Examples of the compounds of the formula (I)

| R¹ | R² | A | E | G |
|---|---|---|---|---|
| F | NHC₂H₅ | —(CH₂)₄— | \C=/ | =N— |
| F | N(CH₃)₂ | —(CH₂)₄— | \C=/ | =N— |
| F | NH—CH₂—COOC₂H₅ | —(CH₂)₄— | \C=/ | =N— |
| F | piperidinyl (N) | —(CH₂)₄— | \C=/ | =N— |
| F | morpholinyl (N, O) | —(CH₂)₄— | \C=/ | =N— |
| F | NH—SO₂CH₃ | —(CH₂)₄— | \C=/ | =N— |
| F | NH—SO₂C₂H₅ | —(CH₂)₄— | \C=/ | =N— |
| F | NH—SO₂C₃H₇-n | —(CH₂)₄— | \C=/ | =N— |
| F | NH—SO₂C₃H₇-i | —(CH₂)₄— | \C=/ | =N— |
| F | NH—SO₂C₄H₉-n | —(CH₂)₄— | \C=/ | =N— |
| F | NH—SO₂C₈H₁₇-n | —(CH₂)₄— | \C=/ | =N— |
| F | NH—COCH₃ | —(CH₂)₄— | \C=/ | =N— |
| F | NH—COC₂H₅ | —(CH₂)₄— | \C=/ | =N— |
| F | NH—COCF₃ | —(CH₂)₄— | \C=/ | =N— |
| F | N(CH₃)—SO₂CH₃ | —(CH₂)₄— | \C=/ | =N— |

TABLE 1-continued

Examples of the compounds of the formula (I)

| R¹ | R² | A | E | G |
|---|---|---|---|---|
| F | N(CH₃)—SO₂C₂H₅ | —(CH₂)₄— | >C= | =N— |
| F | N(CH₃)—SO₂C₃H₇-n | —(CH₂)₄— | >C= | =N— |
| F | NH—SO₂CF₃ | —(CH₂)₄— | >C= | =N— |
| F | NH—SO₂—△ | —(CH₂)₄— | >C= | =N— |
| F | NH—SO₂—C₄F₉-n | —(CH₂)₄— | >C= | =N— |
| F | N(CH₃)SO₂CF₃ | —(CH₂)₄— | >C= | =N— |
| F | NH—SO₂—C₆H₅ | —(CH₂)₄— | >C= | =N— |
| F | NH—SO₂CH₂—C₆H₅ | —(CH₂)₄— | >C= | =N— |
| F | N(CH₃)—SO₂—C₆H₄—CH₃ | —(CH₂)₄— | >C= | =N— |
| H | OCH₂CF₃ | —(CH₂)₄— | >C= | =N— |
| H | OCF₃ | —(CH₂)₄— | >C= | =N— |
| H | OCH₂CH(CH₃)—OC₂H₅ | —(CH₂)₄— | >C= | =N— |
| H | (tetrahydrofuran-2-yl)OCH₂— | —(CH₂)₄— | >C= | =N— |
| H | OCH₂—CH=CH₂ | —(CH₂)₄— | >C= | =N— |

TABLE 1-continued

Examples of the compounds of the formula (I)

| R¹ | R² | A | E | G |
|---|---|---|---|---|
| H | OH | $-(CH_2)_4-$ | $\diagdown C= \diagup$ | $=N-$ |
| H | $OCH_2-C\equiv CH$ | $-(CH_2)_4-$ | $\diagdown C= \diagup$ | $=N-$ |
| H | $SCH_2C\equiv CH$ | $-(CH_2)_4-$ | $\diagdown C= \diagup$ | $=N-$ |
| H | $OCH_2COOC_2H_5$ | $-(CH_2)_4-$ | $\diagdown C= \diagup$ | $=N-$ |
| H | $S-C(CH_3)_3$ | $-(CH_2)_4-$ | $\diagdown C= \diagup$ | $=N-$ |
| H | $OCH_2-COOC_5H_{11}\text{-}n$ | $-(CH_2)_4-$ | $\diagdown C= \diagup$ | $=N-$ |
| H | $OCH(CH_3)-COOC_2H_5$ | $-(CH_2)_4-$ | $\diagdown C= \diagup$ | $=N-$ |
| H | $OCH_2CH_2-OCH_3$ | $-(CH_2)_4-$ | $\diagdown C= \diagup$ | $=N-$ |
| H | $OCH_2CH_2-OC_2H_5$ | $-(CH_2)_4-$ | $\diagdown C= \diagup$ | $=N-$ |
| H | $O(CH_2CH_2O)_2-OC_2H_5$ | $-(CH_2)_4-$ | $\diagdown C= \diagup$ | $=N-$ |
| H | $S-C_3H_7\text{-}n$ | $-(CH_2)_4-$ | $\diagdown C= \diagup$ | $=N-$ |
| H | $S-C_2H_5$ | $-(CH_2)_4-$ | $\diagdown C= \diagup$ | $=N-$ |
| H | $S-CH_3$ | $-(CH_2)_4-$ | $\diagdown C= \diagup$ | $=N-$ |
| H | $S-CH_2COOC_2H_5$ | $-(CH_2)_4-$ | $\diagdown C= \diagup$ | $=N-$ |
| H | $SCH_2CH_2-COOC_2H_5$ | $-(CH_2)_4-$ | $\diagdown C= \diagup$ | $=N-$ |

TABLE 1-continued

Examples of the compounds of the formula (I)

| R¹ | R² | A | E | G |
|---|---|---|---|---|
| H | O—CH₂—C≡C—CH₃ | —(CH₂)₄— | \C=/ | =N— |
| H | OCH₂—CH=CH—Cl | —(CH₂)₄— | \C=/ | =N— |
| H | O—CH(CH₃)C≡CH | —(CH₂)₄— | \C=/ | =N— |
| H | OCH(CH₃)C≡C—CH₃ | —(CH₂)₄— | \C=/ | =N— |
| H | O—CH(CH₃)CH=CH₂ | —(CH₂)₄— | \C=/ | =N— |
| H | OCH₂CH=CH—CH₃ | —(CH₂)₄— | \C=/ | =N— |
| H | O—CH₃ | —(CH₂)₄— | \C=/ | =N— |
| H | O—C₂H₅ | —(CH₂)₄— | \C=/ | =N— |
| H | O—C₃H₇-n | —(CH₂)₄— | \C=/ | =N— |
| H | O—C₃H₇-iso | —(CH₂)₄— | \C=/ | =N— |
| H | O—[cyclobutyl with COOC₂H₅] | —(CH₂)₄— | \C=/ | =N— |
| H | —O—[tetrahydrofuran-2-yl] | —(CH₂)₄— | \C=/ | =N— |
| H | O—CH(CH₂F)₂ | —(CH₂)₄— | \C=/ | =N— |
| H | O—CH₂—C(CH₃)=CH₂ | —(CH₂)₄— | \C=/ | =N— |

5,756,805

TABLE 1-continued

Examples of the compounds of the formula (I)

| R¹ | R² | A | E | G |
|---|---|---|---|---|
| H |  | —(CH$_2$)$_4$— | \C=/ | =N— |
| H |  | —(CH$_2$)$_4$— | \C=/ | =N— |
| H |  | —(CH$_2$)$_4$— | \C=/ | =N— |
| H |  | —(CH$_2$)$_4$— | \C=/ | =N— |
| H |  | —(CH$_2$)$_4$— | \C=/ | =N— |
| H |  | —(CH$_2$)$_4$— | \C=/ | =N— |
| H | S—CH$_2$—COOC$_5$H$_{11}$-n | —(CH$_2$)$_4$— | \C=/ | =N— |
| H |  | —(CH$_2$)$_4$— | \C=/ | =N— |
| H |  | —(CH$_2$)$_4$— | \C=/ | =N— |
| H | O—CH$_2$CH$_2$—OCH(CH$_2$F)$_2$ | —(CH$_2$)$_4$— | \C=/ | =N— |
| H | S—CH(CH$_3$)$_2$ | —(CH$_2$)$_4$— | \C=/ | =N— |
| H | O—CH$_2$—CCl=CH$_2$ | —(CH$_2$)$_4$— | \C=/ | =N— |
| H |  | —(CH$_2$)$_4$— | \C=/ | =N— |
| H | O—CH$_2$CN | —(CH$_2$)$_4$— | \C=/ | =N— |

TABLE 1-continued

Examples of the compounds of the formula (I)

| R¹ | R² | A | E | G |
|---|---|---|---|---|
| H | O—CH₂COOC₂H₄—OCH₃ | —(CH₂)₄— | \C=/ | =N— |
| H | O—CH₂—COO—CH(CH₃)COOC₂H₅ | —(CH₂)₄— | \C=/ | =N— |
| H | OCH₂—COOCH₂—COOC₂H₅ | —(CH₂)₄— | \C=/ | =N— |
| H | O—CHF₂ | —(CH₂)₄— | \C=/ | =N— |
| H | O—CH₂CH₂—OCH₂CF₃ | —(CH₂)₄— | \C=/ | =N— |
| H | NHCH₃ | —(CH₂)₄— | \C=/ | =N— |
| H | NHC₂H₅ | —(CH₂)₄— | \C=/ | =N— |
| H | N(CH₃)₂ | —(CH₂)₄— | \C=/ | =N— |
| H | NH—CH₂—COOC₂H₅ | —(CH₂)₄— | \C=/ | =N— |
| H | piperidin-1-yl | —(CH₂)₄— | \C=/ | =N— |
| H | morpholin-4-yl | —(CH₂)₄— | \C=/ | =N— |
| H | NH—SO₂CH₃ | —(CH₂)₄— | \C=/ | =N— |
| H | NH—SO₂C₂H₅ | —(CH₂)₄— | \C=/ | =N— |
| H | NH—SO₂C₃H₇-n | —(CH₂)₄— | \C=/ | =N— |
| H | NH—SO₂—C₃H₇-i | —(CH₂)₄— | \C=/ | =N— |

TABLE 1-continued

Examples of the compounds of the formula (I)

| R¹ | R² | A | E | G |
|---|---|---|---|---|
| H | NH—SO$_2$C$_4$H$_9$-n | —(CH$_2$)$_4$— | \C=/ | =N— |
| H | NH—SO$_2$C$_8$H$_{17}$-n | —(CH$_2$)$_4$— | \C=/ | =N— |
| H | NH—COCH$_3$ | —(CH$_2$)$_4$— | \C=/ | =N— |
| H | NH—COC$_2$H$_5$ | —(CH$_2$)$_4$— | \C=/ | =N— |
| H | NH—COCF$_3$ | —(CH$_2$)$_4$— | \C=/ | =N— |
| H | N(CH$_3$)—SO$_2$CH$_3$ | —(CH$_2$)$_4$— | \C=/ | =N— |
| H | N(CH$_3$)—SO$_2$C$_2$H$_5$ | —(CH$_2$)$_4$— | \C=/ | =N— |
| H | N(CH$_3$)—SO$_2$C$_3$H$_7$-n | —(CH$_2$)$_4$— | \C=/ | =N— |
| H | NH—SO$_2$CF$_3$ | —(CH$_2$)$_4$— | \C=/ | =N— |
| H | NH—SO$_2$—△ | —(CH$_2$)$_4$— | \C=/ | =N— |
| H | NH—SO$_2$—C$_4$F$_9$-n | —(CH$_2$)$_4$— | \C=/ | =N— |
| H | N(CH$_3$)SO$_2$CF$_3$ | —(CH$_2$)$_4$— | \C=/ | =N— |
| H | NH—SO$_2$—C$_6$H$_5$ | —(CH$_2$)$_4$— | \C=/ | =N— |
| H | NH—SO$_2$CH$_2$—C$_6$H$_5$ | —(CH$_2$)$_4$— | \C=/ | =N— |

TABLE 1-continued

Examples of the compounds of the formula (I)

| R¹ | R² | A | E | G |
|---|---|---|---|---|
| H | 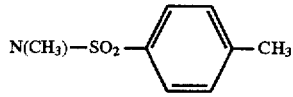 N(CH₃)—SO₂—⟨C₆H₄⟩—CH₃ | —(CH₂)₄— |  \C=/ | =N— |
| Cl | OCH₂CF₃ | —(CH₂)₄— | \C=/ | =N— |
| Cl | OCF₃ | —(CH₂)₄— | \C=/ | =N— |
| Cl | OCH₂CH(CH₃)—OC₂H₅ | —(CH₂)₄— | \C=/ | =N— |
| Cl |  tetrahydrofuranyl-O—CH₂ | —(CH₂)₄— | \C=/ | =N— |
| Cl | OCH₂—CH=CH₂ | —(CH₂)₄— | \C=/ | =N— |
| Cl | OH | —(CH₂)₄— | \C=/ | =N— |
| Cl | OCH₂—C≡CH | —(CH₂)₄— | \C=/ | =N— |
| Cl | SCH₂C≡CH | —(CH₂)₄— | \C=/ | =N— |
| Cl | OCH₂COOC₂H₅ | —(CH₂)₄— | \C=/ | =N— |
| Cl | S—C(CH₃)₃ | —(CH₂)₄— | \C=/ | =N— |
| Cl | OCH₂—COOC₅H₁₁-n | —(CH₂)₄— | \C=/ | =N— |
| Cl | OCH(CH₃)—COOC₂H₅ | —(CH₂)₄— | \C=/ | =N— |
| Cl | OCH₂CH₂—OCH₃ | —(CH₂)₄— | \C=/ | =N— |
| Cl | OCH₂CH₂—OC₂H₅ | —(CH₂)₄— | \C=/ | =N— |

TABLE 1-continued

Examples of the compounds of the formula (I)

| R¹ | R² | A | E | G |
|---|---|---|---|---|
| Cl | O(CH₂CH₂O)₂—OC₂H₅ | —(CH₂)₄— | \C=/ | =N— |
| Cl | S—C₃H₇-n | —(CH₂)₄— | \C=/ | =N— |
| Cl | S—C₂H₅ | —(CH₂)₄— | \C=/ | =N— |
| Cl | S—CH₃ | —(CH₂)₄— | \C=/ | =N— |
| Cl | S—CH₂COOC₂H₅ | —(CH₂)₄— | \C=/ | =N— |
| Cl | SCH₂CH₂—COOC₂H₅ | —(CH₂)₄— | \C=/ | =N— |
| Cl | O—CH₂—C≡C—CH₃ | —(CH₂)₄— | \C=/ | =N— |
| Cl | OCH₂—CH=CH—Cl | —(CH₂)₄— | \C=/ | =N— |
| Cl | O—CH(CH₃)C≡CH | —(CH₂)₄— | \C=/ | =N— |
| Cl | OCH(CH₃)C≡C—CH₃ | —(CH₂)₄— | \C=/ | =N— |
| Cl | O—CH(CH₃)CH=CH₂ | —(CH₂)₄— | \C=/ | =N— |
| Cl | OCH₂CH=CH—CH₃ | —(CH₂)₄— | \C=/ | =N— |
| Cl | O—CH₃ | —(CH₂)₄— | \C=/ | =N— |
| Cl | O—C₂H₅ | —(CH₂)₄— | \C=/ | =N— |

TABLE 1-continued
Examples of the compounds of the formula (I)
| R¹ | R² | A | E | G |
|---|---|---|---|---|
| Cl | O—C₃H₇-n | —(CH₂)₄— | \C=/ | =N— |
| Cl | O—C₃H₇-iso | —(CH₂)₄— | \C=/ | =N— |
| Cl |  | —(CH₂)₄— | \C=/ | =N— |
| Cl |  | —(CH₂)₄— | \C=/ | =N— |
| Cl | O—CH(CH₂F)₂ | —(CH₂)₄— | \C=/ | =N— |
| Cl | O—CH₂—C(CH₃)=CH₂ | —(CH₂)₄— | \C=/ | =N— |
| Cl | 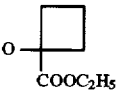 | —(CH₂)₄— | \C=/ | =N— |
| Cl |  | —(CH₂)₄— | \C=/ | =N— |
| Cl | 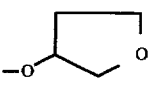 | —(CH₂)₄— | \C=/ | =N— |
| Cl |  | —(CH₂)₄— | \C=/ | =N— |
| Cl |  | —(CH₂)₄— | \C=/ | =N— |
| Cl |  | —(CH₂)₄— | \C=/ | =N— |
| Cl | S—CH₂—COOC₅H₁₁-n | —(CH₂)₄— | \C=/ | =N— |
| Cl | 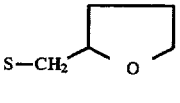 | —(CH₂)₄— | \C=/ | =N— |

TABLE 1-continued

Examples of the compounds of the formula (I)

| R¹ | R² | A | E | G |
|---|---|---|---|---|
| Cl | S—CH₂—C₆H₅ | —(CH₂)₄— | \C=/ | =N— |
| Cl | O—CH₂CH₂—OCH(CH₂F)₂ | —(CH₂)₄— | \C=/ | =N— |
| Cl | S—CH(CH₃)₂ | —(CH₂)₄— | \C=/ | =N— |
| Cl | O—CH₂—CCl=CH₂ | —(CH₂)₄— | \C=/ | =N— |
| Cl | O—C₆H₅ | —(CH₂)₄— | \C=/ | =N— |
| Cl | O—CH₂CN | —(CH₂)₄— | \C=/ | =N— |
| Cl | O—CH₂COOC₂H₄—OCH₃ | —(CH₂)₄— | \C=/ | =N— |
| Cl | O—CH₂—COO—CH(CH₃)COOC₂H₅ | —(CH₂)₄— | \C=/ | =N— |
| Cl | OCH₂—COOCH₂—COOC₂H₅ | —(CH₂)₄— | \C=/ | =N— |
| Cl | O—CHF₂ | —(CH₂)₄— | \C=/ | =N— |
| Cl | O—CH₂CH₂—OCH₂CF₃ | —(CH₂)₄— | \C=/ | =N— |
| Cl | NHCH₃ | —(CH₂)₄— | \C=/ | =N— |
| Cl | NHC₂H₅ | —(CH₂)₄— | \C=/ | =N— |
| Cl | N(CH₃)₂ | —(CH₂)₄— | \C=/ | =N— |
| Cl | NH—CH₂—COOC₂H₅ | —(CH₂)₄— | \C=/ | =N— |

TABLE 1-continued

Examples of the compounds of the formula (I)

| R¹ | R² | A | E | G |
|----|----|---|---|---|
| Cl | NH—COCH₃ | —(CH₂)₄— | \C=/ | =N— |
| Cl | NH—COC₂H₅ | —(CH₂)₄— | \C=/ | =N— |
| Cl | NH—COCF₃ | —(CH₂)₄— | \C=/ | =N— |
| Cl | N(CH₃)—SO₂CH₃ | —(CH₂)₄— | \C=/ | =N— |
| Cl | N(CH₃)—SO₂C₂H₅ | —(CH₂)₄— | \C=/ | =N— |
| Cl | N(CH₃)—SO₂C₃H₇-n | —(CH₂)₄— | \C=/ | =N— |
| Cl | NH—SO₂CF₃ | —(CH₂)₄— | \C=/ | =N— |
| Cl | NH—SO₂—△ | —(CH₂)₄— | \C=/ | =N— |
| Cl | (piperidinyl) | —(CH₂)₄— | \C=/ | =N— |
| Cl | (morpholinyl) | —(CH₂)₄— | \C=/ | =N— |
| Cl | NH—SO₂CH₃ | —(CH₂)₄— | \C=/ | =N— |
| Cl | NH—SO₂C₂H₅ | —(CH₂)₄— | \C=/ | =N— |
| Cl | NH—SO₂C₃H₇-n | —(CH₂)₄— | \C=/ | =N— |
| Cl | NH—SO₂C₃H₇-i | —(CH₂)₄— | \C=/ | =N— |

TABLE 1-continued

Examples of the compounds of the formula (I)

| R¹ | R² | A | E | G |
|---|---|---|---|---|
| Cl | NH—SO$_2$C$_4$H$_9$-n | —(CH$_2$)$_4$— | \C=/ | =N— |
| Cl | NH—SO$_2$C$_8$H$_{17}$-n | —(CH$_2$)$_4$— | \C=/ | =N— |
| Cl | NH—SO$_2$—C$_4$F$_9$-n | —(CH$_2$)$_4$— | \C=/ | =N— |
| Cl | N(CH$_3$)SO$_2$CF$_3$ | —(CH$_2$)$_4$— | \C=/ | =N— |
| Cl | NH—SO$_2$—C$_6$H$_5$ | —(CH$_2$)$_4$— | \C=/ | =N— |
| Cl | NH—SO$_2$CH$_2$—C$_6$H$_5$ | —(CH$_2$)$_4$— | \C=/ | =N— |
| Cl | N(CH$_3$)—SO$_2$—C$_6$H$_4$—CH$_3$ | —(CH$_2$)$_4$— | \C=/ | =N— |
| F | O—CH(CH$_2$F)$_2$ | —(CH$_2$)$_3$— | \C=/ | =N— |
| F | O—CH$_2$—C(CH$_3$)=CH$_2$ | —(CH$_2$)$_3$— | \C=/ | =N— |
| F | S—CH$_2$-(tetrahydrofuran-2-yl) | —(CH$_2$)$_3$— | \C=/ | =N— |
| F | O—CH$_2$-(tetrahydropyran-2-yl) | —(CH$_2$)$_3$— | \C=/ | =N— |
| F | O-(1-COOC$_2$H$_5$-cyclopropyl) | —(CH$_2$)$_3$— | \C=/ | =N— |
| F | S-(1-COOC$_2$H$_5$-cyclobutyl) | —(CH$_2$)$_3$— | \C=/ | =N— |
| F | S-(1-COOC$_2$H$_5$-cyclopropyl) | —(CH$_2$)$_3$— | \C=/ | =N— |

TABLE 1-continued

Examples of the compounds of the formula (I)

| R¹ | R² | A | E | G |
|---|---|---|---|---|
| F | S—CH₂—COO—(cyclopentyl) | —(CH₂)₃— | \C=/ | =N— |
| F | S—CH₂—COOC₅H₁₁-n | —(CH₂)₃— | \C=/ | =N— |
| F | O—CH₂—(phenyl) | —(CH₂)₃— | \C=/ | =N— |
| F | S—CH₂—(phenyl) | —(CH₂)₃— | \C=/ | =N— |
| F | O—CH₂CH₂—OCH(CH₂F)₂ | —(CH₂)₃— | \C=/ | =N— |
| F | S—CH(CH₃)₂ | —(CH₂)₃— | \C=/ | =N— |
| F | O—CH₂—CCl=CH₂ | —(CH₂)₃— | \C=/ | =N— |
| F | O—(phenyl) | —(CH₂)₃— | \C=/ | =N— |
| F | O—CH₂CN | —(CH₂)₃— | \C=/ | =N— |
| F | O—CH₂COOC₂H₄—OCH₃ | —(CH₂)₃— | \C=/ | =N— |
| F | O—CH₂—COO—CH(CH₃)COOC₂H₅ | —(CH₂)₃— | \C=/ | =N— |
| F | OCH₂—COOCH₂—COOC₂H₅ | —(CH₂)₃— | \C=/ | =N— |
| F | O—CHF₂ | —(CH₂)₃— | \C=/ | =N— |
| F | O—CH₂CH₂—OCH₂CF₃ | —(CH₂)₃— | \C=/ | =N— |
| F | OCH₂CF₃ | —(CH₂)₃— | \C=/ | =N— |

TABLE 1-continued

Examples of the compounds of the formula (I)

| R¹ | R² | A | E | G |
|---|---|---|---|---|
| F | OCF₃ | —(CH₂)₃— | \C= | =N— |
| F | OCH₂CH(CH₃)—OC₂H₅ | —(CH₂)₃— | \C= | =N— |
| F | (tetrahydrofuran-2-yl-methoxy: O—CH₂—[tetrahydrofuran ring]) | —(CH₂)₃— | \C= | =N— |
| F | OCH₂—CH=CH₂ | —(CH₂)₃— | \C= | =N— |
| F | OH | —(CH₂)₃— | \C= | =N— |
| F | OCH₂—C≡CH | —(CH₂)₃— | \C= | =N— |
| F | SCH₂C≡CH | —(CH₂)₃— | \C= | =N— |
| F | OCH₂COOC₂H₅ | —(CH₂)₃— | \C= | =N— |
| F | S—C(CH₃)₃ | —(CH₂)₃— | \C= | =N— |
| F | OCH₂—COOC₅H₁₁-n | —(CH₂)₃— | \C= | =N— |
| F | OCH(CH₃)—COOC₂H₅ | —(CH₂)₃— | \C= | =N— |
| F | OCH₂CH₂—OCH₃ | —(CH₂)₃— | \C= | =N— |
| F | OCH₂CH₂—OC₂H₅ | —(CH₂)₃— | \C= | =N— |
| F | O(CH₂CH₂O)₂—OC₂H₅ | —(CH₂)₃— | \C= | =N— |

TABLE 1-continued

Examples of the compounds of the formula (I)

| R¹ | R² | A | E | G |
|---|---|---|---|---|
| F | S—C₃H₇-n | —(CH₂)₃— | \C=/ | =N— |
| F | S—C₂H₅ | —(CH₂)₃— | \C=/ | =N— |
| F | S—CH₃ | —(CH₂)₃— | \C=/ | =N— |
| F | S—CH₂COOC₂H₅ | —(CH₂)₃— | \C=/ | =N— |
| F | SCH₂CH₂—COOC₂H₅ | —(CH₂)₃— | \C=/ | =N— |
| F | O—CH₂—C≡C—CH₃ | —(CH₂)₃— | \C=/ | =N— |
| F | OCH₂—CH=CH—Cl | —(CH₂)₃— | \C=/ | =N— |
| F | O—CH(CH₃)C≡CH | —(CH₂)₃— | \C=/ | =N— |
| F | OCH(CH₃)C≡C—CH₃ | —(CH₂)₃— | \C=/ | =N— |
| F | O—CH(CH₃)CH=CH₂ | —(CH₂)₃— | \C=/ | =N— |
| F | OCH₂CH=CH—CH₃ | —(CH₂)₃— | \C=/ | =N— |
| F | O—CH₃ | —(CH₂)₃— | \C=/ | =N— |
| F | O—C₂H₅ | —(CH₂)₃— | \C=/ | =N— |
| F | O—C₃H₇-n | —(CH₂)₃— | \C=/ | =N— |
| F | O—C₃H₇-iso | —(CH₂)₃— | \C=/ | =N— |

TABLE 1-continued

Examples of the compounds of the formula (I)

| R¹ | R² | A | E | G |
|---|---|---|---|---|
| F | (oxetane-C-COOC₂H₅) | $-(CH_2)_3-$ | $\backslash C= /$ | $=N-$ |
| F | (tetrahydrofuran-3-yloxy) | $-(CH_2)_3-$ | $\backslash C= /$ | $=N-$ |
| F | NHCH₃ | $-(CH_2)_3-$ | $\backslash C= /$ | $=N-$ |
| F | NHC₂H₅ | $-(CH_2)_3-$ | $\backslash C= /$ | $=N-$ |
| F | N(CH₃)₂ | $-(CH_2)_3-$ | $\backslash C= /$ | $=N-$ |
| F | NH—CH₂—COOC₂H₅ | $-(CH_2)_3-$ | $\backslash C= /$ | $=N-$ |
| F | (piperidin-1-yl) | $-(CH_2)_3-$ | $\backslash C= /$ | $=N-$ |
| F | (morpholin-4-yl) | $-(CH_2)_3-$ | $\backslash C= /$ | $=N-$ |
| F | NH—SO₂CH₃ | $-(CH_2)_3-$ | $\backslash C= /$ | $=N-$ |
| F | NH—SO₂C₂H₅ | $-(CH_2)_3-$ | $\backslash C= /$ | $=N-$ |
| F | NH—SO₂C₃H₇-n | $-(CH_2)_3-$ | $\backslash C= /$ | $=N-$ |
| F | NH—SO₂C₃H₇-i | $-(CH_2)_3-$ | $\backslash C= /$ | $=N-$ |
| F | NH—SO₂C₄H₉-n | $-(CH_2)_3-$ | $\backslash C= /$ | $=N-$ |
| F | NH—SO₂C₈H₁₇-n | $-(CH_2)_3-$ | $\backslash C= /$ | $=N-$ |

TABLE 1-continued

Examples of the compounds of the formula (I)

| R¹ | R² | A | E | G |
|---|---|---|---|---|
| F | NH—COCH₃ | —(CH₂)₃— | \C=/ | =N— |
| F | NH—COC₂H₅ | —(CH₂)₃— | \C=/ | =N— |
| F | NH—COCF₃ | —(CH₂)₃— | \C=/ | =N— |
| F | N(CH₃)—SO₂CH₃ | —(CH₂)₃— | \C=/ | =N— |
| F | N(CH₃)—SO₂C₂H₅ | —(CH₂)₃— | \C=/ | =N— |
| F | N(CH₃)—SO₂C₃H₇-n | —(CH₂)₃— | \C=/ | =N— |
| F | NH—SO₂CF₃ | —(CH₂)₃— | \C=/ | =N— |
| F | NH—SO₂—△ | —(CH₂)₃— | \C=/ | =N— |
| F | NH—SO₂—C₄F₉-n | —(CH₂)₃— | \C=/ | =N— |
| F | N(CH₃)SO₂CF₃ | —(CH₂)₃— | \C=/ | =N— |
| F | NH—SO₂—C₆H₅ | —(CH₂)₃— | \C=/ | =N— |
| F | NH—SO₂CH₂—C₆H₅ | —(CH₂)₃— | \C=/ | =N— |
| F | N(CH₃)—SO₂—C₆H₄—CH₃ | —(CH₂)₃— | \C=/ | =N— |
| H | OCH₂CF₃ | —(CH₂)₃— | \C=/ | =N— |
| H | OCF₃ | —(CH₂)₃— | \C=/ | =N— |

TABLE 1-continued

Examples of the compounds of the formula (I)

| R¹ | R² | A | E | G |
|---|---|---|---|---|
| H | OCH₂CH(CH₃)—OC₂H₅ | —(CH₂)₃— | \C=/ | =N— |
| H | 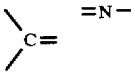 | —(CH₂)₃— | \C=/ | =N— |
| H | OCH₂—CH=CH₂ | —(CH₂)₃— | \C=/ | =N— |
| H | OH | —(CH₂)₃— | \C=/ | =N— |
| H | OCH₂—C≡CH | —(CH₂)₃— | \C=/ | =N— |
| H | SCH₂C≡CH | —(CH₂)₃— | \C=/ | =N— |
| H | OCH₂COOC₂H₅ | —(CH₂)₃— | \C=/ | =N— |
| H | S—C(CH₃)₃ | —(CH₂)₃— | \C=/ | =N— |
| H | OCH₂—COOC₅H₁₁-n | —(CH₂)₃— | \C=/ | =N— |
| H | OCH(CH₃)—COOC₂H₅ | —(CH₂)₃— | \C=/ | =N— |
| H | OCH₂CH₂—OCH₃ | —(CH₂)₃— | \C=/ | =N— |
| H | OCH₂CH₂—OC₂H₅ | —(CH₂)₃— | \C=/ | =N— |
| H | O(CH₂CH₂O)₂—OC₂H₅ | —(CH₂)₃— | \C=/ | =N— |
| H | S—C₃H₇-n | —(CH₂)₃— | \C=/ | =N— |

TABLE 1-continued

Examples of the compounds of the formula (I)

| R¹ | R² | A | E | G |
|---|---|---|---|---|
| H | S—C₂H₅ | —(CH₂)₃— | \C=/ | =N— |
| H | S—CH₃ | —(CH₂)₃— | \C=/ | =N— |
| H | S—CH₂COOC₂H₅ | —(CH₂)₃— | \C=/ | =N— |
| H | SCH₂CH₂—COOC₂H₅ | —(CH₂)₃— | \C=/ | =N— |
| H | O—CH₂—C≡C—CH₃ | —(CH₂)₃— | \C=/ | =N— |
| H | OCH₂—CH=CH—Cl | —(CH₂)₃— | \C=/ | =N— |
| H | O—CH(CH₃)C≡CH | —(CH₂)₃— | \C=/ | =N— |
| H | OCH(CH₃)C≡C—CH₃ | —(CH₂)₃— | \C=/ | =N— |
| H | O—CH(CH₃)CH=CH₂ | —(CH₂)₃— | \C=/ | =N— |
| H | OCH₂CH=CH—CH₃ | —(CH₂)₃— | \C=/ | =N— |
| H | O—CH₃ | —(CH₂)₃— | \C=/ | =N— |
| H | O—C₂H₅ | —(CH₂)₃— | \C=/ | =N— |
| H | O—C₃H₇-n | —(CH₂)₃— | \C=/ | =N— |
| H | O—C₃H₇-iso | —(CH₂)₃— | \C=/ | =N— |
| H | O—□—COOC₂H₅ | —(CH₂)₃— | \C=/ | =N— |

TABLE 1-continued

Examples of the compounds of the formula (I)

| R¹ | R² | A | E | G |
|---|---|---|---|---|
| H | (tetrahydrofuran-3-yloxy) | $-(CH_2)_3-$ | $\backslash C= /$ | $=N-$ |
| H | $O-CH(CH_2F)_2$ | $-(CH_2)_3-$ | $\backslash C= /$ | $=N-$ |
| H | $O-CH_2-C(CH_3)=CH_2$ | $-(CH_2)_3-$ | $\backslash C= /$ | $=N-$ |
| H | (S-CH₂-tetrahydrofuran-2-yl) | $-(CH_2)_3-$ | $\backslash C= /$ | $=N-$ |
| H | (O-CH₂-tetrahydropyran-2-yl) | $-(CH_2)_3-$ | $\backslash C= /$ | $=N-$ |
| H | (O-cyclopropyl-COOC₂H₅) | $-(CH_2)_3-$ | $\backslash C= /$ | $=N-$ |
| H | (S-cyclobutyl-COOC₂H₅) | $-(CH_2)_3-$ | $\backslash C= /$ | $=N-$ |
| H | (S-cyclopropyl-COOC₂H₅) | $-(CH_2)_3-$ | $\backslash C= /$ | $=N-$ |
| H | $S-CH_2-COO$-cyclopentyl | $-(CH_2)_3-$ | $\backslash C= /$ | $=N-$ |
| H | $S-CH_2-COOC_5H_{11}\text{-n}$ | $-(CH_2)_3-$ | $\backslash C= /$ | $=N-$ |
| H | $O-CH_2$-phenyl | $-(CH_2)_3-$ | $\backslash C= /$ | $=N-$ |
| H | $S-CH_2$-phenyl | $-(CH_2)_3-$ | $\backslash C= /$ | $=N-$ |
| H | $O-CH_2CH_2-OCH(CH_2F)_2$ | $-(CH_2)_3-$ | $\backslash C= /$ | $=N-$ |
| H | $S-CH(CH_3)_2$ | $-(CH_2)_3-$ | $\backslash C= /$ | $=N-$ |

TABLE 1-continued

Examples of the compounds of the formula (I)

| R¹ | R² | A | E | G |
|----|----|---|---|---|
| H | O—CH₂—CCl=CH₂ | —(CH₂)₃— | \C=/ | =N— |
| H | O—(phenyl) | —(CH₂)₃— | \C=/ | =N— |
| H | O—CH₂CN | —(CH₂)₃— | \C=/ | =N— |
| H | O—CH₂COOC₄H₄—OCH₃ | —(CH₂)₃— | \C=/ | =N— |
| H | O—CH₂—COO—CH(CH₃)COOC₂H₅ | —(CH₂)₃— | \C=/ | =N— |
| H | OCH₂—COOCH₂—COOC₂H₅ | —(CH₂)₃— | \C=/ | =N— |
| H | O—CHF₂ | —(CH₂)₃— | \C=/ | =N— |
| H | O—CH₂CH₂—OCH₂CF₃ | —(CH₂)₃— | \C=/ | =N— |
| H | NHCH₃ | —(CH₂)₃— | \C=/ | =N— |
| H | NHC₂H₅ | —(CH₂)₃— | \C=/ | =N— |
| H | N(CH₃)₂ | —(CH₂)₃— | \C=/ | =N— |
| H | NH—CH₂—COOC₂H₅ | —(CH₂)₃— | \C=/ | =N— |
| H | piperidin-1-yl | —(CH₂)₃— | \C=/ | =N— |
| H | morpholin-4-yl | —(CH₂)₃— | \C=/ | =N— |
| H | NH—SO₂CH₃ | —(CH₂)₃— | \C=/ | =N— |

TABLE 1-continued

Examples of the compounds of the formula (I)

| R¹ | R² | A | E | G |
|---|---|---|---|---|
| H | NH—SO$_2$C$_2$H$_5$ | —(CH$_2$)$_3$— | \C=/ | =N— |
| H | NH—SO$_2$C$_3$H$_7$-n | —(CH$_2$)$_3$— | \C=/ | =N— |
| H | NH—SO$_2$C$_3$H$_7$-i | —(CH$_2$)$_3$— | \C=/ | =N— |
| H | NH—SO$_2$C$_4$H$_9$-n | —(CH$_2$)$_3$— | \C=/ | =N— |
| H | NH—SO$_2$C$_8$H$_{17}$-n | —(CH$_2$)$_3$— | \C=/ | =N— |
| H | NH—COCH$_3$ | —(CH$_2$)$_3$— | \C=/ | =N— |
| H | NH—COC$_2$H$_5$ | —(CH$_2$)$_3$— | \C=/ | =N— |
| H | NH—COCF$_3$ | —(CH$_2$)$_3$— | \C=/ | =N— |
| H | N(CH$_3$)—SO$_2$CH$_3$ | —(CH$_2$)$_3$— | \C=/ | =N— |
| H | N(CH$_3$)—SO$_2$C$_2$H$_5$ | —(CH$_2$)$_3$— | \C=/ | =N— |
| H | N(CH$_3$)—SO$_2$C$_3$H$_7$-n | —(CH$_2$)$_3$— | \C=/ | =N— |
| H | NH—SO$_2$CF$_3$ | —(CH$_2$)$_3$— | \C=/ | =N— |
| H | NH—SO$_2$—△ | —(CH$_2$)$_3$— | \C=/ | =N— |
| H | NH—SO$_2$—C$_4$H$_9$-n | —(CH$_2$)$_3$— | \C=/ | =N— |

TABLE 1-continued

Examples of the compounds of the formula (I)

| R¹ | R² | A | E | G |
|----|----|---|---|---|
| H | N(CH₃)SO₂CF₃ | —(CH₂)₃— | \C=/ | =N— |
| H | ⌬—NH—SO₂ | —(CH₂)₃— | \C=/ | =N— |
| H | ⌬—NH—SO₂CH₂ | —(CH₂)₃— | \C=/ | =N— |
| H | N(CH₃)—SO₂—⌬—CH₃ | —(CH₂)₃— | \C=/ | =N— |
| Cl | OCH₂CF₃ | —(CH₂)₃— | \C=/ | =N— |
| Cl | OCF₃ | —(CH₂)₃— | \C=/ | =N— |
| Cl | OCH₂CH(CH₃)—OC₂H₅ | —(CH₂)₃— | \C=/ | =N— |
| Cl | (tetrahydrofuran-2-yl-methoxy) O—CH₂ | —(CH₂)₃— | \C=/ | =N— |
| Cl | OCH₂—CH=CH₂ | —(CH₂)₃— | \C=/ | =N— |
| Cl | OH | —(CH₂)₃— | \C=/ | =N— |
| Cl | OCH₂—C≡CH | —(CH₂)₃— | \C=/ | =N— |
| Cl | SCH₂C≡CH | —(CH₂)₃— | \C=/ | =N— |
| Cl | OCH₂COOC₂H₅ | —(CH₂)₃— | \C=/ | =N— |
| Cl | S—C(CH₃)₃ | —(CH₂)₃— | \C=/ | =N— |
| Cl | OCH₂—COOC₅H₁₁-n | —(CH₂)₃— | \C=/ | =N— |

TABLE 1-continued

Examples of the compounds of the formula (I)

| R¹ | R² | A | E | G |
|----|----|----|----|----|
| Cl | OCH(CH₃)—COOC₂H₅ | —(CH₂)₃— | \C=/ | =N— |
| Cl | OCH₂CH₂—OCH₃ | —(CH₂)₃— | \C=/ | =N— |
| Cl | OCH₂CH₂—OC₂H₅ | —(CH₂)₃— | \C=/ | =N— |
| Cl | O(CH₂CH₂O)₂—OC₂H₅ | —(CH₂)₃— | \C=/ | =N— |
| Cl | S—C₃H₇-n | —(CH₂)₃— | \C=/ | =N— |
| Cl | S—C₂H₅ | —(CH₂)₃— | \C=/ | =N— |
| Cl | S—CH₃ | —(CH₂)₃— | \C=/ | =N— |
| Cl | S—CH₂COOC₂H₅ | —(CH₂)₃— | \C=/ | =N— |
| Cl | SCH₂CH₂—COOC₂H₅ | —(CH₂)₃— | \C=/ | =N— |
| Cl | O—CH₂—C≡C—CH₃ | —(CH₂)₃— | \C=/ | =N— |
| Cl | OCH₂—CH=CH—Cl | —(CH₂)₃— | \C=/ | =N— |
| Cl | O—CH(CH₃)C≡CH | —(CH₂)₃— | \C=/ | =N— |
| Cl | OCH(CH₃)C≡C—CH₃ | —(CH₂)₃— | \C=/ | =N— |
| Cl | O—CH(CH₃)CH=CH₂ | —(CH₂)₃— | \C=/ | =N— |

TABLE 1-continued

Examples of the compounds of the formula (I)

| R¹ | R² | A | E | G |
|---|---|---|---|---|
| Cl | OCH$_2$CH=CH—CH$_3$ | —(CH$_2$)$_3$— | \C= | =N— |
| Cl | O—CH$_3$ | —(CH$_2$)$_3$— | \C= | =N— |
| Cl | O—C$_2$H$_5$ | —(CH$_2$)$_3$— | \C= | =N— |
| Cl | O—C$_3$H$_7$-n | —(CH$_2$)$_3$— | \C= | =N— |
| Cl | O—C$_3$H$_7$-iso | —(CH$_2$)$_3$— | \C= | =N— |
| Cl | O—[cyclobutyl-COOC$_2$H$_5$] | —(CH$_2$)$_3$— | \C= | =N— |
| Cl | —O—[tetrahydrofuran-2-yl via CH]—O | —(CH$_2$)$_3$— | \C= | =N— |
| Cl | O—CH(CH$_2$F)$_2$ | —(CH$_2$)$_3$— | \C= | =N— |
| Cl | O—CH$_2$—C(CH$_3$)=CH$_2$ | —(CH$_2$)$_3$— | \C= | =N— |
| Cl | S—CH$_2$—[tetrahydrofuran-2-yl] | —(CH$_2$)$_3$— | \C= | =N— |
| Cl | O—CH$_2$—[tetrahydropyran-2-yl] | —(CH$_2$)$_3$— | \C= | =N— |
| Cl | O—[cyclopropyl-COOC$_2$H$_5$] | —(CH$_2$)$_3$— | \C= | =N— |
| Cl | —S—[cyclobutyl-COOC$_2$H$_5$] | —(CH$_2$)$_3$— | \C= | =N— |
| Cl | S—[cyclopropyl-COOC$_2$H$_5$] | —(CH$_2$)$_3$— | \C= | =N— |
| Cl | S—CH$_2$—COO—[cyclopentyl] | —(CH$_2$)$_3$— | \C= | =N— |

TABLE 1-continued

Examples of the compounds of the formula (I)

| R¹ | R² | A | E | G |
|---|---|---|---|---|
| Cl | S—CH₂—COOC₅H₁₁-n | —(CH₂)₃— | \C= | =N— |
| Cl | O—CH₂—C₆H₅ | —(CH₂)₃— | \C= | =N— |
| Cl | S—CH₂—C₆H₅ | —(CH₂)₃— | \C= | =N— |
| Cl | O—CH₂CH₂—OCH(CH₂F)₂ | —(CH₂)₃— | \C= | =N— |
| Cl | S—CH(CH₃)₂ | —(CH₂)₃— | \C= | =N— |
| Cl | O—CH₂—CCl=CH₂ | —(CH₂)₃— | \C= | =N— |
| Cl | O—C₆H₅ | —(CH₂)₃— | \C= | =N— |
| Cl | O—CH₂CN | —(CH₂)₃— | \C= | =N— |
| Cl | O—CH₂COOC₂H₄—OCH₃ | —(CH₂)₃— | \C= | =N— |
| Cl | O—CH₂—COO—CH(CH₃)COOC₂H₅ | —(CH₂)₃— | \C= | =N— |
| Cl | OCH₂—COOCH₂—COOC₂H₅ | —(CH₂)₃— | \C= | =N— |
| Cl | O—CHF₂ | —(CH₂)₃— | \C= | =N— |
| Cl | O—CH₂CH₂—OCH₂CF₃ | —(CH₂)₃— | \C= | =N— |
| Cl | NHCH₃ | —(CH₂)₃— | \C= | =N— |

TABLE 1-continued

Examples of the compounds of the formula (I)

| R¹ | R² | A | E | G |
|---|---|---|---|---|
| Cl | NHC₂H₅ | —(CH₂)₃— | \C=/ | =N— |
| Cl | N(CH₃)₂ | —(CH₂)₃— | \C=/ | =N— |
| Cl | NH—CH₂—COOC₂H₅ | —(CH₂)₃— | \C=/ | =N— |
| Cl | 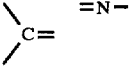 (piperidinyl) | —(CH₂)₃— | \C=/ | =N— |
| Cl | 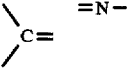 (morpholinyl) | —(CH₂)₃— | \C=/ | =N— |
| Cl | NH—SO₂CH₃ | —(CH₂)₃— | \C=/ | =N— |
| Cl | NH—SO₂C₂H₅ | —(CH₂)₃— | \C=/ | =N— |
| Cl | NH—SO₂C₃H₇-n | —(CH₂)₃— | \C=/ | =N— |
| Cl | NH—SO₂C₃H₇-i | —(CH₂)₃— | \C=/ | =N— |
| Cl | NH—SO₂C₄H₉-n | —(CH₂)₃— | \C=/ | =N— |
| Cl | NH—SO₂C₈H₁₇-n | —(CH₂)₃— | \C=/ | =N— |
| Cl | NH—COCH₃ | —(CH₂)₃— | \C=/ | =N— |
| Cl | NH—COC₂H₅ | —(CH₂)₃— | \C=/ | =N— |
| Cl | NH—COCF₃ | —(CH₂)₃— | \C=/ | =N— |
| Cl | N(CH₃)—SO₂CH₃ | —(CH₂)₃— | \C=/ | =N— |

TABLE 1-continued

Examples of the compounds of the formula (I)

| R¹ | R² | A | E | G |
|---|---|---|---|---|
| Cl | N(CH₃)—SO₂C₂H₅ | —(CH₂)₃— | \C=/ | =N— |
| Cl | N(CH₃)—SO₂C₃H₇-n | —(CH₂)₃— | \C=/ | =N— |
| Cl | NH—SO₂CF₃ | —(CH₂)₃— | \C=/ | =N— |
| Cl | NH—SO₂—△ | —(CH₂)₃— | \C=/ | =N— |
| Cl | NH—SO₂—C₄F₉-n | —(CH₂)₃— | \C=/ | =N— |
| Cl | N(CH₃)SO₂CF₃ | —(CH₂)₃— | \C=/ | =N— |
| Cl | NH—SO₂—C₆H₅ | —(CH₂)₃— | \C=/ | =N— |
| Cl | NH—SO₂CH₂—C₆H₅ | —(CH₂)₃— | \C=/ | =N— |
| Cl | N(CH₃)—SO₂—C₆H₄—CH₃ | —(CH₂)₃— | \C=/ | =N— |
| F | O—CH(CH₂F)₂ | —CH₂C(CH₃)₂—CH₂— | \C=/ | =N— |
| F | O—CH₂—C(CH₃)=CH₂ | —CH₂C(CH₃)₂—CH₂— | \C=/ | =N— |
| F | S—CH₂-(tetrahydrofuran-2-yl) | —CH₂C(CH₃)₂—CH₂— | \C=/ | =N— |
| F | O—CH₂-(tetrahydropyran-2-yl) | —CH₂C(CH₃)₂—CH₂— | \C=/ | =N— |
| F | O—C(cyclopropyl)(COOC₂H₅) | —CH₂C(CH₃)₂—CH₂— | \C=/ | =N— |

TABLE 1-continued

Examples of the compounds of the formula (I)

| R¹ | R² | A | E | G |
|---|---|---|---|---|
| F | 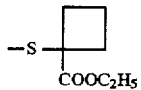 —S—[cyclobutyl-COOC₂H₅] | —CH₂C(CH₃)₂—CH₂— | \C=/ | =N— |
| F |  S—[cyclopropyl-COOC₂H₅] | —CH₂C(CH₃)₂—CH₂— | \C=/ | =N— |
| F |  S—CH₂—COO—[cyclopentyl] | —CH₂C(CH₃)₂—CH₂— | \C=/ | =N— |
| F | S—CH₂—COOC₅H₁₁-n | —CH₂C(CH₃)₂—CH₂— | \C=/ | =N— |
| F |  O—CH₂—[phenyl] | —CH₂C(CH₃)₂—CH₂— | \C=/ | =N— |
| F | 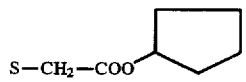 S—CH₂—[phenyl] | —CH₂C(CH₃)₂—CH₂— | \C=/ | =N— |
| F | O—CH₂CH₂—OCH(CH₂F)₂ | —CH₂C(CH₃)₂—CH₂— | \C=/ | =N— |
| F | S—CH(CH₃)₂ | —CH₂C(CH₃)₂—CH₂— | \C=/ | =N— |
| F | O—CH₂—CCl=CH₂ | —CH₂C(CH₃)₂—CH₂— | \C=/ | =N— |
| F |  O—[phenyl] | —CH₂C(CH₃)₂—CH₂— | \C=/ | =N— |
| F | O—CH₂CN | —CH₂C(CH₃)₂—CH₂— | \C=/ | =N— |
| F | O—CH₂COOC₂H₄—OCH₃ | —CH₂C(CH₃)₂—CH₂— | \C=/ | =N— |
| F | O—CH₂—COO—CH(CH₃)COOC₂H₅ | —CH₂C(CH₃)₂—CH₂— | \C=/ | =N— |
| F | OCH₂—COOCH₂—COOC₂H₅ | —CH₂C(CH₃)₂—CH₂— | \C=/ | =N— |
| F | O—CHF₂ | —CH₂C(CH₃)₂—CH₂— | \C=/ | =N— |

TABLE 1-continued

Examples of the compounds of the formula (I)

| R¹ | R² | A | E | G |
|---|---|---|---|---|
| F | O—CH₂CH₂—OCH₂CF₃ | —CH₂C(CH₃)₂—CH₂— | \C=/ | =N— |
| F | OCH₂CF₃ | —CH₂C(CH₃)₂—CH₂— | \C=/ | =N— |
| F | OCF₃ | —CH₂C(CH₃)₂—CH₂— | \C=/ | =N— |
| F | OCH₂CH(CH₃)—OC₂H₅ | —CH₂C(CH₃)₂—CH₂— | \C=/ | =N— |
| F | (tetrahydrofuran-2-ylmethoxy) | —CH₂C(CH₃)₂—CH₂— | \C=/ | =N— |
| F | OCH₂—CH=CH₂ | —CH₂C(CH₃)₂—CH₂— | \C=/ | =N— |
| F | OH | —CH₂C(CH₃)₂—CH₂— | \C=/ | =N— |
| F | OCH₂—C≡CH | —CH₂C(CH₃)₂—CH₂— | \C=/ | =N— |
| F | SCH₂C≡CH | —CH₂C(CH₃)₂—CH₂— | \C=/ | =N— |
| F | OCH₂COOC₂H₅ | —CH₂C(CH₃)₂—CH₂— | \C=/ | =N— |
| F | S—C(CH₃)₃ | —CH₂C(CH₃)₂—CH₂— | \C=/ | =N— |
| F | OCH₂—COOC₅H₁₁-n | —CH₂C(CH₃)₂—CH₂— | \C=/ | =N— |
| F | OCH(CH₃)—COOC₂H₅ | —CH₂C(CH₃)₂—CH₂— | \C=/ | =N— |
| F | OCH₂CH₂—OCH₃ | —CH₂C(CH₃)₂—CH₂— | \C=/ | =N— |

TABLE 1-continued

Examples of the compounds of the formula (I)

| R¹ | R² | A | E | G |
|---|---|---|---|---|
| F | OCH$_2$CH$_2$—OC$_2$H$_5$ | —CH$_2$C(CH$_3$)$_2$—CH$_2$— | \C=/ | =N— |
| F | O(CH$_2$CH$_2$O)$_2$—OC$_2$H$_5$ | —CH$_2$C(CH$_3$)$_2$—CH$_2$— | \C=/ | =N— |
| F | S—C$_3$H$_7$-n | —CH$_2$C(CH$_3$)$_2$—CH$_2$— | \C=/ | =N— |
| F | S—C$_2$H$_5$ | —CH$_2$C(CH$_3$)$_2$—CH$_2$— | \C=/ | =N— |
| F | S—CH$_3$ | —CH$_2$C(CH$_3$)$_2$—CH$_2$— | \C=/ | =N— |
| F | S—CH$_2$COOC$_2$H$_5$ | —CH$_2$C(CH$_3$)$_2$—CH$_2$— | \C=/ | =N— |
| F | SCH$_2$CH$_2$—COOC$_2$H$_5$ | —CH$_2$C(CH$_3$)$_2$—CH$_2$— | \C=/ | =N— |
| F | O—CH$_2$—C≡C—CH$_3$ | —CH$_2$C(CH$_3$)$_2$—CH$_2$— | \C=/ | =N— |
| F | OCH$_2$—CH=CH—Cl | —CH$_2$C(CH$_3$)$_2$—CH$_2$— | \C=/ | =N— |
| F | O—CH(CH$_3$)C≡CH | —CH$_2$C(CH$_3$)$_2$—CH$_2$— | \C=/ | =N— |
| F | OCH(CH$_3$)C≡C—CH$_3$ | —CH$_2$C(CH$_3$)$_2$—CH$_2$— | \C=/ | =N— |
| F | O—CH(CH$_3$)CH=CH$_2$ | —CH$_2$C(CH$_3$)$_2$—CH$_2$— | \C=/ | =N— |
| F | OCH$_2$CH=CH—CH$_3$ | —CH$_2$C(CH$_3$)$_2$—CH$_2$— | \C=/ | =N— |
| F | O—CH$_3$ | —CH$_2$C(CH$_3$)$_2$—CH$_2$— | \C=/ | =N— |
| F | O—C$_2$H$_5$ | —CH$_2$C(CH$_3$)$_2$—CH$_2$— | \C=/ | =N— |

TABLE 1-continued

Examples of the compounds of the formula (I)

| R¹ | R² | A | E | G |
|---|---|---|---|---|
| F | O—C₃H₇-n | —CH₂C(CH₃)₂—CH₂— | \C=/ | =N— |
| F | O—C₃H₇-iso | —CH₂C(CH₃)₂—CH₂— | \C=/ | =N— |
| F | 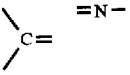 | —CH₂C(CH₃)₂—CH₂— | \C=/ | =N— |
| F | 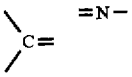 | —CH₂C(CH₃)₂—CH₂— | \C=/ | =N— |
| F | NHCH₃ | —CH₂C(CH₃)₂—CH₂— | \C=/ | =N— |
| F | NHC₂H₅ | —CH₂C(CH₃)₂—CH₂— | \C=/ | =N— |
| F | N(CH₃)₂ | —CH₂C(CH₃)₂—CH₂— | \C=/ | =N— |
| F | NH—CH₂—COOC₂H₅ | —CH₂C(CH₃)₂—CH₂— | \C=/ | =N— |
| F | 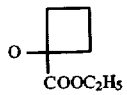 | —CH₂C(CH₃)₂—CH₂— | \C=/ | =N— |
| F | 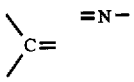 | —CH₂C(CH₃)₂—CH₂— | \C=/ | =N— |
| F | NH—SO₂CH₃ | —CH₂C(CH₃)₂—CH₂— | \C=/ | =N— |
| F | NH—SO₂C₂H₅ | —CH₂C(CH₃)₂—CH₂— | \C=/ | =N— |
| F | NH—SO₂C₃H₇-n | —CH₂C(CH₃)₂—CH₂— | \C=/ | =N— |
| F | NH—SO₂C₃H₇-i | —CH₂C(CH₃)₂—CH₂— | \C=/ | =N— |

TABLE 1-continued

Examples of the compounds of the formula (I)

| R¹ | R² | A | E | G |
|---|---|---|---|---|
| F | NH—SO$_2$C$_4$H$_9$-n | —CH$_2$C(CH$_3$)$_2$—CH$_2$— | \C= / | =N— |
| F | NH—SO$_2$C$_8$H$_{17}$-n | —CH$_2$C(CH$_3$)$_2$—CH$_2$— | \C= / | =N— |
| F | NH—COCH$_3$ | —CH$_2$C(CH$_3$)$_2$—CH$_2$— | \C= / | =N— |
| F | NH—COC$_2$H$_5$ | —CH$_2$C(CH$_3$)$_2$—CH$_2$— | \C= / | =N— |
| F | NH—COCF$_3$ | —CH$_2$C(CH$_3$)$_2$—CH$_2$— | \C= / | =N— |
| F | N(CH$_3$)—SO$_2$CH$_3$ | —CH$_2$C(CH$_3$)$_2$—CH$_2$— | \C= / | =N— |
| F | N(CH$_3$)—SO$_2$C$_2$H$_5$ | —CH$_2$C(CH$_3$)$_2$—CH$_2$— | \C= / | =N— |
| F | N(CH$_3$)—SO$_2$C$_3$H$_7$-n | —CH$_2$C(CH$_3$)$_2$—CH$_2$— | \C= / | =N— |
| F | NH—SO$_2$CF$_3$ | —CH$_2$C(CH$_3$)$_2$—CH$_2$— | \C= / | =N— |
| F | NH—SO$_2$—△ | —CH$_2$C(CH$_3$)$_2$—CH$_2$— | \C= / | =N— |
| F | NH—SO$_2$—C$_4$F$_9$-n | —CH$_2$C(CH$_3$)$_2$—CH$_2$— | \C= / | =N— |
| F | N(CH$_3$)SO$_2$CF$_3$ | —CH$_2$C(CH$_3$)$_2$—CH$_2$— | \C= / | =N— |
| F | NH—SO$_2$—C$_6$H$_5$ | —CH$_2$C(CH$_3$)$_2$—CH$_2$— | \C= / | =N— |
| F | NH—SO$_2$CH$_2$—C$_6$H$_5$ | —CH$_2$C(CH$_3$)$_2$—CH$_2$— | \C= / | =N— |
| F | N(CH$_3$)—SO$_2$—C$_6$H$_4$—CH$_3$ | —CH$_2$C(CH$_3$)$_2$—CH$_2$— | \C= / | =N— |

TABLE 1-continued

Examples of the compounds of the formula (I)

| R¹ | R² | A | E | G |
|---|---|---|---|---|
| H | OCH$_2$CF$_3$ | —CH$_2$C(CH$_3$)$_2$—CH$_2$— | \C= | =N— |
| H | OCF$_3$ | —CH$_2$C(CH$_3$)$_2$—CH$_2$— | \C= | =N— |
| H | OCH$_2$CH(CH$_3$)—OC$_2$H$_5$ | —CH$_2$C(CH$_3$)$_2$—CH$_2$— | \C= | =N— |
| H | 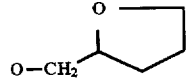 | —CH$_2$C(CH$_3$)$_2$—CH$_2$— | \C= | =N— |
| H | OCH$_2$—CH=CH$_2$ | —CH$_2$C(CH$_3$)$_2$—CH$_2$— | \C= | =N— |
| H | OH | —CH$_2$C(CH$_3$)$_2$—CH$_2$— | \C= | =N— |
| H | OCH$_2$—C≡CH | —CH$_2$C(CH$_3$)$_2$—CH$_2$— | \C= | =N— |
| H | SCH$_2$C≡CH | —CH$_2$C(CH$_3$)$_2$—CH$_2$— | \C= | =N— |
| H | OCH$_2$COOC$_2$H$_5$ | —CH$_2$C(CH$_3$)$_2$—CH$_2$— | \C= | =N— |
| H | S—C(CH$_3$)$_3$ | —CH$_2$C(CH$_3$)$_2$—CH$_2$— | \C= | =N— |
| H | OCH$_2$—COOC$_5$H$_{11}$-n | —CH$_2$C(CH$_3$)$_2$—CH$_2$— | \C= | =N— |
| H | OCH(CH$_3$)—COOC$_2$H$_5$ | —CH$_2$C(CH$_3$)$_2$—CH$_2$— | \C= | =N— |
| H | OCH$_2$CH$_2$—OCH$_3$ | —CH$_2$C(CH$_3$)$_2$—CH$_2$— | \C= | =N— |
| H | OCH$_2$CH$_2$—OC$_2$H$_5$ | —CH$_2$C(CH$_3$)$_2$—CH$_2$— | \C= | =N— |

TABLE 1-continued

Examples of the compounds of the formula (I)

| R¹ | R² | A | E | G |
|---|---|---|---|---|
| H | O(CH₂CH₂O)₂—OC₂H₅ | —CH₂C(CH₃)₂—CH₂— | \C= / | =N— |
| H | S—C₃H₇-n | —CH₂C(CH₃)₂—CH₂— | \C= / | =N— |
| H | S—C₂H₅ | —CH₂C(CH₃)₂—CH₂— | \C= / | =N— |
| H | S—CH₃ | —CH₂C(CH₃)₂—CH₂— | \C= / | =N— |
| H | S—CH₂COOC₂H₅ | —CH₂C(CH₃)₂—CH₂— | \C= / | =N— |
| H | SCH₂CH₂—COOC₂H₅ | —CH₂C(CH₃)₂—CH₂— | \C= / | =N— |
| H | O—CH₂—C≡C—CH₃ | —CH₂C(CH₃)₂—CH₂— | \C= / | =N— |
| H | OCH₂—CH=CH—Cl | —CH₂C(CH₃)₂—CH₂— | \C= / | =N— |
| H | O—CH(CH₃)C≡CH | —CH₂C(CH₃)₂—CH₂— | \C= / | =N— |
| H | OCH(CH₃)C≡C—CH₃ | —CH₂C(CH₃)₂—CH₂— | \C= / | =N— |
| H | O—CH(CH₃)CH=CH₂ | —CH₂C(CH₃)₂—CH₂— | \C= / | =N— |
| H | OCH₂CH=CH—CH₃ | —CH₂C(CH₃)₂—CH₂— | \C= / | =N— |
| H | O—CH₃ | —CH₂C(CH₃)₂—CH₂— | \C= / | =N— |
| H | O—C₂H₅ | —CH₂C(CH₃)₂—CH₂— | \C= / | =N— |
| H | O—C₃H₇-n | —CH₂C(CH₃)₂—CH₂— | \C= / | =N— |

TABLE 1-continued

Examples of the compounds of the formula (I)

| R¹ | R² | A | E | G |
|---|---|---|---|---|
| H | O—C₃H₇-iso | —CH₂C(CH₃)₂—CH₂— | \C=/ | =N— |
| H | ![cyclobutane with O and COOC₂H₅] | —CH₂C(CH₃)₂—CH₂— | \C=/ | =N— |
| H | ![tetrahydrofuran with —O—] | —CH₂C(CH₃)₂—CH₂— | \C=/ | =N— |
| H | O—CH(CH₂F)₂ | —CH₂C(CH₃)₂—CH₂— | \C=/ | =N— |
| H | O—CH₂—C(CH₃)=CH₂ | —CH₂C(CH₃)₂—CH₂— | \C=/ | =N— |
| H | ![S—CH₂-tetrahydrofuran] | —CH₂C(CH₃)₂—CH₂— | \C=/ | =N— |
| H | ![O—CH₂-tetrahydropyran] | —CH₂C(CH₃)₂—CH₂— | \C=/ | =N— |
| H | ![cyclopropane with O and COOC₂H₅] | —CH₂C(CH₃)₂—CH₂— | \C=/ | =N— |
| H | ![cyclobutane with —S and COOC₂H₅] | —CH₂C(CH₃)₂—CH₂— | \C=/ | =N— |
| H | ![cyclopropane with S and COOC₂H₅] | —CH₂C(CH₃)₂—CH₂— | \C=/ | =N— |
| H | S—CH₂—COO-cyclopentyl | —CH₂C(CH₃)₂—CH₂— | \C=/ | =N— |
| H | S—CH₂COOC₅H₁₁-n | —CH₂C(CH₃)₂—CH₂— | \C=/ | =N— |
| H | O—CH₂—C₆H₅ | —CH₂C(CH₃)₂—CH₂— | \C=/ | =N— |
| H | S—CH₂—C₆H₅ | —CH₂C(CH₃)₂—CH₂— | \C=/ | =N— |

TABLE 1-continued

Examples of the compounds of the formula (I)

| R¹ | R² | A | E | G |
|---|---|---|---|---|
| H | O—CH₂CH₂—OCH(CH₂F)₂ | —CH₂C(CH₃)₂—CH₂— | \C=/ | =N— |
| H | S—CH(CH₃)₂ | —CH₂C(CH₃)₂—CH₂— | \C=/ | =N— |
| H | O—CH₂—CCl=CH₂ | —CH₂C(CH₃)₂—CH₂— | \C=/ | =N— |
| H | O—C₆H₅ | —CH₂C(CH₃)₂—CH₂— | \C=/ | =N— |
| H | O—CH₂CN | —CH₂C(CH₃)₂—CH₂— | \C=/ | =N— |
| H | O—CH₂COOC₂H₄—OCH₃ | —CH₂C(CH₃)₂—CH₂— | \C=/ | =N— |
| H | O—CH₂—COO—CH(CH₃)COOC₂H₅ | —CH₂C(CH₃)₂—CH₂— | \C=/ | =N— |
| H | OCH₂—COOCH₂—COOC₂H₅ | —CH₂C(CH₃)₂—CH₂— | \C=/ | =N— |
| H | O—CHF₂ | —CH₂C(CH₃)₂—CH₂— | \C=/ | =N— |
| H | O—CH₂CH₂—OCH₂CF₃ | —CH₂C(CH₃)₂—CH₂— | \C=/ | =N— |
| H | NHCH₃ | —CH₂C(CH₃)₂—CH₂— | \C=/ | =N— |
| H | NHC₂H₅ | —CH₂C(CH₃)₂—CH₂— | \C=/ | =N— |
| H | N(CH₃)₂ | —CH₂C(CH₃)₂—CH₂— | \C=/ | =N— |
| H | NH—CH₂—COOC₂H₅ | —CH₂C(CH₃)₂—CH₂— | \C=/ | =N— |
| H | piperidin-1-yl | —CH₂C(CH₃)₂—CH₂— | \C=/ | =N— |

TABLE 1-continued

Examples of the compounds of the formula (I)

| R¹ | R² | A | E | G |
|---|---|---|---|---|
| H | morpholino (N—O ring) | $-CH_2C(CH_3)_2-CH_2-$ | $\backslash C=/$ | $=N-$ |
| H | $NH-SO_2CH_3$ | $-CH_2C(CH_3)_2-CH_2-$ | $\backslash C=/$ | $=N-$ |
| H | $NH-SO_2C_2H_5$ | $-CH_2C(CH_3)_2-CH_2-$ | $\backslash C=/$ | $=N-$ |
| H | $NH-SO_2C_3H_7\text{-}n$ | $-CH_2C(CH_3)_2-CH_2-$ | $\backslash C=/$ | $=N-$ |
| H | $NH-SO_2C_3H_7\text{-}i$ | $-CH_2C(CH_3)_2-CH_2-$ | $\backslash C=/$ | $=N-$ |
| H | $NH-SO_2C_4H_9\text{-}n$ | $-CH_2C(CH_3)_2-CH_2-$ | $\backslash C=/$ | $=N-$ |
| H | $NH-SO_2C_8H_{17}\text{-}n$ | $-CH_2C(CH_3)_2-CH_2-$ | $\backslash C=/$ | $=N-$ |
| H | $NH-COCH_3$ | $-CH_2C(CH_3)_2-CH_2-$ | $\backslash C=/$ | $=N-$ |
| H | $NH-COC_2H_5$ | $-CH_2C(CH_3)_2-CH_2-$ | $\backslash C=/$ | $=N-$ |
| H | $NH-COCF_3$ | $-CH_2C(CH_3)_2-CH_2-$ | $\backslash C=/$ | $=N-$ |
| H | $N(CH_3)-SO_2CH_3$ | $-CH_2C(CH_3)_2-CH_2-$ | $\backslash C=/$ | $=N-$ |
| H | $N(CH_3)-SO_2C_2H_5$ | $-CH_2C(CH_3)_2-CH_2-$ | $\backslash C=/$ | $=N-$ |
| H | $N(CH_3)-SO_2C_3H_7\text{-}n$ | $-CH_2C(CH_3)_2-CH_2-$ | $\backslash C=/$ | $=N-$ |
| H | $NH-SO_2CF_3$ | $-CH_2C(CH_3)_2-CH_2-$ | $\backslash C=/$ | $=N-$ |

TABLE 1-continued

Examples of the compounds of the formula (I)

| R¹ | R² | A | E | G |
|---|---|---|---|---|
| H | NH—SO₂—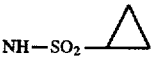 | —CH₂C(CH₃)₂—CH₂— | C= | =N— |
| H | NH—SO₂—C₄F₉-n | —CH₂C(CH₃)₂—CH₂— | C= | =N— |
| H | N(CH₃)SO₂CF₃ | —CH₂C(CH₃)₂—CH₂— | C= | =N— |
| H | NH—SO₂—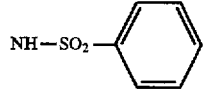 | —CH₂C(CH₃)₂—CH₂— | C= | =N— |
| H | NH—SO₂CH₂—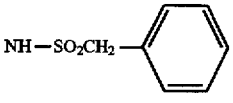 | —CH₂C(CH₃)₂—CH₂— | C= | =N— |
| H | N(CH₃)—SO₂—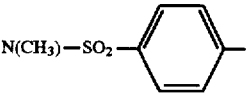—CH₃ | —CH₂C(CH₃)₂—CH₂— | C= | =N— |
| Cl | OCH₂CF₃ | —CH₂C(CH₃)₂—CH₂— | C= | =N— |
| Cl | OCF₃ | —CH₂C(CH₃)₂—CH₂— | C= | =N— |
| Cl | OCH₂CH(CH₃)—OC₂H₅ | —CH₂C(CH₃)₂—CH₂— | C= | =N— |
| Cl | 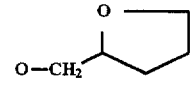 | —CH₂C(CH₃)₂—CH₂— | C= | =N— |
| Cl | OCH₂—CH=CH₂ | —CH₂C(CH₃)₂—CH₂— | C= | =N— |
| Cl | OH | —CH₂C(CH₃)₂—CH₂— | C= | =N— |
| Cl | OCH₂—C≡CH | —CH₂C(CH₃)₂—CH₂— | C= | =N— |
| Cl | SCH₂C≡CH | —CH₂C(CH₃)₂—CH₂— | C= | =N— |
| Cl | OCH₂COOC₂H₅ | —CH₂C(CH₃)₂—CH₂— | C= | =N— |

TABLE 1-continued

Examples of the compounds of the formula (I)

| R¹ | R² | A | E | G |
|---|---|---|---|---|
| Cl | S—C(CH₃)₃ | —CH₂C(CH₃)₂—CH₂— | \C=/ | =N— |
| Cl | OCH₂—COOC₅H₁₁-n | —CH₂C(CH₃)₂—CH₂— | \C=/ | =N— |
| Cl | OCH(CH₃)—COOC₂H₅ | —CH₂C(CH₃)₂—CH₂— | \C=/ | =N— |
| Cl | OCH₂CH₂—OCH₃ | —CH₂C(CH₃)₂—CH₂— | \C=/ | =N— |
| Cl | OCH₂CH₂—OC₂H₅ | —CH₂C(CH₃)₂—CH₂— | \C=/ | =N— |
| Cl | O(CH₂CH₂O)₂—OC₂H₅ | —CH₂C(CH₃)₂—CH₂— | \C=/ | =N— |
| Cl | S—C₃H₇-n | —CH₂C(CH₃)₂—CH₂— | \C=/ | =N— |
| Cl | S—C₂H₅ | —CH₂C(CH₃)₂—CH₂— | \C=/ | =N— |
| Cl | S—CH₃ | —CH₂C(CH₃)₂—CH₂— | \C=/ | =N— |
| Cl | S—CH₂COOC₂H₅ | —CH₂C(CH₃)₂—CH₂— | \C=/ | =N— |
| Cl | SCH₂CH₂—COOC₂H₅ | —CH₂C(CH₃)₂—CH₂— | \C=/ | =N— |
| Cl | O—CH₂—C≡C—CH₃ | —CH₂C(CH₃)₂—CH₂— | \C=/ | =N— |
| Cl | OCH₂—CH=CH—Cl | —CH₂C(CH₃)₂—CH₂— | \C=/ | =N— |
| Cl | O—CH(CH₃)C≡CH | —CH₂C(CH₃)₂—CH₂— | \C=/ | =N— |

TABLE 1-continued

Examples of the compounds of the formula (I)

| R¹ | R² | A | E | G |
|---|---|---|---|---|
| Cl | OCH(CH₃)C≡C—CH₃ | —CH₂C(CH₃)₂—CH₂— | \C=/ | =N— |
| Cl | O—CH(CH₃)CH=CH₂ | —CH₂C(CH₃)₂—CH₂— | \C=/ | =N— |
| Cl | OCH₂CH=CH—CH₃ | —CH₂C(CH₃)₂—CH₂— | \C=/ | =N— |
| Cl | O—CH₃ | —CH₂C(CH₃)₂—CH₂— | \C=/ | =N— |
| Cl | O—C₂H₅ | —CH₂C(CH₃)₂—CH₂— | \C=/ | =N— |
| Cl | O—C₃H₇-n | —CH₂C(CH₃)₂—CH₂— | \C=/ | =N— |
| Cl | O—C₃H₇-iso | —CH₂C(CH₃)₂—CH₂— | \C=/ | =N— |
| Cl | 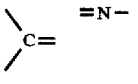 | —CH₂C(CH₃)₂—CH₂— | \C=/ | =N— |
| Cl | 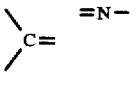 | —CH₂C(CH₃)₂—CH₂— | \C=/ | =N— |
| Cl | O—CH(CH₂F)₂ | —CH₂C(CH₃)₂—CH₂— | \C=/ | =N— |
| Cl | O—CH₂—C(CH₃)=CH₂ | —CH₂C(CH₃)₂—CH₂— | \C=/ | =N— |
| Cl | 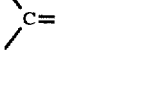 | —CH₂C(CH₃)₂—CH₂— | \C=/ | =N— |
| Cl | 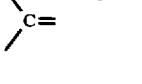 | —CH₂C(CH₃)₂—CH₂— | \C=/ | =N— |
| Cl | 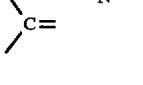 | —CH₂C(CH₃)₂—CH₂— | \C=/ | =N— |
| Cl | 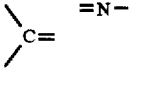 | —CH₂C(CH₃)₂—CH₂— | \C=/ | =N— |

TABLE 1-continued

Examples of the compounds of the formula (I)

| R¹ | R² | A | E | G |
|---|---|---|---|---|
| Cl | S—△—COOC₂H₅ (cyclopropyl with S and COOC₂H₅) | —CH₂C(CH₃)₂—CH₂— | \C=/ | =N— |
| Cl | S—CH₂—COO—(cyclopentyl) | —CH₂C(CH₃)₂—CH₂— | \C=/ | =N— |
| Cl | S—CH₂—COOC₅H₁₁-n | —CH₂C(CH₃)₂—CH₂— | \C=/ | =N— |
| Cl | O—CH₂—(phenyl) | —CH₂C(CH₃)₂—CH₂— | \C=/ | =N— |
| Cl | S—CH₂—(phenyl) | —CH₂C(CH₃)₂—CH₂— | \C=/ | =N— |
| Cl | O—CH₂CH₂—OCH(CH₂F)₂ | —CH₂C(CH₃)₂—CH₂— | \C=/ | =N— |
| Cl | S—CH(CH₃)₂ | —CH₂C(CH₃)₂—CH₂— | \C=/ | =N— |
| Cl | O—CH₂—CCl=CH₂ | —CH₂C(CH₃)₂—CH₂— | \C=/ | =N— |
| Cl | O—(phenyl) | —CH₂C(CH₃)₂—CH₂— | \C=/ | =N— |
| Cl | O—CH₂CN | —CH₂C(CH₃)₂—CH₂— | \C=/ | =N— |
| Cl | O—CH₂COOC₂H₄—OCH₃ | —CH₂C(CH₃)₂—CH₂— | \C=/ | =N— |
| Cl | O—CH₂—COO—CH(CH₃)COOC₂H₅ | —CH₂C(CH₃)₂—CH₂— | \C=/ | =N— |
| Cl | OCH₂—COOCH₂—COOC₂H₅ | —CH₂C(CH₃)₂—CH₂— | \C=/ | =N— |
| Cl | O—CHF₂ | —CH₂C(CH₃)₂—CH₂— | \C=/ | =N— |

TABLE 1-continued

Examples of the compounds of the formula (I)

| $R^1$ | $R^2$ | A | E | G |
|---|---|---|---|---|
| Cl | O—CH$_2$CH$_2$—OCH$_2$CF$_3$ | —CH$_2$C(CH$_3$)$_2$—CH$_2$— | \C=/ | =N— |
| Cl | NHCH$_3$ | —CH$_2$C(CH$_3$)$_2$—CH$_2$— | \C=/ | =N— |
| Cl | NHC$_2$H$_5$ | —CH$_2$C(CH$_3$)$_2$—CH$_2$— | \C=/ | =N— |
| Cl | N(CH$_3$)$_2$ | —CH$_2$C(CH$_3$)$_2$—CH$_2$— | \C=/ | =N— |
| Cl | NH—CH$_2$—COOC$_2$H$_5$ | —CH$_2$C(CH$_3$)$_2$—CH$_2$— | \C=/ | =N— |
| Cl | piperidin-1-yl | —CH$_2$C(CH$_3$)$_2$—CH$_2$— | \C=/ | =N— |
| Cl | morpholin-4-yl | —CH$_2$C(CH$_3$)$_2$—CH$_2$— | \C=/ | =N— |
| Cl | NH—SO$_2$CH$_3$ | —CH$_2$C(CH$_3$)$_2$—CH$_2$— | \C=/ | =N— |
| Cl | NH—SO$_2$C$_2$H$_5$ | —CH$_2$C(CH$_3$)$_2$—CH$_2$— | \C=/ | =N— |
| Cl | NH—SO$_2$C$_3$H$_7$-n | —CH$_2$C(CH$_3$)$_2$—CH$_2$— | \C=/ | =N— |
| Cl | NH—SO$_2$C$_3$H$_7$-i | —CH$_2$C(CH$_3$)$_2$—CH$_2$— | \C=/ | =N— |
| Cl | NH—SO$_2$C$_4$H$_9$-n | —CH$_2$C(CH$_3$)$_2$—CH$_2$— | \C=/ | =N— |
| Cl | NH—SO$_2$C$_8$H$_{17}$-n | —CH$_2$C(CH$_3$)$_2$—CH$_2$— | \C=/ | =N— |
| Cl | NH—COCH$_3$ | —CH$_2$C(CH$_3$)$_2$—CH$_2$— | \C=/ | =N— |
| Cl | NH—COC$_2$H$_5$ | —CH$_2$C(CH$_3$)$_2$—CH$_2$— | \C=/ | =N— |

TABLE 1-continued

Examples of the compounds of the formula (I)

| R¹ | R² | A | E | G |
|---|---|---|---|---|
| Cl | NH—COCF₃ | —CH₂C(CH₃)₂—CH₂— | \C=/ | =N— |
| Cl | N(CH₃)—SO₂CH₃ | —CH₂C(CH₃)₂—CH₂— | \C=/ | =N— |
| Cl | N(CH₃)—SO₂C₂H₅ | —CH₂C(CH₃)₂—CH₂— | \C=/ | =N— |
| Cl | N(CH₃)—SO₂C₃H₇-n | —CH₂C(CH₃)₂—CH₂— | \C=/ | =N— |
| Cl | NH—SO₂CF₃ | —CH₂C(CH₃)₂—CH₂— | \C=/ | =N— |
| Cl | NH—SO₂—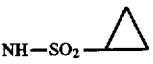 | —CH₂C(CH₃)₂—CH₂— | \C=/ | =N— |
| Cl | NH—SO₂—C₄F₉-n | —CH₂C(CH₃)₂—CH₂— | \C=/ | =N— |
| Cl | N(CH₃)SO₂CF₃ | —CH₂C(CH₃)₂—CH₂— | \C=/ | =N— |
| Cl | NH—SO₂— | —CH₂C(CH₃)₂—CH₂— | \C=/ | =N— |
| Cl | NH—SO₂CH₂—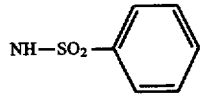 | —CH₂C(CH₃)₂—CH₂— | \C=/ | =N— |
| Cl | N(CH₃)—SO₂——CH₃ | —CH₂C(CH₃)₂—CH₂— | \C=/ | =N— |
| F | O—CH(CH₂F)₂ | —(CH₂)₅— | \C=/ | =N— |
| F | O—CH₂—C(CH₃)=CH₂ | —(CH₂)₅— | \C=/ | =N— |
| F | S—CH₂ O | —(CH₂)₅— | \C=/ | =N— |

TABLE 1-continued

Examples of the compounds of the formula (I)

| R¹ | R² | A | E | G |
|---|---|---|---|---|
| F | O—CH₂-(tetrahydropyran-2-yl) | —(CH₂)₅— | >C= | =N— |
| F | O-(1-cyclopropyl-COOC₂H₅) | —(CH₂)₅— | >C= | =N— |
| F | —S-(1-cyclobutyl-COOC₂H₅) | —(CH₂)₅— | >C= | =N— |
| F | S-(1-cyclopropyl-COOC₂H₅) | —(CH₂)₅— | >C= | =N— |
| F | S—CH₂—COO-(cyclopentyl) | —(CH₂)₅— | >C= | =N— |
| F | S—CH₂—COOC₅H₁₁-n | —(CH₂)₅— | >C= | =N— |
| F | O—CH₂-(phenyl) | —(CH₂)₅— | >C= | =N— |
| F | S—CH₂-(phenyl) | —(CH₂)₅— | >C= | =N— |
| F | O—CH₂CH₂—OCH(CH₂F)₂ | —(CH₂)₅— | >C= | =N— |
| F | S—CH(CH₃)₂ | —(CH₂)₅— | >C= | =N— |
| F | O—CH₂—CCl=CH₂ | —(CH₂)₅— | >C= | =N— |
| F | O-(phenyl) | —(CH₂)₅— | >C= | =N— |
| F | O—CH₂CN | —(CH₂)₅— | >C= | =N— |
| F | O—CH₂COOC₂H₄—OCH₃ | —(CH₂)₅— | >C= | =N— |

TABLE 1-continued

Examples of the compounds of the formula (I)

| R¹ | R² | A | E | G |
|---|---|---|---|---|
| F | O—CH₂—COO—CH(CH₃)COOC₂H₅ | —(CH₂)₅— | \C=/ | =N— |
| F | OCH₂—COOCH₂—COOC₂H₅ | —(CH₂)₅— | \C=/ | =N— |
| F | O—CHF₂ | —(CH₂)₅— | \C=/ | =N— |
| F | O—CH₂CH₂—OCH₂CF₃ | —(CH₂)₅— | \C=/ | =N— |
| F | OCH₂CF₃ | —(CH₂)₅— | \C=/ | =N— |
| F | OCF₃ | —(CH₂)₅— | \C=/ | =N— |
| F | OCH₂CH(CH₃)—OC₂H₅ | —(CH₂)₅— | \C=/ | =N— |
| F | (tetrahydrofuran-2-yl-methoxy: O—CH₂-[tetrahydrofuran]) | —(CH₂)₅— | \C=/ | =N— |
| F | OCH₂—CH=CH₂ | —(CH₂)₅— | \C=/ | =N— |
| F | OH | —(CH₂)₅— | \C=/ | =N— |
| F | OCH₂—C≡CN | —(CH₂)₅— | \C=/ | =N— |
| F | SCH₂C≡CH | —(CH₂)₅— | \C=/ | =N— |
| F | OCH₂COOC₂H₅ | —(CH₂)₅— | \C=/ | =N— |
| F | S—C(CH₃)₃ | —(CH₂)₅— | \C=/ | =N— |
| F | OCH₂—COOC₅H₁₁-n | —(CH₂)₅— | \C=/ | =N— |

TABLE 1-continued

Examples of the compounds of the formula (I)

| R¹ | R² | A | E | G |
|---|---|---|---|---|
| F | OCH(CH₃)—COOC₂H₅ | —(CH₂)₅— | \C=/ | =N— |
| F | OCH₂CH₂—OCH₃ | —(CH₂)₅— | \C=/ | =N— |
| F | OCH₂CH₂—OC₂H₅ | —(CH₂)₅— | \C=/ | =N— |
| F | O(CH₂CH₂O)₂—OC₂H₅ | —(CH₂)₅— | \C=/ | =N— |
| F | S—C₃H₇-n | —(CH₂)₅— | \C=/ | =N— |
| F | S—C₂H₅ | —(CH₂)₅— | \C=/ | =N— |
| F | S—CH₃ | —(CH₂)₅— | \C=/ | =N— |
| F | S—CH₂COOC₂H₅ | —(CH₂)₅— | \C=/ | =N— |
| F | SCH₂CH₂—COOC₂H₅ | —(CH₂)₅— | \C=/ | =N— |
| F | O—CH₂—C≡C—CH₃ | —(CH₂)₅— | \C=/ | =N— |
| F | OCH₂—CH=CH—Cl | —(CH₂)₅— | \C=/ | =N— |
| F | O—CH(CH₃)C≡CH | —(CH₂)₅— | \C=/ | =N— |
| F | OCH(CH₃)C≡C—CH₃ | —(CH₂)₅— | \C=/ | =N— |
| F | O—CH(CH₃)CH=CH₂ | —(CH₂)₅— | \C=/ | =N— |

TABLE 1-continued

Examples of the compounds of the formula (I)

| R¹ | R² | A | E | G |
|---|---|---|---|---|
| F | OCH$_2$CH=CH—CH$_3$ | —(CH$_2$)$_5$— | \C=/ | =N— |
| F | O—CH$_3$ | —(CH$_2$)$_5$— | \C=/ | =N— |
| F | O—C$_2$H$_5$ | —(CH$_2$)$_5$— | \C=/ | =N— |
| F | O—C$_3$H$_7$-n | —(CH$_2$)$_5$— | \C=/ | =N— |
| F | O—C$_3$H$_7$-iso | —(CH$_2$)$_5$— | \C=/ | =N— |
| F | O—[cyclobutyl-COOC$_2$H$_5$] | —(CH$_2$)$_5$— | \C=/ | =N— |
| F | [tetrahydrofuranyl-O—] | —(CH$_2$)$_5$— | \C=/ | =N— |
| F | NHCH$_3$ | —(CH$_2$)$_5$— | \C=/ | =N— |
| F | NHC$_2$H$_5$ | —(CH$_2$)$_5$— | \C=/ | =N— |
| F | N(CH$_3$)$_2$ | —(CH$_2$)$_5$— | \C=/ | =N— |
| F | NH—CH$_2$—COOC$_2$H$_5$ | —(CH$_2$)$_5$— | \C=/ | =N— |
| F | [piperidinyl] | —(CH$_2$)$_5$— | \C=/ | =N— |
| F | [morpholinyl] | —(CH$_2$)$_5$— | \C=/ | =N— |
| F | NH—SO$_2$CH$_3$ | —(CH$_2$)$_5$— | \C=/ | =N— |
| F | NH—SO$_2$C$_2$H$_5$ | —(CH$_2$)$_5$— | \C=/ | =N— |

TABLE 1-continued

Examples of the compounds of the formula (I)

| R¹ | R² | A | E | G |
|---|---|---|---|---|
| F | NH—SO$_2$C$_3$H$_7$-n | —(CH$_2$)$_5$— | \C= / | =N— |
| F | NH—SO$_2$C$_3$H$_7$-i | —(CH$_2$)$_5$— | \C= / | =N— |
| F | NH—SO$_2$C$_4$H$_9$-n | —(CH$_2$)$_5$— | \C= / | =N— |
| F | NH—SO$_2$C$_8$H$_{17}$-n | —(CH$_2$)$_5$— | \C= / | =N— |
| F | NH—COCH$_3$ | —(CH$_2$)$_5$— | \C= / | =N— |
| F | NH—COC$_2$H$_5$ | —(CH$_2$)$_5$— | \C= / | =N— |
| F | NH—COCF$_3$ | —(CH$_2$)$_5$— | \C= / | =N— |
| F | N(CH$_3$)—SO$_2$CH$_3$ | —(CH$_2$)$_5$— | \C= / | =N— |
| F | N(CH$_3$)—SO$_2$C$_2$H$_5$ | —(CH$_2$)$_5$— | \C= / | =N— |
| F | N(CH$_3$)—SO$_2$C$_3$H$_7$-n | —(CH$_2$)$_5$— | \C= / | =N— |
| F | NH—SO$_2$CF$_3$ | —(CH$_2$)$_5$— | \C= / | =N— |
| F | NH—SO$_2$—△ | —(CH$_2$)$_5$— | \C= / | =N— |
| F | NH—SO$_2$—C$_4$F$_9$-n | —(CH$_2$)$_5$— | \C= / | =N— |
| F | N(CH$_3$)SO$_2$CF$_3$ | —(CH$_2$)$_5$— | \C= / | =N— |

TABLE 1-continued

Examples of the compounds of the formula (I)

| R¹ | R² | A | E | G |
|---|---|---|---|---|
| F | NH—SO₂—C₆H₅ | —(CH₂)₅— | \C= / | =N— |
| F | NH—SO₂CH₂—C₆H₅ | —(CH₂)₅— | \C= / | =N— |
| F | N(CH₃)—SO₂—C₆H₄—CH₃ | —(CH₂)₅— | \C= / | =N— |
| H | OCH₂CF₃ | —(CH₂)₅— | \C= / | =N— |
| H | OCF₃ | —(CH₂)₅— | \C= / | =N— |
| H | OCH₂CH(CH₃)—OC₂H₅ | —(CH₂)₅— | \C= / | =N— |
| H | O—CH₂—(tetrahydrofuran-2-yl) | —(CH₂)₅— | \C= / | =N— |
| H | OCH₂—CH=CH₂ | —(CH₂)₅— | \C= / | =N— |
| H | OH | —(CH₂)₅— | \C= / | =N— |
| H | OCH₂—C≡CH | —(CH₂)₅— | \C= / | =N— |
| H | SCH₂C≡CH | —(CH₂)₅— | \C= / | =N— |
| H | OCH₂COOC₂H₅ | —(CH₂)₅— | \C= / | =N— |
| H | S—C(CH₃)₃ | —(CH₂)₅— | \C= / | =N— |
| H | OCH₂—COOC₅H₁₁-n | —(CH₂)₅— | \C= / | =N— |
| H | OCH(CH₃)—COOC₂H₅ | —(CH₂)₅— | \C= / | =N— |

TABLE 1-continued

Examples of the compounds of the formula (I)

| R¹ | R² | A | E | G |
|---|---|---|---|---|
| H | OCH₂CH₂—OCH₃ | —(CH₂)₅— | \C=/ | =N— |
| H | OCH₂CH₂—OC₂H₅ | —(CH₂)₅— | \C=/ | =N— |
| H | O(CH₂CH₂O)₂—OC₂H₅ | —(CH₂)₅— | \C=/ | =N— |
| H | S—C₃H₇-n | —(CH₂)₅— | \C=/ | =N— |
| H | S—C₂H₅ | —(CH₂)₅— | \C=/ | =N— |
| H | S—CH₃ | —(CH₂)₅— | \C=/ | =N— |
| H | S—CH₂COOC₂H₅ | —(CH₂)₅— | \C=/ | =N— |
| H | SCH₂CH₂—COOC₂H₅ | —(CH₂)₅— | \C=/ | =N— |
| H | O—CH₂—C≡C—CH₃ | —(CH₂)₅— | \C=/ | =N— |
| H | OCH₂CH=CH—Cl | —(CH₂)₅— | \C=/ | =N— |
| H | O—CH(CH₃)C≡CH | —(CH₂)₅— | \C=/ | =N— |
| H | OCH(CH₃)C≡C—CH₃ | —(CH₂)₅— | \C=/ | =N— |
| H | O—CH(CH₃)CH=CH₂ | —(CH₂)₅— | \C=/ | =N— |
| H | OCH₂CH=CH—CH₃ | —(CH₂)₅— | \C=/ | =N— |

TABLE 1-continued

Examples of the compounds of the formula (I)

| R¹ | R² | A | E | G |
|---|---|---|---|---|
| H | O—CH₃ | —(CH₂)₅— | \C=/ | =N— |
| H | O—C₂H₅ | —(CH₂)₅— | \C=/ | =N— |
| H | O—C₃H₇-n | —(CH₂)₅— | \C=/ | =N— |
| H | O—C₃H₇-iso | —(CH₂)₅— | \C=/ | =N— |
| H | O—(cyclobutyl)-COOC₂H₅ | —(CH₂)₅— | \C=/ | =N— |
| H | —O—(tetrahydrofuran-3-yl)—O— | —(CH₂)₅— | \C=/ | =N— |
| H | O—CH(CH₂F)₂ | —(CH₂)₅— | \C=/ | =N— |
| H | O—CH₂—C(CH₃)=CH₂ | —(CH₂)₅— | \C=/ | =N— |
| H | S—CH₂—(tetrahydrofuran-2-yl) | —(CH₂)₅— | \C=/ | =N— |
| H | O—CH₂—(tetrahydropyran-2-yl) | —(CH₂)₅— | \C=/ | =N— |
| H | O—(cyclopropyl)-COOC₂H₅ | —(CH₂)₅— | \C=/ | =N— |
| H | —S—(cyclobutyl)-COOC₂H₅ | —(CH₂)₅— | \C=/ | =N— |
| H | S—(cyclopropyl)-COOC₂H₅ | —(CH₂)₅— | \C=/ | =N— |
| H | S—CH₂—COO—(cyclopentyl) | —(CH₂)₅— | \C=/ | =N— |
| H | S—CH₂—COOC₅H₁₁-n | —(CH₂)₅— | \C=/ | =N— |

TABLE 1-continued

Examples of the compounds of the formula (I)

| R¹ | R² | A | E | G |
|---|---|---|---|---|
| H | O—CH₂—C₆H₅ | —(CH₂)₅— | \C=/ | =N— |
| H | S—CH₂—C₆H₅ | —(CH₂)₅— | \C=/ | =N— |
| H | O—CH₂CH₂—OCH(CH₂F)₂ | —(CH₂)₅— | \C=/ | =N— |
| H | S—CH(CH₃)₂ | —(CH₂)₅— | \C=/ | =N— |
| H | O—CH₂—CCl=CH₂ | —(CH₂)₅— | \C=/ | =N— |
| H | O—C₆H₅ | —(CH₂)₅— | \C=/ | =N— |
| H | O—CH₂CN | —(CH₂)₅— | \C=/ | =N— |
| H | O—CH₂COOC₂H₄—OCH₃ | —(CH₂)₅— | \C=/ | =N— |
| H | O—CH₂—COO—CH(CH₃)COOC₂H₅ | —(CH₂)₅— | \C=/ | =N— |
| H | OCH₂—COOCH₂—COOC₂H₅ | —(CH₂)₅— | \C=/ | =N— |
| H | O—CHF₂ | —(CH₂)₅— | \C=/ | =N— |
| H | O—CH₂CH₂—OCH₂CF₃ | —(CH₂)₅— | \C=/ | =N— |
| H | NHCH₃ | —(CH₂)₅— | \C=/ | =N— |
| H | NHC₂H₅ | —(CH₂)₅— | \C=/ | =N— |

TABLE 1-continued

Examples of the compounds of the formula (I)

| R¹ | R² | A | E | G |
|---|---|---|---|---|
| H | N(CH₃)₂ | —(CH₂)₅— | \C=/ | =N— |
| H | NH—CH₂—COOC₂H₅ | —(CH₂)₅— | \C=/ | =N— |
| H | ![piperidine] | —(CH₂)₅— | \C=/ | =N— |
| H | ![morpholine] | —(CH₂)₅— | \C=/ | =N— |
| H | NH—SO₂CH₃ | —(CH₂)₅— | \C=/ | =N— |
| H | NH—SO₂C₂H₅ | —(CH₂)₅— | \C=/ | =N— |
| H | NH—SO₂C₃H₇-n | —(CH₂)₅— | \C=/ | =N— |
| H | NH—SO₂C₃H₇-i | —(CH₂)₅— | \C=/ | =N— |
| H | NH—SO₂C₄H₉-n | —(CH₂)₅— | \C=/ | =N— |
| H | NH—SO₂C₈H₁₇-n | —(CH₂)₅— | \C=/ | =N— |
| H | NH—COCH₃ | —(CH₂)₅— | \C=/ | =N— |
| H | NH—COC₂H₅ | —(CH₂)₅— | \C=/ | =N— |
| H | NH—COCF₃ | —(CH₂)₅— | \C=/ | =N— |
| H | N(CH₃)—SO₂CH₃ | —(CH₂)₅— | \C=/ | =N— |
| H | N(CH₃)—SO₂C₂H₅ | —(CH₂)₅— | \C=/ | =N— |

TABLE 1-continued

Examples of the compounds of the formula (I)

| R¹ | R² | A | E | G |
|---|---|---|---|---|
| H | N(CH₃)—SO₂C₃H₇-n | —(CH₂)₅— | \C=/ | =N— |
| H | NH—SO₂CF₃ | —(CH₂)₅— | \C=/ | =N— |
| H | NH—SO₂—△ (cyclopropyl) | —(CH₂)₅— | \C=/ | =N— |
| H | NH—SO₂—C₄F₉-n | —(CH₂)₅— | \C=/ | =N— |
| H | N(CH₃)SO₂CF₃ | —(CH₂)₅— | \C=/ | =N— |
| H | NH—SO₂—C₆H₅ | —(CH₂)₅— | \C=/ | =N— |
| H | NH—SO₂CH₂—C₆H₅ | —(CH₂)₅— | \C=/ | =N— |
| H | N(CH₃)—SO₂—C₆H₄—CH₃ | —(CH₂)₅— | \C=/ | =N— |
| Cl | OCH₂CF₃ | —(CH₂)₅— | \C=/ | =N— |
| Cl | OCF₃ | —(CH₂)₅— | \C=/ | =N— |
| Cl | OCH₂CH(CH₃)—OC₂H₅ | —(CH₂)₅— | \C=/ | =N— |
| Cl | tetrahydrofuran-2-yl-CH₂—O— | —(CH₂)₅— | \C=/ | =N— |
| Cl | OCH₂—CH=CH₂ | —(CH₂)₅— | \C=/ | =N— |
| Cl | OH | —(CH₂)₅— | \C=/ | =N— |

TABLE 1-continued

Examples of the compounds of the formula (I)

| R¹ | R² | A | E | G |
|---|---|---|---|---|
| Cl | OCH₂—C≡CH | —(CH₂)₅— | \C=/ | =N— |
| Cl | SCH₂C≡CH | —(CH₂)₅— | \C=/ | =N— |
| Cl | OCH₂COOC₂H₅ | —(CH₂)₅— | \C=/ | =N— |
| Cl | S—C(CH₃)₃ | —(CH₂)₅— | \C=/ | =N— |
| Cl | OCH₂COOC₂H₅H₁₁-n | —(CH₂)₅— | \C=/ | =N— |
| Cl | OCH(CH₃)—COOC₂H₅ | —(CH₂)₅— | \C=/ | =N— |
| Cl | OCH₂CH₂—OCH₃ | —(CH₂)₅— | \C=/ | =N— |
| Cl | OCH₂CH₂—OC₂H₅ | —(CH₂)₅— | \C=/ | =N— |
| Cl | O(CH₂CH₂O)₂—OC₂H₅ | —(CH₂)₅— | \C=/ | =N— |
| Cl | S—C₃H₇-n | —(CH₂)₅— | \C=/ | =N— |
| Cl | S—C₂H₅ | —(CH₂)₅— | \C=/ | =N— |
| Cl | S—CH₃ | —(CH₂)₅— | \C=/ | =N— |
| Cl | S—CH₂COOC₂H₅ | —(CH₂)₅— | \C=/ | =N— |
| Cl | SCH₂CH₂—COOC₂H₅ | —(CH₂)₅— | \C=/ | =N— |
| Cl | O—CH₂—C≡C—CH₃ | —(CH₂)₅— | \C=/ | =N— |

TABLE 1-continued

Examples of the compounds of the formula (I)

| R¹ | R² | A | E | G |
|---|---|---|---|---|
| Cl | OCH₂—CH=CH—Cl | —(CH₂)₅— | \C=/ | =N— |
| Cl | O—CH(CH₃)C≡CH | —(CH₂)₅— | \C=/ | =N— |
| Cl | OCH(CH₃C≡C—CH₃ | —(CH₂)₅— | \C=/ | =N— |
| Cl | O—CH(CH₃)CH=CH₂ | —(CH₂)₅— | \C=/ | =N— |
| Cl | OCH₂CH=CH—CH₃ | —(CH₂)₅— | \C=/ | =N— |
| Cl | O—CH₃ | —(CH₂)₅— | \C=/ | =N— |
| Cl | O—C₂H₅ | —(CH₂)₅— | \C=/ | =N— |
| Cl | O—C₃H₇-n | —(CH₂)₅— | \C=/ | =N—. |
| Cl | O—C₃H₇-iso | —(CH₂)₅— | \C=/ | =N— |
| Cl | O—[cyclobutyl]—COOC₂H₅ | —(CH₂)₅— | \C=/ | =N— |
| Cl | —O—[tetrahydrofuranyl]—O | —(CH₂)₅— | \C=/ | =N— |
| Cl | O—CH(CH₂F)₂ | —(CH₂)₅— | \C=/ | =N— |
| Cl | O—CH₂—C(CH₃)=CH₂ | —(CH₂)₅— | \C=/ | =N— |
| Cl | S—CH₂—[tetrahydrofuranyl]—O | —(CH₂)₅— | \C=/ | =N— |

TABLE 1-continued

Examples of the compounds of the formula (I)

| R¹ | R² | A | E | G |
|---|---|---|---|---|
| Cl | O—CH₂—(tetrahydropyran-2-yl) | —(CH₂)₅— | \C=/ | =N— |
| Cl | O—(1-ethoxycarbonylcyclopropyl) (COOC₂H₅) | —(CH₂)₅— | \C=/ | =N— |
| Cl | —S—(1-ethoxycarbonylcyclobutyl) (COOC₂H₅) | —(CH₂)₅— | \C=/ | =N— |
| Cl | S—(1-ethoxycarbonylcyclopropyl) (COOC₂H₅) | —(CH₂)₅— | \C=/ | =N— |
| Cl | S—CH₂—COO—(cyclopentyl) | —(CH₂)₅— | \C=/ | =N— |
| Cl | S—CH₂—COOC₅H₁₁-n | —(CH₂)₅— | \C=/ | =N— |
| Cl | O—CH₂—(phenyl) | —(CH₂)₅— | \C=/ | =N— |
| Cl | S—CH₂—(phenyl) | —(CH₂)₅— | \C=/ | =N— |
| Cl | O—CH₂CH₂—OCH(CH₂F)₂ | —(CH₂)₅— | \C=/ | =N— |
| Cl | S—CH(CH₃)₂ | —(CH₂)₅— | \C=/ | =N— |
| Cl | O—CH₂—CCl=CH₂ | —(CH₂)₅— | \C=/ | =N— |
| Cl | O—(phenyl) | —(CH₂)₅— | \C=/ | =N— |
| Cl | O—CH₂CN | —(CH₂)₅— | \C=/ | =N— |
| Cl | O—CH₂COOC₂H₄OCH₃ | —(CH₂)₅— | \C=/ | =N— |

TABLE 1-continued

Examples of the compounds of the formula (I)

| R¹ | R² | A | E | G |
|---|---|---|---|---|
| Cl | O—CH₂—COO—CH(CH₃)COOC₂H₅ | —(CH₂)₅— | \C=/ | =N— |
| Cl | OCH₂—COOCH₂—COOC₂H₅ | —(CH₂)₅— | \C=/ | =N— |
| Cl | O—CHF₂ | —(CH₂)₅— | \C=/ | =N— |
| Cl | O—CH₂CH₂—OCH₂CF₃ | —(CH₂)₅— | \C=/ | =N— |
| Cl | NHCH₃ | —(CH₂)₅— | \C=/ | =N— |
| Cl | NHC₂H₅ | —(CH₂)₅— | \C=/ | =N— |
| Cl | N(CH₃)₂ | —(CH₂)₅— | \C=/ | =N— |
| Cl | NH—CH₂—COOC₂H₅ | —(CH₂)₅— | \C=/ | =N— |
| Cl | piperidin-1-yl | —(CH₂)₅— | \C=/ | =N— |
| Cl | morpholin-4-yl | —(CH₂)₅— | \C=/ | =N— |
| Cl | NH—SO₂CH₃ | —(CH₂)₅— | \C=/ | =N— |
| Cl | NH—SO₂C₂H₅ | —(CH₂)₅— | \C=/ | =N— |
| Cl | NH—SO₂C₃H₇-n | —(CH₂)₅— | \C=/ | =N— |
| Cl | NH—SO₂C₃H₇-i | —(CH₂)₅— | \C=/ | =N— |
| Cl | NH—SO₂C₄H₉-n | —(CH₂)₅— | \C=/ | =N— |

TABLE 1-continued

Examples of the compounds of the formula (I)

| R¹ | R² | A | E | G |
|---|---|---|---|---|
| Cl | NH—SO₂C₈H₁₇-n | —(CH₂)₅— | \C=/ | =N— |
| Cl | NH—COCH₃ | —(CH₂)₅— | \C=/ | =N— |
| Cl | NH—COC₂H₅ | —(CH₂)₅— | \C=/ | =N— |
| Cl | NH—COCF₃ | —(CH₂)₅— | \C=/ | =N— |
| Cl | N(CH₃)—SO₂CH₃ | —(CH₂)₅— | \C=/ | =N— |
| Cl | N(CH₃)—SO₂C₂H₅ | —(CH₂)₅— | \C=/ | =N— |
| Cl | N(CH₃)—SO₂C₃H₇-n | —(CH₂)₅— | \C=/ | =N— |
| Cl | NH—SO₂CF₃ | —(CH₂)₅— | \C=/ | =N— |
| Cl | NH—SO₂—△ | —(CH₂)₅— | \C=/ | =N— |
| Cl | NH—SO₂—C₄F₉-n | —(CH₂)₅— | \C=/ | =N— |
| Cl | N(CH₃)SO₂CF₃ | —(CH₂)₅— | \C=/ | =N— |
| Cl | NH—SO₂—⌬ | —(CH₂)₅— | \C=/ | =N— |
| Cl | NH—SO₂CH₂—⌬ | —(CH₂)₅— | \C=/ | =N— |
| Cl | N(CH₃)—SO₂—⌬—CH₃ | —(CH₂)₅— | \C=/ | =N— |

The above-listed general radical definitions, or those given in preference ranges, apply both to the end products of the formula (I) and, correspondingly, to the starting compounds or intermediates which are in each case required for the preparation. These radical definitions may be combined among themselves arbitrarily, i.e. between the given ranges of preferred compounds as well.

If, for example, 1-[N-(4-cyano-2,5-difluoro-phenyl)]2-imino-piperidine-thiocarboxamide is used as the starting compound, and sulphur as the oxidizing agent, the course of the reaction in process (a) according to the invention can then be outlined by the following formula scheme:

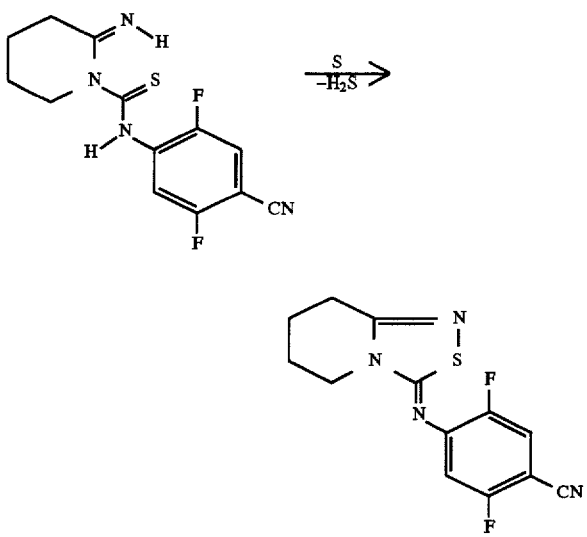

If, for example, 1-[N-(4-cyano-2-chloro-5-ethoxyphenyl)]-tetrahydro-(2H)-pyridazine-thiocarboxamide and phosgene are used as the starting compounds, the course of the reaction in process (b) according to the invention can then be outlined by the following formula scheme:

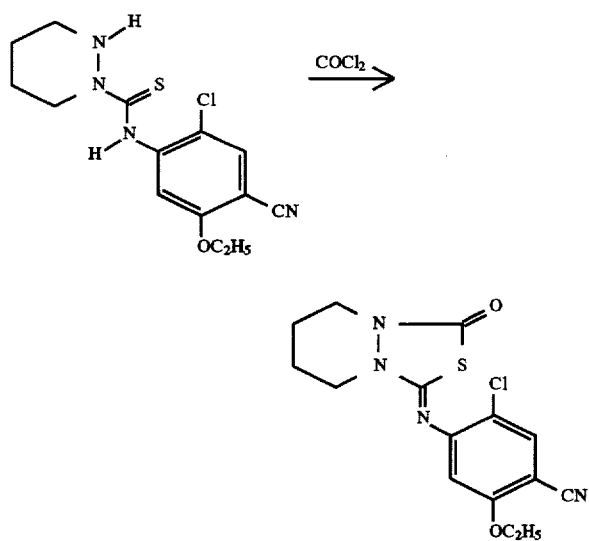

If, for example, 9-(4-cyano-2,5-difluoro-phenyl-imino)-8-thia-1,6-diazabicyclo [4.3.0]nonan-7-one and methanesulphonamide are used as the starting compounds, the course of the reaction in process (c) according to the invention can then be outlined by the following formula scheme:

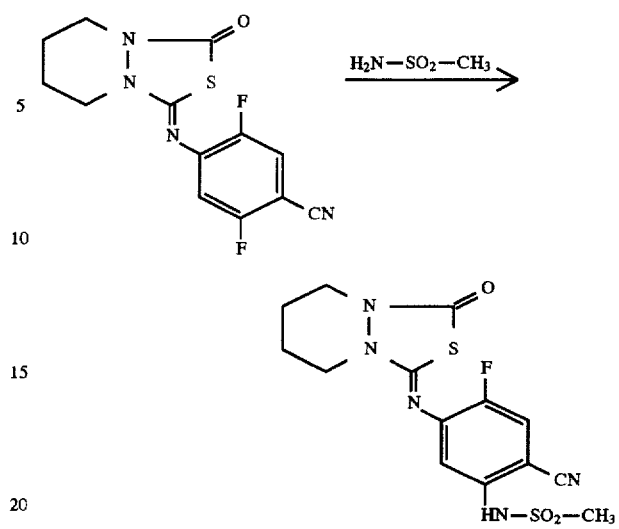

The substituted thiocarbonylamino compounds to be used in process (a) according to the invention as starting compounds for preparing the compounds of the formula (I) are defined generally by the formula (II). In formula (II), $R^1$, $R^2$ and A preferably or in particular have those meanings which have already been indicated above, in connection with the description of the compounds of the formula (I) according to the invention, as being preferred or in particular preferred for $R^1$, $R^2$ and A.

The substituted thiocarbonylamino compounds of the formula (II) required as starting compounds are still not known from the literature; as novel compounds, they are a subject of the present application.

The novel compounds of the formula (II) are obtained when cyanoaryl isothiocyanates of the general formula (VIII)

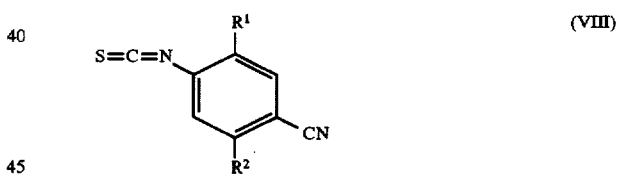

in which $R^1$ and $R^2$ have the abovementioned meanings, are reacted with imino compounds of the general formula (IX)

in which

A has the abovementioned meaning, optionally in the presence of a diluent, such as, for example, toluene, and at temperatures of between 0° C. and 100° C. (cf. the preparation examples).

With the exception of 3-chloro-4-cyano-phenyl isothiocyanate and 3-trifluoromethyl-4-cyanophenyl isothiocyanate, the cyanoaryl isothiocyanates of the formula (VIII) required as precursors are still not known from the literature; as novel compounds, they are a subject of the present application.

The novel cyanoaryl isothiocyanates of the formula (VIII) are obtained when corresponding cyanoarylamines of the general formula (X)

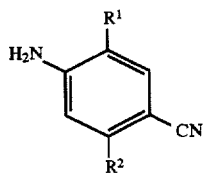 (X)

in which

R$^1$ and R$^2$ have the abovementioned meanings, are reacted with thiophosgene, optionally in the presence of a reaction auxiliary, such as, for example, calcium carbonate, and optionally in the presence of diluents, such as, for example, methylene chloride and water, and at temperatures of between 0° C. and 100° C. (cf. the preparation examples).

The cyanoarylamines of the general formula (X) are known and/or can be prepared by processes which are known per se (cf. EP-A 224001).

The cyanoarylamines of the general formula (Xa)

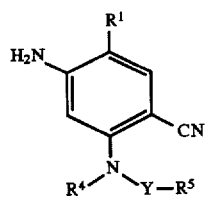 (Xa)

in which

R$^1$, R$^4$ and R$^5$ have the abovementioned meanings, and Y represents CO or SO$_2$, are still not known from the literature and, as novel compounds, are a subject of the present application.

The novel cyanoarylamines of the formula (Xa) are obtained when corresponding halogenoarylamines of the general formula (XI)

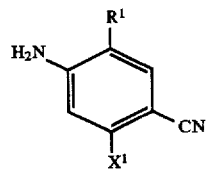 (XI)

in which

R$^1$ and X$^1$ have the abovementioned meanings, are reacted with amides of the general formula (XII)

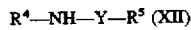
R$^4$—NH—Y—R$^5$ (XII)

in which

R$^4$, R$^5$ and Y have the abovementioned meanings, optionally in the presence of an acid acceptor, such as, for example, potassium carbonate, and optionally in the presence of a diluent, such as, for example, N-methylpyrrolidone, and at temperatures of between 100° C. and 200° C. (cf. the preparation examples).

The imino compounds of the formula (IX), which are additionally required as precursors, are known and/or can be prepared by processes which are known per se (cf. Angew. Chem. 81 (1969), 431–432; loc. cit. Int. Ed. Engl. 8 (1969), 457–458; J. Org. Chem. 33 (1968), 2109–2111).

The process (a) according to the invention is carried out using oxidizing agents or dehydrogenating agents. In this context, practically all reagents are suitable which are customarily used for oxidizing or dehydrogenating organic chemical compounds. Those which may be mentioned by way of example are oxygen, sulphur, hydrogen peroxide, sodium persulphate, sodium thiosulphate, chlorine, bromine and iodine.

The process (a) according to the invention is preferably carried out using a diluent. All customary organic or inorganic solvents are suitable for use as diluents. These include, in particular, aliphatic, alicyclic or aromatic, optionally halogenated, hydrocarbons, such as, for example, benzine, benzene, toluene, xylene, chlorobenzene, dichlorobenzene, petroleum ether, hexane, cyclohexane, dichloromethane, chloroform or carbon tetrachloride; ethers, such as diethyl ether, diisopropyl ether, dioxane, tetrahydrofuran, ethylene glycol dimethyl ether or ethylene glycol diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide, or alcohols, such as methanol, ethanol, n- or i-propanol, or n-, i-, s- or t-butanol, as well as water.

The process (a) according to the invention is optionally carried out in the presence of a suitable reaction auxiliary. The customary inorganic or organic bases are particularly suitable for use as such reaction auxiliaries. These bases include, for example, alkaline earth metal or alkali metal hydroxides, such as sodium hydroxide, potassium hydroxide, calcium hydroxide, and also ammonium hydroxide, alkali metal (hydrogen)carbonates, such as sodium (hydrogen)carbonate, potassium (hydrogen) carbonate or ammonium carbonate, alkali metal or alkaline earth metal acetates, such as sodium acetate, potassium acetate, calcium acetate or ammonium acetate, alkali metal alcoholates, such as sodium or potassium methoxide, sodium or potassium ethoxide, or sodium or potassium tert-butoxide, as well as tertiary amines, such as trimethylamine, triethylamine, tributylamine, N,N-dimethylaniline, pyridine, N-methylpyridine, 4-dimethylaminopyridine, diazabicyclooctane (DABCO), diazabicyclononene (DBN) or diazabicycloundecene (DBU).

In carrying out the process (a) according to the invention, the reaction temperatures can be varied over a relatively wide range. In general, temperatures of between 0° C. and 150° C., preferably temperatures of between 20° C. and 120° C., are employed.

In general the process (a) according to the invention is carried out under atmospheric pressure. However, it is also possible to carry it out under elevated or reduced pressure.

For carrying out the process (a) according to the invention, the starting compounds which are in each case required are generally employed in approximately equimolar or equivalent quantities. However, it is also possible to use one of the components employed on each occasion in a relatively large excess. In general, the reaction is carried out in a suitable diluent and the reaction mixture is stirred, until conversion is complete, at the temperature which is required in each case. The working up is effected in accordance with customary methods.

The substituted thiocarbonylamino compounds to be used in process (b) according to the invention as starting compounds for preparing the compounds of the formula (I) are defined generally by the formula (III).

In formula (III), R$^1$, R$^2$ and A preferably or in particular have those meanings which have already been indicated above, in connection with the description of the compounds of the formula (I) according to the invention, as being preferred or particularly preferred for $R^1$, $R^2$ and A.

The substituted thiocarbonylamino compounds of the formula (III) which are required as starting compounds are still not known from the literature; as novel compounds, they are a subject of the present application.

The novel compounds of the formula (III) are obtained when diazacycloalkanes or diazacycloalkenes of the general formula (XI)

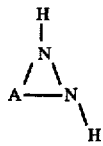 (XI)

in which

A has the abovementioned meaning, are reacted with cyanoaryl isothiocyanates of the-general formula (VIII)—above— optionally in the presence of a diluent, such as, for example, toluene, and at temperatures of between 0° C. and 100° C. (cf. the preparation examples).

The diazacycloalkanes or diazacycloalkenes of the formula (XI) which are required as precursors are known and/or can be prepared by processes which are known per se (cf. J. Org. Chem. 35 (1970), 1468–1471; Tetrahedron 31 (1975), 165–170).

The process (b) according to the invention is preferably carried out using a diluent. All customary inert organic solvents are suitable as diluents. The solvents include, in particular, aliphatic, alicyclic or aromatic, optionally halogenated, hydrocarbons, such as, for example, benzine, benzene, toluene, xylene, chlorobenzene, dichlorobenzene, petroleum ether, hexane, cyclohexane, dichloromethane, chloroform or carbon tetrachloride; ethers, such as diethyl ether, diisopropyl ether, dioxane, tetrahydrofuran, ethylene glycol dimethyl ether or ethylene glycol diethyl ether; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide.

In carrying out process (b) according to the invention, the reaction temperatures can be varied over a relatively wide range. In general, temperatures of between 0° C. and 150° C., preferably temperatures of between 10° C. and 100° C., are employed.

In general, process (b) according to the invention is carried out under atmospheric pressure. However, it is also possible to carry it out under elevated or reduced pressure.

For carrying out process (b) according to the invention, the starting compounds which are required in each case are generally employed in approximately equimolar or equivalent quantities. However, it is also possible to use one of the components employed on each occasion in a relatively large excess. In general, the reaction is carried out in a suitable diluent and the reaction mixture is stirred, until the conversion is complete, at the temperature which is required in each case. The working up is effected in accordance with customary methods (cf. the preparation examples).

The substituted cyanoarylimino heterocycles to be used as starting compounds in process (c) according to the invention are defined generally by the formula (Ia). In formula (Ia), $R^1$, A, E and G preferably or in particular have those meanings which have already been indicated above, in connection with the description of the compounds of the formula (I) according to the invention, as being preferred or particularly preferred for $R^1$, A, E and G;

$X^1$ preferably represents fluorine or chlorine, and, in particular, represents fluorine.

The starting compounds of the formula (Ia) are novel compounds, in accordance with the invention; they may be prepared by processes (a) or (b) according to the invention.

Process (c) according to the invention is preferably carried out using a diluent. All customary organic or inorganic solvents are suitable for use as diluents. These solvents include, in particular, aliphatic, alicyclic or aromatic, optionally halogenated, hydrocarbons, such as, for example, benzine, benzene, toluene, xylene, chlorobenzene, dichlorobenzene, petroleum ether, hexane, cyclohexane, dichloromethane, chloroform or carbon tetrachloride; ethers, such as diethyl ether, diisopropyl ether, dioxane, tetrahydrofuran, ethylene glycol dimethyl ether or ethylene glycol diethyl ether; ketones, such as acetone, butanone -or methyl isobutyl ketone; nitriles, such as acetonitrile, propionitrile or benzonitrile; amaides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide, or alcohols, such as methanol, ethanol, n- or i-propanol or n-, i-, s- or t-butanol, as well as water.

The process (c) according to the invention is optionally carried out in the presence of an acid acceptor. The customary inorganic or organic bases are particularly suitable for use as such acceptors. These bases include, for example, alkaline earth metal or alkali metal hydroxides, such as sodium hydroxide, potassium hydroxide, calcium hydroxide, and also ammonium hydroxide, alkali metal (hydrogen)carbonates, such as sodium (hydrogen)carbonate, potassium (hydrogen)carbonate or ammonium carbonate, alkali metal or alkaline earth metal acetates, such as sodium acetate, potassium acetate, calcium acetate or ammonium acetate, alkali metal alcoholates, such as sodium or potassium methoxide, sodium or potassium ethoxide or sodium or potassium tertbutoxide, as well as tertiary amines, such as trimethylamine, triethylamine, tributylamine, N,N-dimethylaniline, pyridine, N-methylpiperidine, 4-dimethylaminopyridine, diazabicyclooctane (DABCO), diazabicyclononene (DBN) or diazabicycloundecene (DBU).

In carrying out process (c) according to the invention, the reaction temperatures can be varied over a relatively wide range. In general, temperatures of between 0° C. and 150° C., preferably temperatures of between 10° C. and 120° C., are employed.

In general, process (c) according to the invention is carried out under atmospheric pressure. However, it is also possible to carry it out under elevated or reduced pressure.

For carrying out process (c) according to the invention, the starting compounds which are required in each case are generally employed in approximately equimolar or equivalent quantities. However, it is also possible to use one of the components employed on each occasion in a relatively large excess. In general, the reaction is carried out in a suitable diluent and the reaction mixture is stirred, until the conversion is complete, at the temperature which is required in each case. The working up is effected in accordance with customary methods.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these-genera-, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The compounds of the formula (I) according to the invention are particularly suitable for selectively combating monocotyledonous and dicotyledonous weeds in monocotyledonous cultures, both in the pre-emergence and postemergence processes.

The active compounds can be converted into the customary formulations, such as solutions, emulsions, suspensions, powders, foams, pastes, granules, aerosols, natural and synthetic materials impregnated with active compound, and very fine capsules in polymeric substances.

These formulations are produced in a known manner, for example by mixing the active compounds with extenders, that is liquid solvents, liquified gases under pressure and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

For controlling weeds, the active compounds according to the invention, as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such-as, for example, dichloropicolinic acid, dicamba or picloram; aryloxyalkanoic acids such as, for example, 2,4-D, 2,4-DB, 2,4-DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chloropropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuronmethyl, triasulfuron and tribenuron-methyl; thiocarbamates such as, for example, butylate, cycloate, diallate, EPTC, esprocarb, molinate, prosulfocarb, thiobencarb and triallate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules.

They are used in the customary manner, for example by watering, spraying, atomizing or scattering.

The active compounds according to the invention can be applied either before or after emergence of-the plants. They can also be incorporated into the soil before sowing.

The amount of active compound used can vary within a substantial range, it depends essentially on the nature of the desired effect. In general, the amounts used are between 0.001 and 10 kg of active compound per hectare of soil surface, preferably between 0.005 and 5 kg per hectare.

The preparation and use of the active compounds according to the invention can be seen from the following examples.

The preparation and use of the active compounds according to the invention can be seen from the following examples.

Preperations examples:

EXAMPLE 1

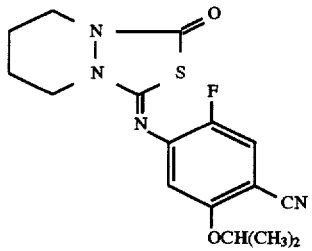

26 ml (0.05 mol) of a 20% solution of phosgene in toluene are added dropwise, at 20° C., to a solution of 9.7 g (0.03 mol) of 1-[N-(4-cyano-2-fluoro-5-i-propoxyphenyl)]-tetrahydro-(2H)-pyridazine-thiocarboxamide in 150 ml of dichloromethane. The reaction mixture is stirred at 20° C. for 3 hours and then added to about the same quantity of ice water. The organic phase is separated off, dried with magnesium sulphate and filtered. The filtrate is concentrated in a water suction vacuum and the residue is purified by column chromatography (silica gel, dichloromethane).

1.4 g (13% of theory) of 9-(4-cyano-2-fluoro-5-isopropoxy-phenyl-imino)-8-thia-1,6-diazabiazabicyclo [4.3.0]-nonan-7-one are obtained with a melting point of 108° C.

EXAMPLE 2

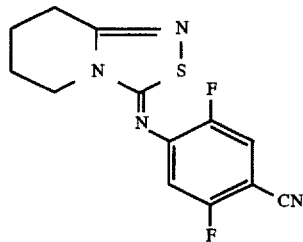

A solution of 3.2 g (0.08 mol) of sodium hydroxide in 10 ml of water is added, at 0° C., to a mixture of 10.8 g (0.08 mol) of 2-iminopiperidine hydrochloride and 100 ml of dichloromethane. The mixture is then stirred for one hour, after which a solution of 15.7 g (0.08 mol) of 4-cyano-2,5-difluorophenyl isothiocyanate in 150 ml of dichloromethane is added dropwise at from 0° C. to 5° C. The mixture is then stirred at room temperature for three hours. Subsequently, the reaction mixture is cooled down to –20° C. and 12.8 g (0.08 mol) of bromine in 40 ml of dichloromethane are added to it. This mixture is then stirred for three hours, after which the solid is filtered off and the filtrate is washed successively with sodium hydrogencarbonate solution and water. The organic phase is dried over magnesium sulphate and freed of solvent in vacuo. The remaining solid is recrystallized from a little acetonitrile.

3.1 g (13% of theory) of 9-(4-cyano-2,5-difluoro-phenylimino)-8-thia-1,7-diazabicyclo[4.3.0]non-6-ene are obtained with a melting point of 137° C.

The compounds of the formula (I) listed in Table 2 below, for example, can also be prepared in analogy with Examples 1 and 2 and in correspondence with the general description of the preparation processes according to the invention.

TABLE 2

Examples of compounds of the formula (I)

| Ex. No. | R¹ | R² | A | E | G | Melting point (°C.) |
|---|---|---|---|---|---|---|
| 3 | F | NHSO₂CH₃ | —(CH₂)₄— | —C= | =N— | |
| 4 | F | O—CH(CH₃)₂ | —(CH₂)₄— | —C= | =N— | |
| 5 | F | NHSO₂C₂H₅ | —(CH₂)₄— | —C= | =N— | |
| 6 | F | OCH(CH₃)₂ | —CH₂—(CH₃)₂—CH₂— | —C= | =N— | |

TABLE 2-continued

Examples of compounds of the formula (I)

| Ex. No. | $R^1$ | $R^2$ | A | E | G | Melting point (°C.) |
|---|---|---|---|---|---|---|
| 7 | F | F | —CH$_2$—CH$_2$—CH=CH— | N | \C=O/ | 85 |
| 8 | F | NHSO$_2$C$_3$H$_7$ | —(CH$_2$)$_4$ | —C= | =N— | 140 |
| 9 | F | F | —(CH$_2$)$_4$ | —C= | =N— | 200 |
| 10 | F | OC$_2$H$_5$ | —(CH$_2$)$_4$ | —C= | =N— | 194 |
| 11 | F | OC$_2$H$_5$ | —CH$_2$—CH$_2$—CH=CH— | N | \C=O/ | 135 |
| 12 | F | OC$_2$H$_4$OC$_2$H$_4$OCH$_3$ | —CH$_2$—CH$_2$—CH=CH— | N | \C=O/ | (amorph) |
| 13 | F | NHSO$_2$C$_2$H$_5$ | —(CH$_2$)$_4$ | N | \C=O/ | 174 |
| 14 | F | NHSO$_2$CH$_3$ | —(CH$_2$)$_4$ | N | \C=O/ | 215 |
| 15 | F | NHSO$_2$C$_3$H$_7$ | —(CH$_2$)$_4$ | N | \C=O/ | 176 |
| 16 | F | OCH(CH$_3$)$_2$ | —(CH$_2$)$_4$ | N | \C=O/ | 106 |

Starting Compounds of the Formula (III)

EXAMPLE (III-1)

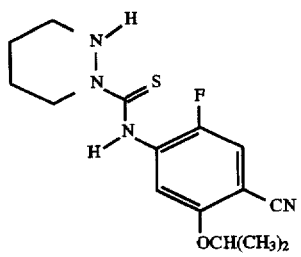

8.0 g (34 mmol) of 4-cyano-2-fluoro-5-isopropoxy-phenyl isothiocyanate are added, at 20° C. and while stirring, to a solution of 2.9 g (34 mmol) of hexahydropyridazine in 40 ml of toluene. The reaction mixture is stirred at 20° C. for 16 hours and subsequently concentrated in a water suction vacuum.

10.3 g (94% of theory) of 1-[N-(4-cyano-2-fluoro-5-isopropoxy-phenyl)]-tetrahydro-(2H)-pyridazine-thio-carboxamide are obtained as an oily residue which gradually solidifies in crystalline form.

Melting point: 42° C.

TABLE 3

Example of compounds of the formula (III)

| Ex. No. | $R^1$ | $R^1$ | A | Melting point (°C.) |
|---|---|---|---|---|
| III-2 | F | F | —CH$_2$—CH$_2$—CH$_2$—CH= | 126 |
| III-3 | F | OC$_2$H$_4$OC$_2$H$_4$OCH$_3$ | —CH$_2$—CH$_2$—CH=CH— | 58 |
| III-4 | F | NHSO$_2$CH$_3$ | —(CH$_2$)$_4$— | |
| III-5 | F | OCH(CH$_3$)$_2$ | —CH$_2$—CH$_2$—CH=CH— | 147 |

Starting Compounds of the Formula (VIII)

EXAMPLE (VIII-1)

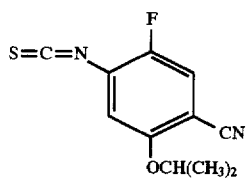

7.8 g (0.04 mol) of 4-cyano-2-fluoro-5-isopropoxy-aniline in 25 ml of dichloromethane are added, at about 30° C. and while stirring, to a mixture consisting of 6 g (0.06 mol) of calcium carbonate, 30 ml of water, 6.9 g (0.06 mol) of thiophosgene and 30 ml of dichloromethane. The reaction mixture is stirred at 30° C. to 35° C. for about 18 hours. After filtration, the organic phase is then separated off, dried with magnesium sulphate and filtered. The solvent is carefully distilled off from the filtrate in a water suction vacuum.

8.4 g (89% of theory) of 4-cyano-2-fluoro-5-isopropoxyphenyl isothiocyanate are obtained as an oily residue which gradually solidifies in crystalline form.

Melting point: 73° C.

TABLE 4

Examples of the compounds of the formula (VIII)

| Example No. | $R^1$ | $R^2$ | Melting point (°C.) |
|---|---|---|---|
| (VIII-2) | F | F | 37 |
| (VIII-3) | F | $NHSO_2CH_3$ | 166 |

Starting Compounds of the Formula (X):

EXAMPLE X-1

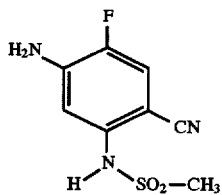

A mixture consisting of 92.4 g (0.6 mol) of 4-cyano-2,5difluoro-aniline, 60 g (0.60 mol) of methanesulphonamide, 166 g of potassium carbonate and 80 ml of N-methylpyrrolidone is heated at 180° C. for 10 hours. After having been cooled down, the mixture is stirred into 5 litres of water and the resulting solution is washed twice with 400 ml of ethyl acetate on each occasion. The aqueous phase is then overlaid with 300 ml of ethyl acetate and acidified with 10% hydrochloric acid. The product, which arises in crystalline form, is then isolated by filtering off with suction.

70 g (51% of theory) of N-(5-amino-2-cyano-4-fluorophenyl)-methanesulphonamide are obtained with a melting point of 238° C.

TABLE 5

Examples of the compounds of the formula (X)

| Example No. | $R^1$ | $R^2$ | Melting point (°C.) |
|---|---|---|---|
| X-2 | F | $NH-SO_2C_2H_5$ | |
| X-3 | H | $NHSO_2CH_3$ | |
| X-4 | F | $NHSO_2C_3H_7$-n | |
| X-5 | F | $NHSO_2C_3H_7$-iso | |
| X-6 | F | $NHSO_2$—⟨phenyl⟩ | |
| X-7 | F | $NH-SO_2$—⟨phenyl⟩—$CH_3$ | |
| X-8 | H | $NH-SO_2C_2H_5$ | |
| X-9 | Cl | $NHSO_2CH_3$ | |
| X-10 | Cl | $NH-SO_2C_2H_5$ | |

Application Examples

EXAMPLE A

Post-emergence test

Solvent: 5 parts by weight of acetone Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. After three weeks, the degree of damage to the plants is rated in % damage in comparison to the development of the untreated control.

The figures denote:

0%=no action (like untreated control)
100%=total destruction

When used in a quantity of 15 g/ha, the compound in accordance with Preparation Example 1, for example, exhibits a strong effect in this test against weeds such as Abutilon (100%), Amaranthus (80%), Chenopodium (95%), Ipomoea (100%) and Veronica (85%), while being very well tolerated by cultivated plants, such as, for example, barley (0%).

EXAMPLE B

Pre-emergence test

Solvent: 5 parts by weight of acetone Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive.

After three weeks, the degree of damage to the plants is rated in % damage in comparison to the development of the untreated control.

The figures denote:

0%=no action (like untreated control)

100%=total destruction

When used in a quantity of 60 g/ha, the compound in accordance with Preparation Example 1, for example, exhibits a strong effect in this test against weeds such as Aeopecurus (90%), Digiteria (95%), Abutilon 100%), Chenopodium 100%), Matricaria (100%) and Dinapis (80%), while being very well tolerated by cultivated plants, such as, for example, barley (0%).

It will be understood that the specification and examples are illustrative but not limitative of the present invention and that other embodiments within the spirit and scope of the invention will suggest themselves to those skilled in the art.

What is claimed is:

1. A substituted 4-cyanoaniline of the general formula (Xa)

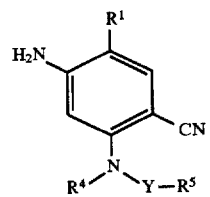

wherein $R^1$ represents hydrogen or halogen, $R^4$ represents hydrogen or alkyl, $R^5$ represents alkyl, alkenyl, alkinyl, cycloalkyl, cycloalkylalkyl, aryl or arylalkyl each of which is optionally substituted, and Y represents CO or $SO_2$.

* * * * *